(12) United States Patent
Malkowski et al.

(10) Patent No.: US 8,968,355 B2
(45) Date of Patent: Mar. 3, 2015

(54) ARTICULATING SURGICAL DEVICE

(75) Inventors: Jaroslaw T. Malkowski, Trumbull, CT (US); Ramiro Cabrera, Cheshire, CT (US); Richard Fortier, Concord, MA (US); Andrew Ziegler, Arlington, MA (US); Amos Cruz, Wrentham, MA (US); Gene A. Stellon, Burlington, CT (US); Steve Evans, Westford, MA (US)

(73) Assignee: Covidien LP, Mansfield, MA (US)

( * ) Notice: Subject to any disclaimer, the term of this patent is extended or adjusted under 35 U.S.C. 154(b) by 432 days.

(21) Appl. No.: 13/047,930

(22) Filed: Mar. 15, 2011

(65) Prior Publication Data

US 2011/0184459 A1 Jul. 28, 2011

Related U.S. Application Data

(63) Continuation-in-part of application No. 12/511,614, filed on Jul. 29, 2009, now Pat. No. 8,801,752.

(60) Provisional application No. 61/424,251, filed on Dec. 17, 2010, provisional application No. 61/316,404, filed on Mar. 23, 2010, provisional application No. 61/085,997, filed on Aug. 4, 2008.

(51) Int. Cl.
*A61B 17/00* (2006.01)
*A61B 18/14* (2006.01)
(Continued)

(52) U.S. Cl.
CPC ............. *A61B 18/1445* (2013.01); *A61B 17/29* (2013.01); *A61B 17/2909* (2013.01);
(Continued)

(58) Field of Classification Search
CPC ................... A61M 25/0147; A61M 2025/015; A61M 25/0136; A61B 17/00; A61B 1/045; A61B 1/00; A61B 17/28; A61B 17/32

USPC ................. 606/205–209, 1, 174; 604/528; 600/139–142, 146, 149
See application file for complete search history.

(56) References Cited

U.S. PATENT DOCUMENTS

| | | | |
|---|---|---|---|
| 2,028,635 A | 1/1936 | Wappler | |
| 2,507,710 A | 5/1950 | Grosso | |

(Continued)

FOREIGN PATENT DOCUMENTS

| | | |
|---|---|---|
| EP | 0095970 A2 | 12/1983 |
| EP | 0448284 A2 | 9/1991 |

(Continued)

OTHER PUBLICATIONS

European Search Report for EP 08 252797.9-2319 date of completion is Nov. 7, 2008 (6 pages).

(Continued)

*Primary Examiner* — Katherine Dowe
*Assistant Examiner* — Amy Shipley

(57) ABSTRACT

An articulation mechanism for a surgical instrument includes an articulation assembly, a plurality of cables, and a trigger. The cables are coupled to the articulation assembly at a proximal end thereof and extend distally therefrom. The cables are configured to engage an end effector assembly of the surgical instrument at a distal end thereof. The trigger is coupled to the articulation assembly and is selectively moveable from a shipping position to a use position. In the shipping position, the cables are substantially un-tensioned. In the use position, the cables are disposed in an initial tensioned position. In the use position, the trigger is moveable between an unlocked position and a locked position. In the unlocked position, the cables are selectively tensionable to articulate the end effector assembly. In the locked position, the tensions on the cables are maintained to lock the end effector assembly in position.

22 Claims, 64 Drawing Sheets

(51) Int. Cl.
  *A61B 17/29* (2006.01)
  *A61B 19/00* (2006.01)
  *A61B 17/28* (2006.01)

(52) U.S. Cl.
  CPC .......... *A61B 19/22* (2013.01); *A61B 2017/003* (2013.01); *A61B 2017/00314* (2013.01); *A61B 2017/00323* (2013.01); *A61B 2017/00327* (2013.01); *A61B 2017/2837* (2013.01); *A61B 2017/2905* (2013.01); *A61B 2017/291* (2013.01); *A61B 2017/2925* (2013.01); *A61B 2017/2929* (2013.01); *A61B 2017/2936* (2013.01); *A61B 2017/2945* (2013.01); *A61B 2017/2946* (2013.01); *A61B 2018/1422* (2013.01); *A61B 2018/1432* (2013.01)
  USPC ....................................................... 606/205

(56) References Cited

U.S. PATENT DOCUMENTS

| | | | |
|---|---|---|---|
| 2,790,437 A | 4/1957 | Moore | |
| 3,557,780 A | 1/1971 | Sato | |
| 3,858,577 A | 1/1975 | Bass et al. | |
| 3,895,636 A | 7/1975 | Schmidt | |
| 4,483,562 A * | 11/1984 | Schoolman | 294/104 |
| 4,688,554 A | 8/1987 | Habib | |
| 4,728,020 A | 3/1988 | Green et al. | |
| 4,763,669 A | 8/1988 | Jaeger | |
| 4,872,456 A | 10/1989 | Hasson | |
| 4,880,015 A | 11/1989 | Nieman | |
| 4,944,093 A | 7/1990 | Falk | |
| 4,944,741 A | 7/1990 | Hasson | |
| 4,945,920 A | 8/1990 | Clossick | |
| 5,002,543 A | 3/1991 | Bradshasw et al. | |
| 5,042,707 A | 8/1991 | Taheri | |
| 5,209,747 A | 5/1993 | Knoepfler | |
| 5,271,381 A * | 12/1993 | Ailinger et al. | 600/128 |
| 5,273,026 A | 12/1993 | Wilk | |
| 5,275,608 A | 1/1994 | Forman et al. | |
| 5,314,424 A | 5/1994 | Nicholas | |
| 5,330,502 A | 7/1994 | Hassler et al. | |
| 5,344,061 A * | 9/1994 | Crainich | 227/182.1 |
| 5,344,428 A | 9/1994 | Griffiths | |
| 5,383,880 A | 1/1995 | Hooven | |
| 5,386,818 A | 2/1995 | Schneebaum et al. | |
| 5,395,367 A | 3/1995 | Wilk | |
| 5,405,344 A | 4/1995 | Williamson et al. | |
| 5,433,721 A | 7/1995 | Hooven et al. | |
| 5,441,494 A | 8/1995 | Ortiz | |
| 5,454,827 A | 10/1995 | Aust et al. | |
| 5,476,479 A | 12/1995 | Green | |
| 5,501,654 A | 3/1996 | Failla et al. | |
| 5,511,564 A | 4/1996 | Wilk | |
| 5,520,678 A | 5/1996 | Heckele et al. | |
| 5,538,496 A * | 7/1996 | Yabe et al. | 600/141 |
| 5,555,769 A * | 9/1996 | Lichtenberg | 74/89.22 |
| 5,618,294 A | 4/1997 | Aust et al. | |
| 5,643,294 A | 7/1997 | Tovey et al. | |
| 5,702,408 A | 12/1997 | Wales et al. | |
| 5,702,474 A * | 12/1997 | McCandliss | 623/13.12 |
| 5,738,631 A * | 4/1998 | Konstorum | 600/148 |
| 5,759,151 A | 6/1998 | Sturges | |
| 5,766,196 A * | 6/1998 | Griffiths | 606/170 |
| 5,772,578 A * | 6/1998 | Heimberger et al. | 600/139 |
| 5,823,066 A | 10/1998 | Huitema et al. | |
| 5,827,177 A | 10/1998 | Oneda et al. | |
| 5,851,208 A | 12/1998 | Trott | |
| 5,855,569 A | 1/1999 | Komi | |
| 5,873,817 A | 2/1999 | Kokish et al. | |
| 5,891,088 A * | 4/1999 | Thompson et al. | 604/95.04 |
| 5,899,425 A | 5/1999 | Corey Jr. et al. | |
| 5,899,914 A | 5/1999 | Zirps et al. | |
| 5,904,647 A | 5/1999 | Ouchi | |
| 5,916,146 A | 6/1999 | Allotta et al. | |
| 5,916,147 A | 6/1999 | Boury | |
| 5,921,956 A | 7/1999 | Grinberg et al. | |
| 5,938,678 A | 8/1999 | Zirps et al. | |
| 5,944,713 A | 8/1999 | Schuman | |
| 6,126,633 A | 10/2000 | Kaji et al. | |
| 6,174,280 B1 | 1/2001 | Oneda et al. | |
| 6,210,377 B1 | 4/2001 | Ouchi | |
| 6,210,378 B1 | 4/2001 | Ouchi | |
| 6,270,453 B1 | 8/2001 | Sakai | |
| 6,551,238 B2 | 4/2003 | Staud | |
| 6,623,424 B2 | 9/2003 | Hayakawa et al. | |
| 6,638,214 B2 | 10/2003 | Akiba | |
| 6,648,875 B2 * | 11/2003 | Simpson et al. | 604/528 |
| 6,656,195 B2 | 12/2003 | Peters et al. | |
| 6,666,854 B1 | 12/2003 | Lange | |
| 6,752,756 B2 | 6/2004 | Lunsford et al. | |
| 6,761,717 B2 | 7/2004 | Bales et al. | |
| 7,147,650 B2 | 12/2006 | Lee | |
| 7,278,563 B1 | 10/2007 | Green | |
| 7,364,582 B2 | 4/2008 | Lee | |
| 7,615,067 B2 * | 11/2009 | Lee et al. | 606/205 |
| 7,678,117 B2 * | 3/2010 | Hinman et al. | 606/108 |
| 7,945,328 B2 * | 5/2011 | Nideborn Warna et al. | 607/37 |
| 8,100,824 B2 * | 1/2012 | Hegeman et al. | 600/141 |
| 8,241,320 B2 | 8/2012 | Lyons et al. | 606/205 |
| 8,425,408 B2 * | 4/2013 | Boulais et al. | 600/142 |
| 8,465,420 B2 * | 6/2013 | Ostrovsky et al. | 600/141 |
| 8,608,648 B2 * | 12/2013 | Banik et al. | 600/142 |
| 2002/0042607 A1 * | 4/2002 | Palmer et al. | 606/1 |
| 2002/0045803 A1 | 4/2002 | Abe et al. | |
| 2002/0095175 A1 | 7/2002 | Brock et al. | |
| 2002/0133173 A1 | 9/2002 | Brock et al. | |
| 2002/0156497 A1 | 10/2002 | Nagase et al. | |
| 2002/0177750 A1 | 11/2002 | Pilvisto | |
| 2002/0177847 A1 | 11/2002 | Long | |
| 2003/0045900 A1 | 3/2003 | Hahnen et al. | |
| 2003/0065359 A1 | 4/2003 | Weller et al. | |
| 2003/0109898 A1 | 6/2003 | Schwarz et al. | |
| 2003/0135204 A1 | 7/2003 | Lee et al. | |
| 2003/0149338 A1 | 8/2003 | Francois et al. | |
| 2003/0216618 A1 | 11/2003 | Arai | |
| 2004/0049205 A1 | 3/2004 | Lee et al. | |
| 2004/0111009 A1 | 6/2004 | Adams et al. | |
| 2004/0138529 A1 | 7/2004 | Wiltshire et al. | |
| 2004/0158268 A1 | 8/2004 | Danitz | |
| 2004/0176751 A1 | 9/2004 | Weitzner et al. | |
| 2004/0193146 A1 | 9/2004 | Lee et al. | |
| 2004/0236316 A1 | 11/2004 | Danitz et al. | |
| 2005/0049580 A1 | 3/2005 | Brock et al. | |
| 2005/0107667 A1 | 5/2005 | Danitz et al. | |
| 2005/0228440 A1 | 10/2005 | Brock et al. | |
| 2005/0251112 A1 | 11/2005 | Danitz et al. | |
| 2005/0273084 A1 | 12/2005 | Hinman | |
| 2005/0273085 A1 | 12/2005 | Hinman et al. | |
| 2006/0020287 A1 * | 1/2006 | Lee et al. | 606/205 |
| 2006/0069396 A1 | 3/2006 | Meade et al. | |
| 2006/0095076 A1 * | 5/2006 | Elliott et al. | 606/216 |
| 2006/0190034 A1 | 8/2006 | Nishizawa et al. | |
| 2007/0088421 A1 * | 4/2007 | Loewen | 623/1.11 |
| 2007/0118097 A1 * | 5/2007 | Miller | 606/1 |
| 2007/0135803 A1 * | 6/2007 | Belson | 606/1 |
| 2007/0232858 A1 * | 10/2007 | Macnamara et al. | 600/149 |
| 2007/0250113 A1 * | 10/2007 | Hegeman et al. | 606/207 |
| 2009/0118618 A1 * | 5/2009 | Harhen | 600/459 |
| 2009/0240110 A1 * | 9/2009 | Miyawaki et al. | 600/149 |
| 2010/0030018 A1 * | 2/2010 | Fortier et al. | 600/104 |
| 2010/0139661 A1 * | 6/2010 | Landis | 128/205.25 |
| 2010/0192721 A1 * | 8/2010 | Goupil et al. | 74/501.5 R |
| 2011/0160680 A1 * | 6/2011 | Cage et al. | 604/265 |
| 2011/0184459 A1 * | 7/2011 | Malkowski et al. | 606/206 |
| 2012/0095451 A1 * | 4/2012 | Hegeman et al. | 606/1 |
| 2013/0131593 A1 * | 5/2013 | Selkee | 604/95.04 |
| 2014/0121674 A1 * | 5/2014 | Staunton | 606/129 |

FOREIGN PATENT DOCUMENTS

| | | |
|---|---|---|
| EP | 0626604 A2 | 5/1994 |
| EP | 0427949 B1 | 6/1994 |
| EP | 1813203 | 8/2007 |

(56) References Cited

FOREIGN PATENT DOCUMENTS

| GB | 2143920 | 2/1985 |
|---|---|---|
| WO | WO 90/05491 | 5/1990 |
| WO | WO 92/01414 | 2/1992 |
| WO | WO 94/17965 | 8/1994 |
| WO | WO 94/22377 A | 10/1994 |
| WO | WO 2006/113216 | 10/2006 |
| WO | WO 2007/002545 A | 1/2007 |

OTHER PUBLICATIONS

Hiromasa Yamashita et al., "Multi-Slider Linkage Mechanism for Endoscopic Forceps Manipulator," in Proc. of the 2003 IEEE/RSJ, Intl. Conference on Intelligent Robots and Systems, vol. 3, pp. 2577-2582, Las Vegas, Nevada, Oct. 2003.

Multi-DOF Forceps Manipulator System for Laparoscopic Surgery-Mechanism miniaturized & Evaluation of New Interfaces—Nakamura et al.

Multi-DOF Forceps Manipulator System for Laparoscopic Surgery—Nakamura et al.

Development of forceps manipulator system for laparoscopic surgery—Nakamura et al.

European Search Report for EP 09251932.1-2310 dated Dec. 23, 2009, (3 pages).

* cited by examiner

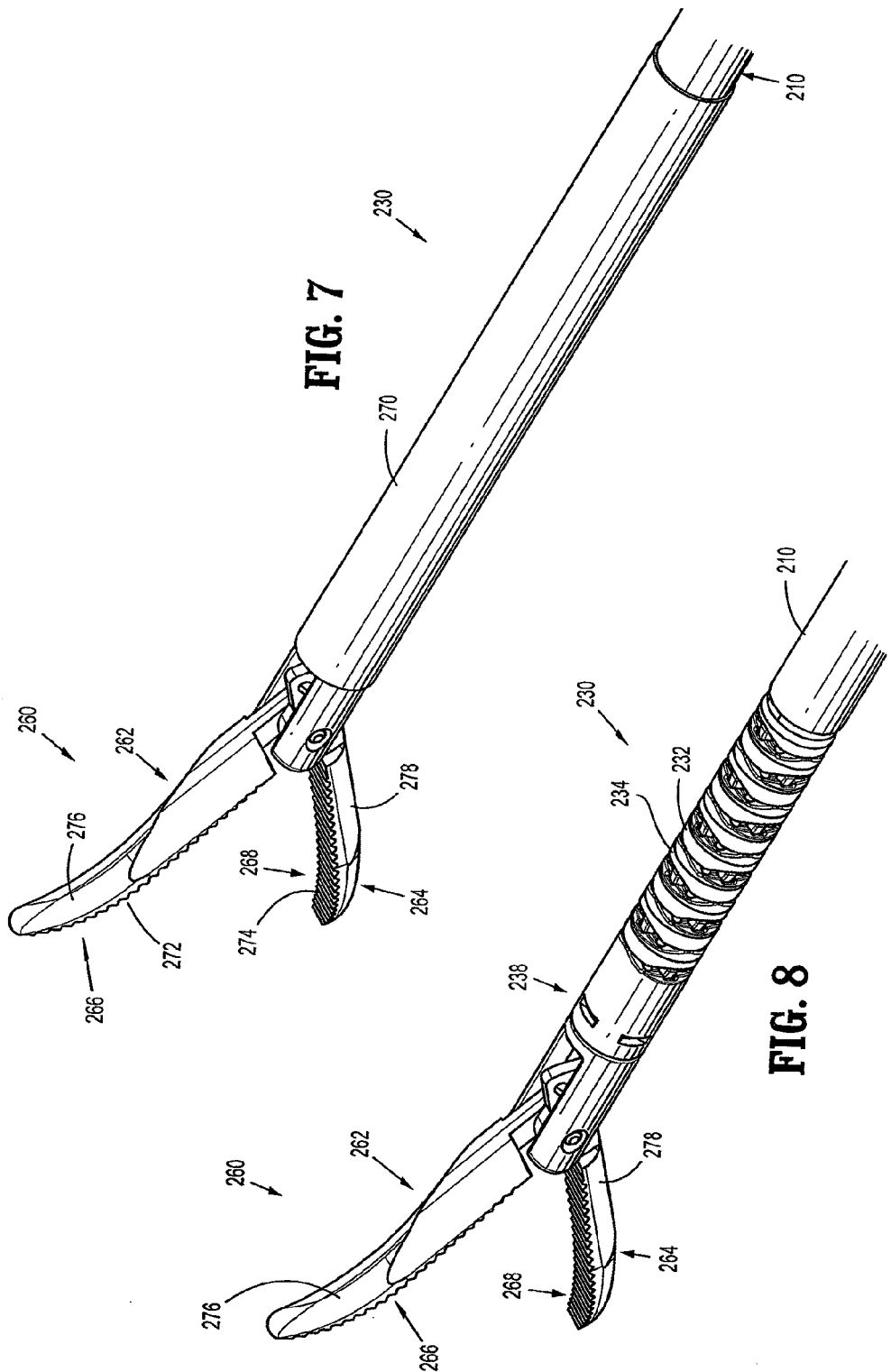

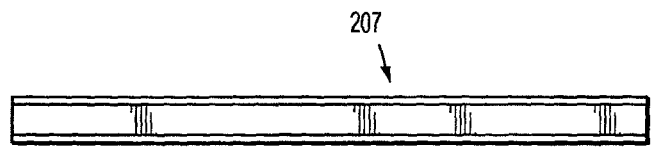
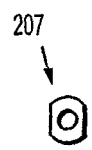
FIG. 10B     FIG. 10C
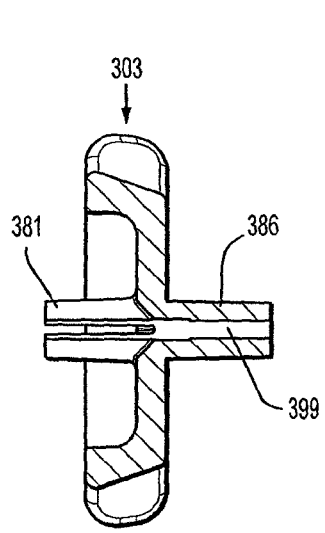
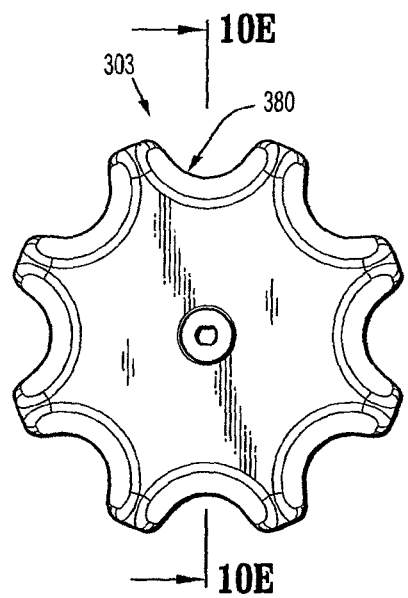
FIG. 10E     FIG. 10D

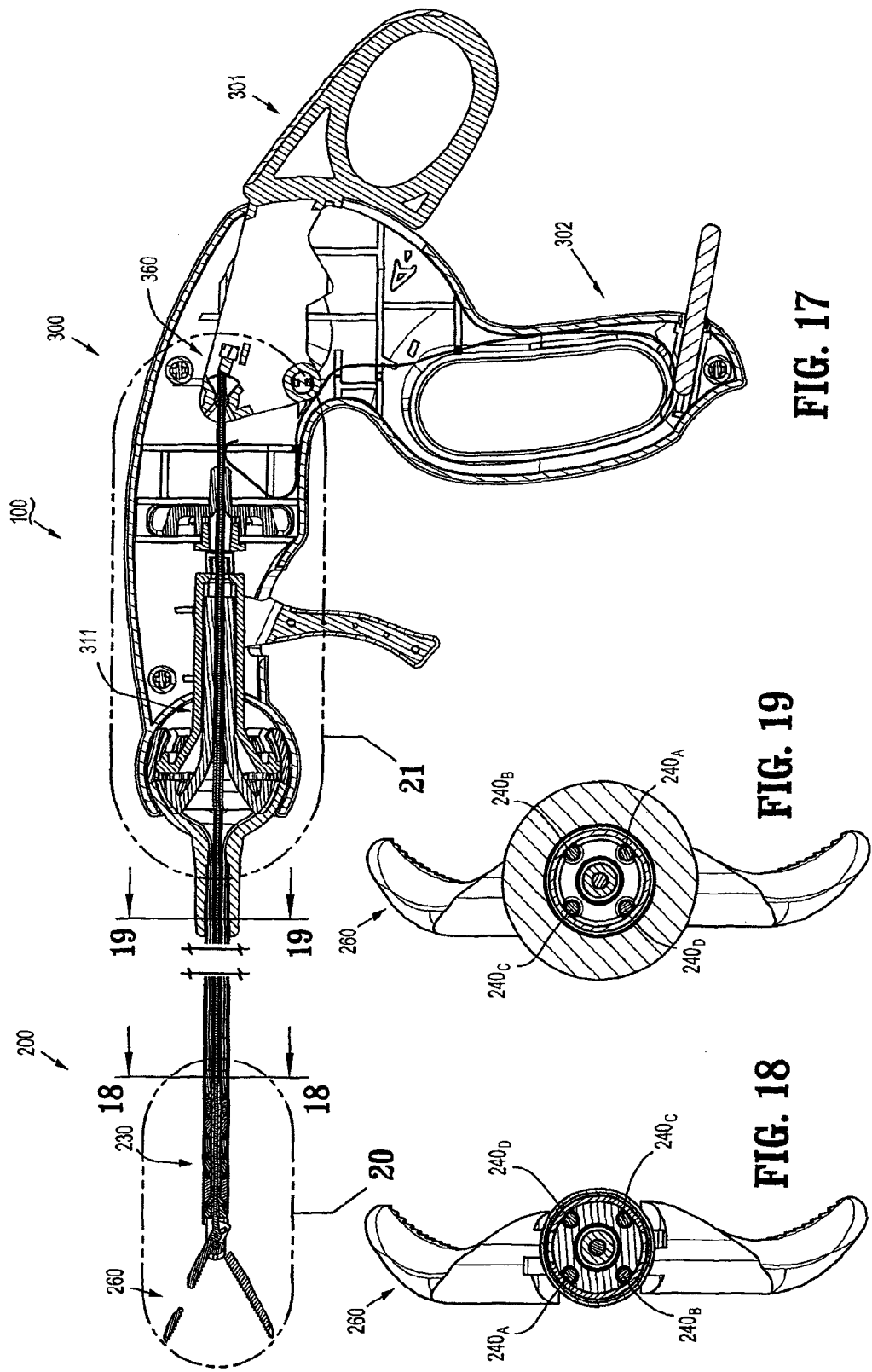

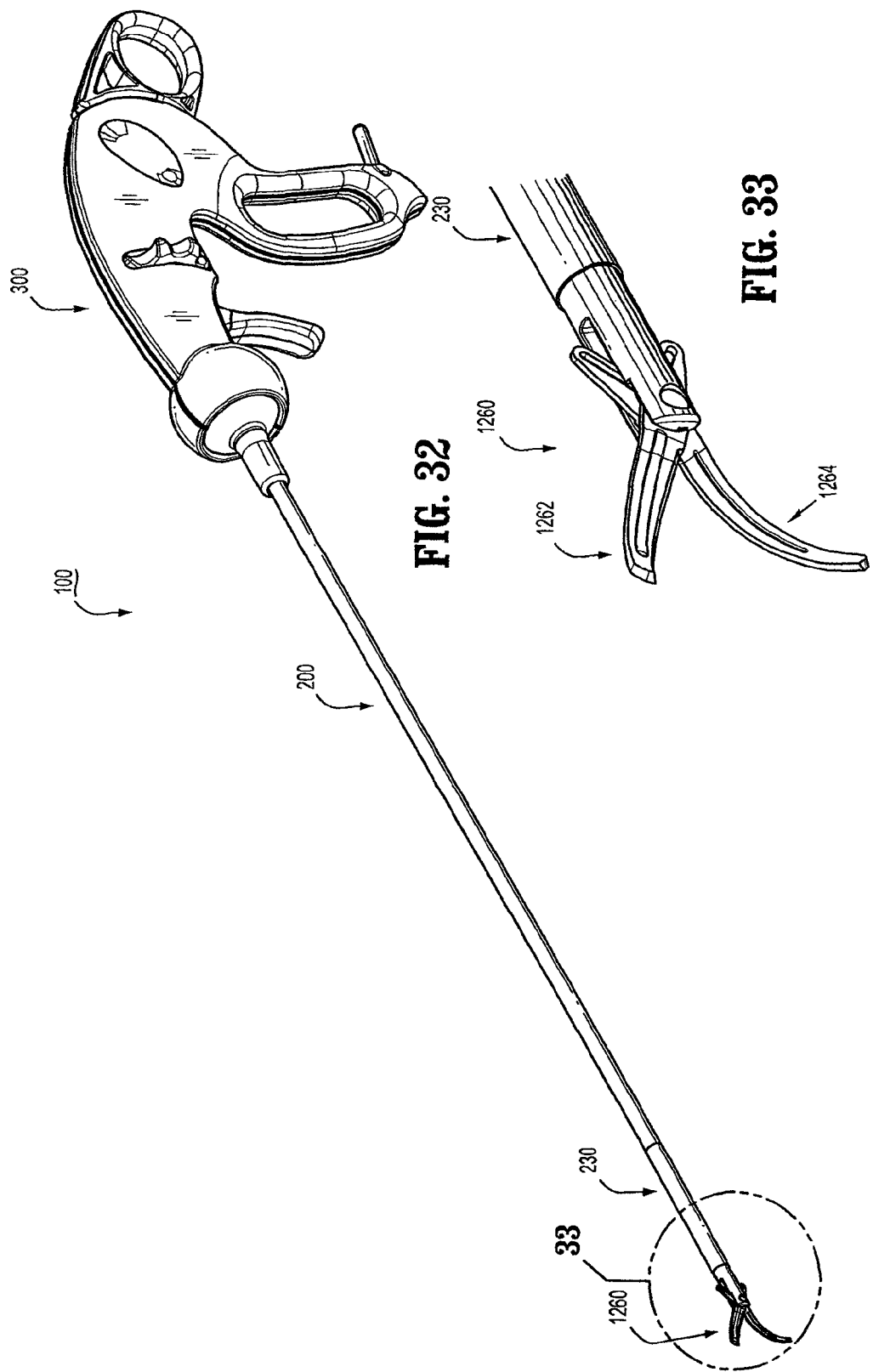

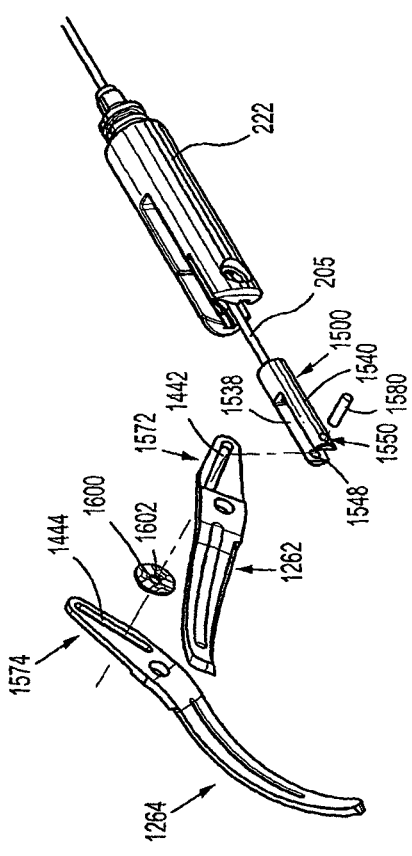
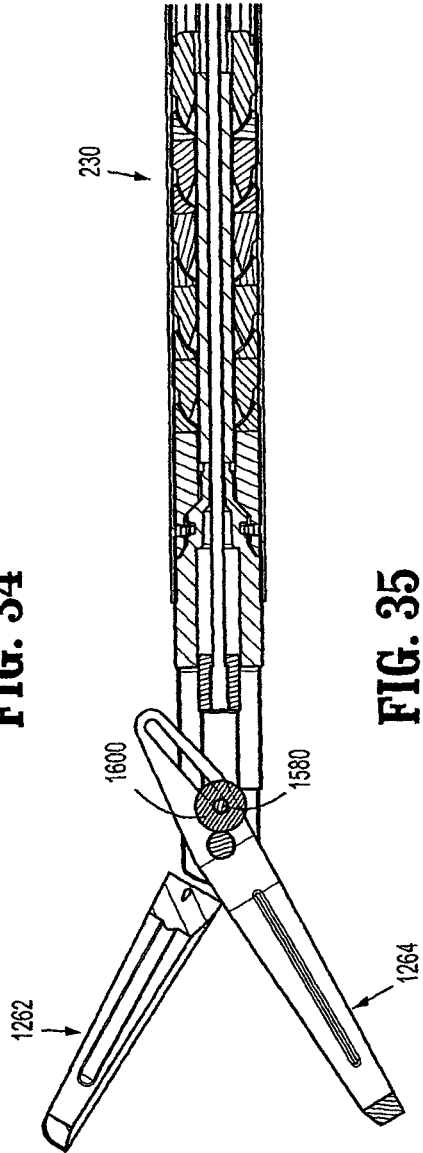
FIG. 34
FIG. 35

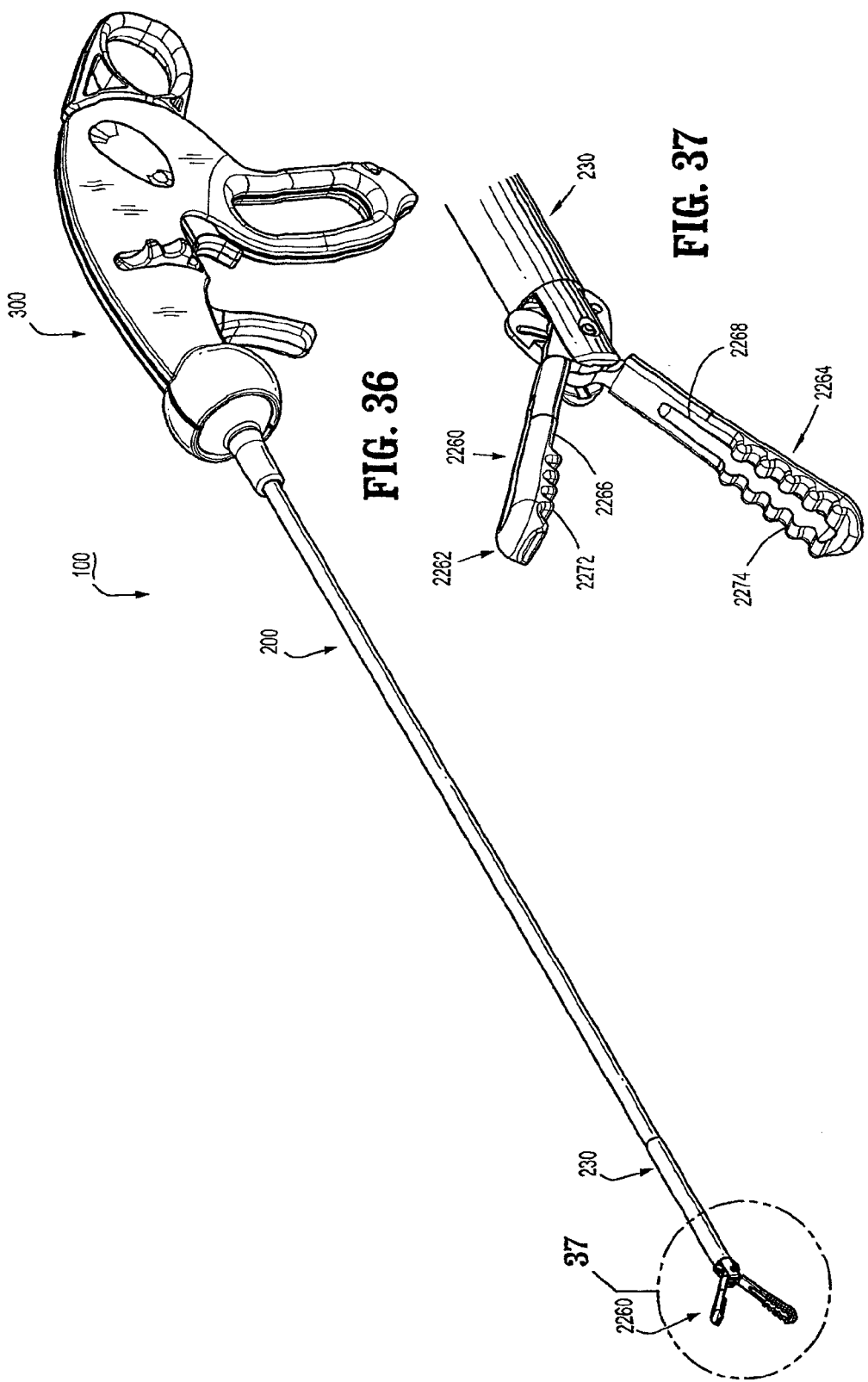

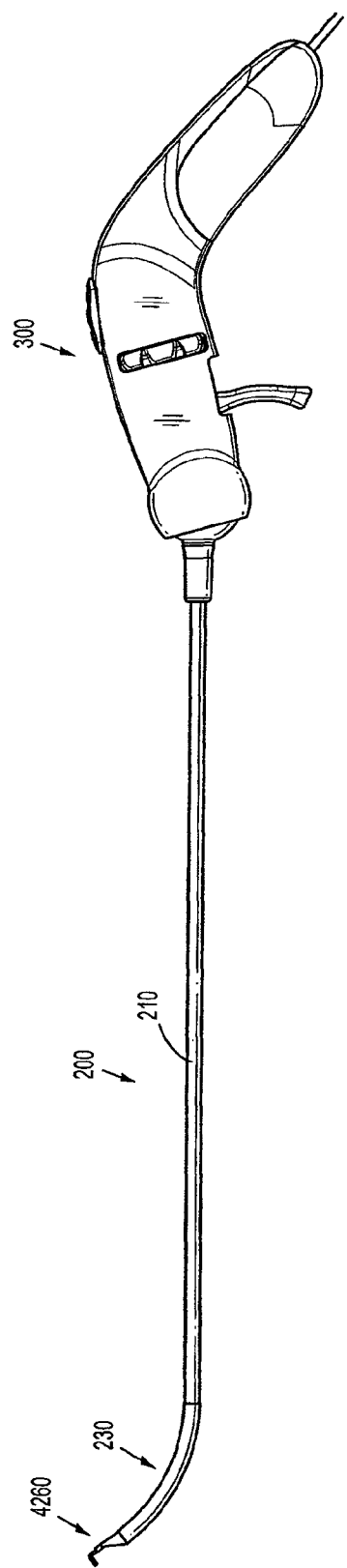
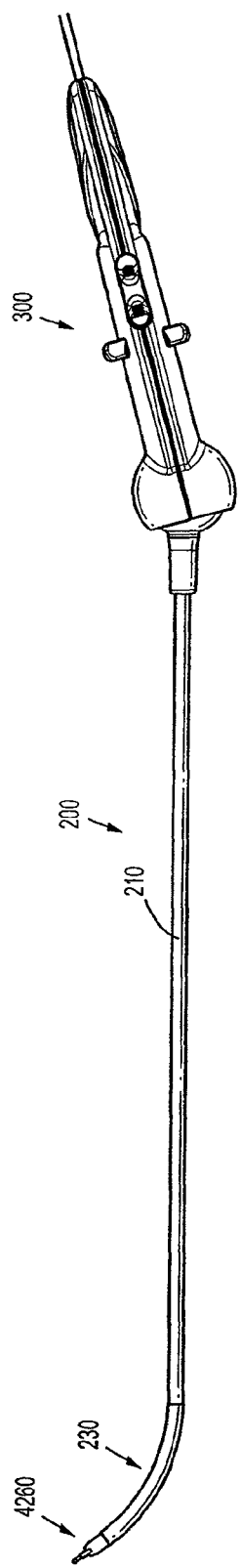
FIG. 48
FIG. 49

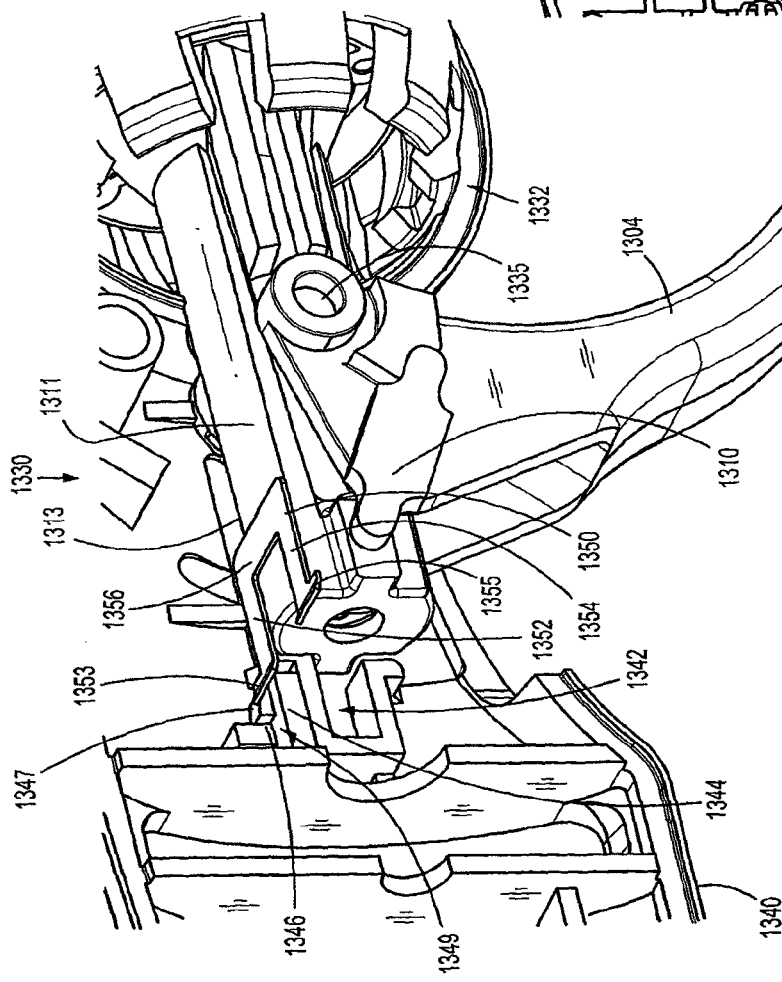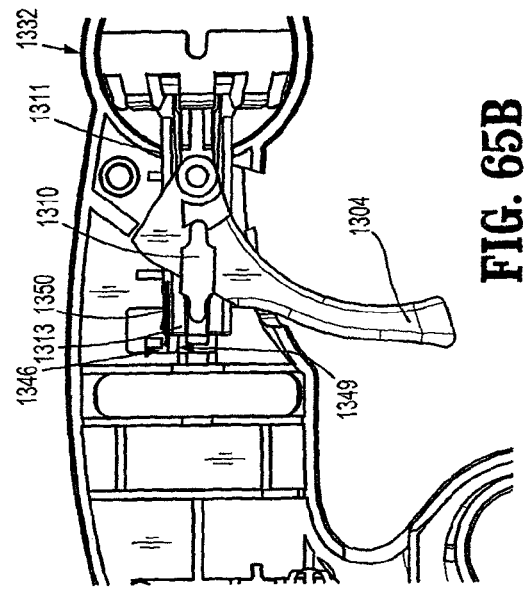
FIG. 65A
FIG. 65B

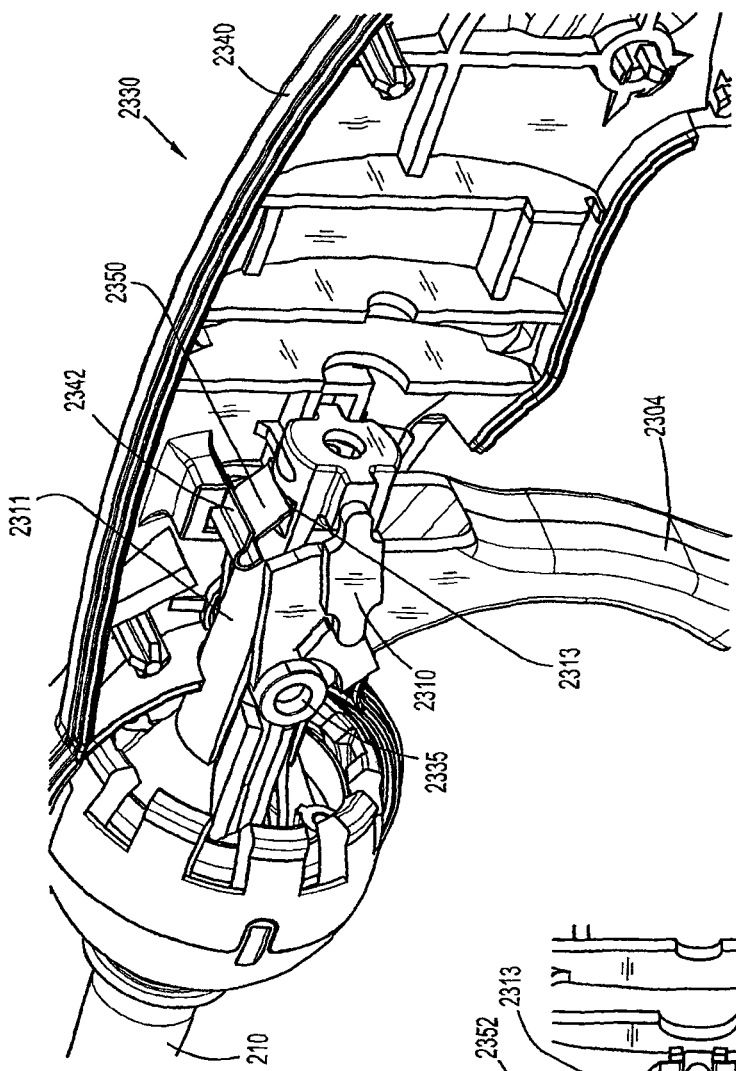
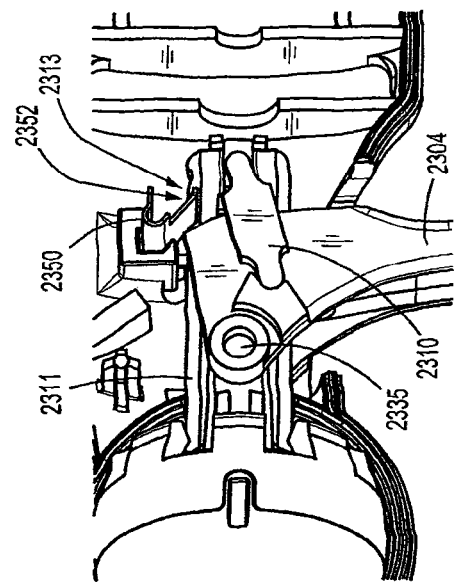
FIG. 66A
FIG. 66B

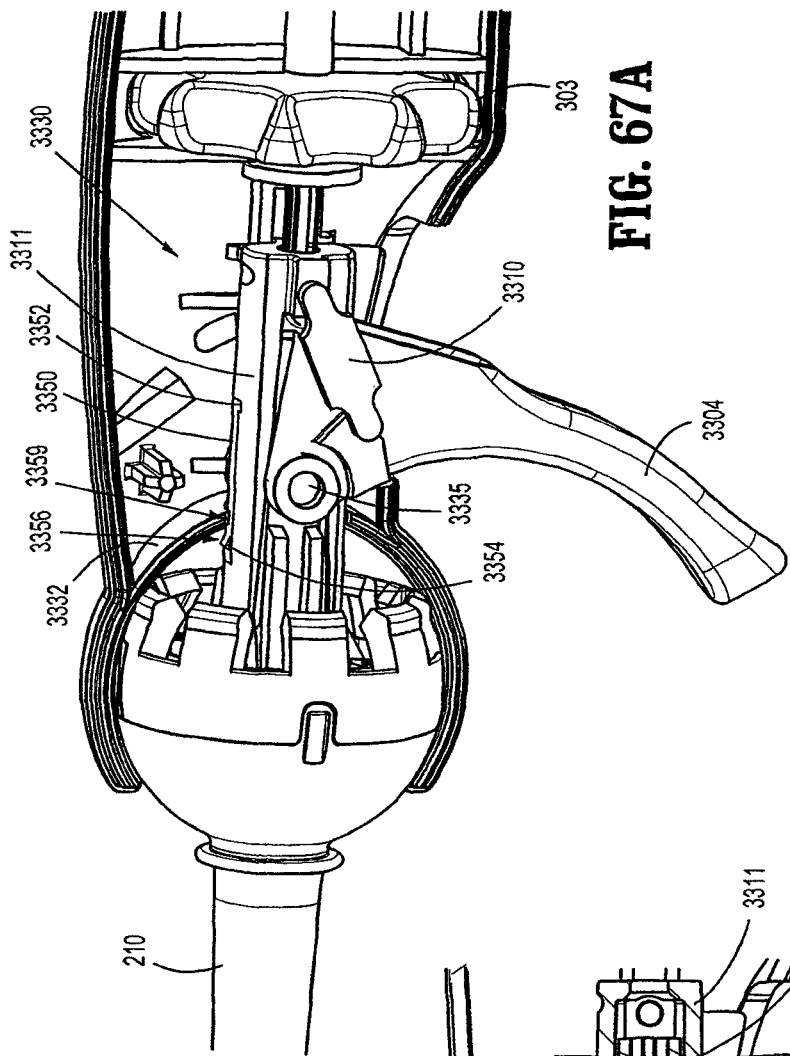
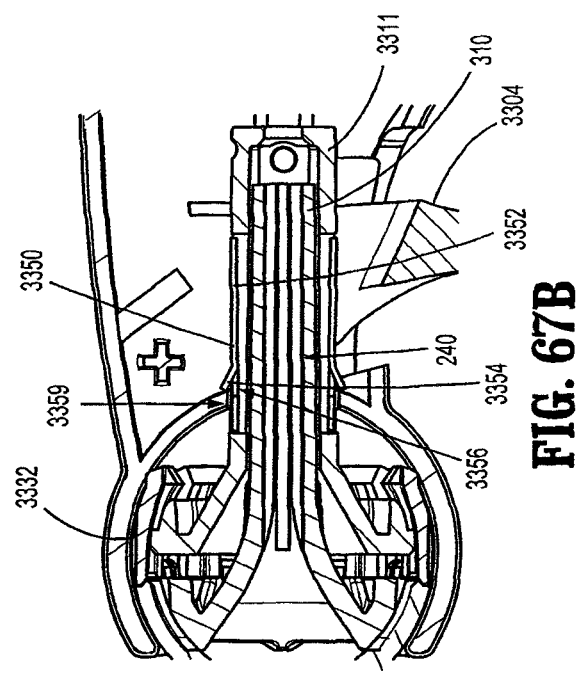
FIG. 67A
FIG. 67B

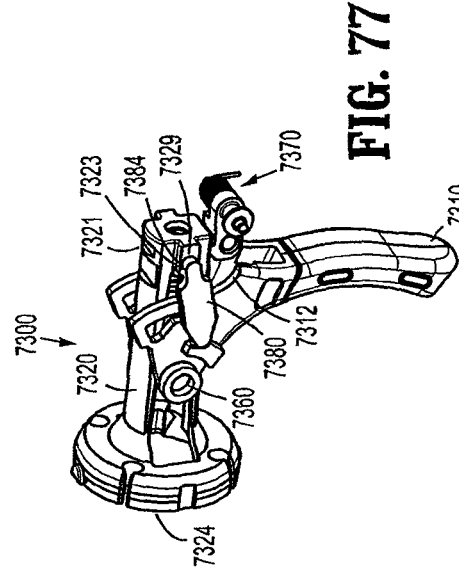
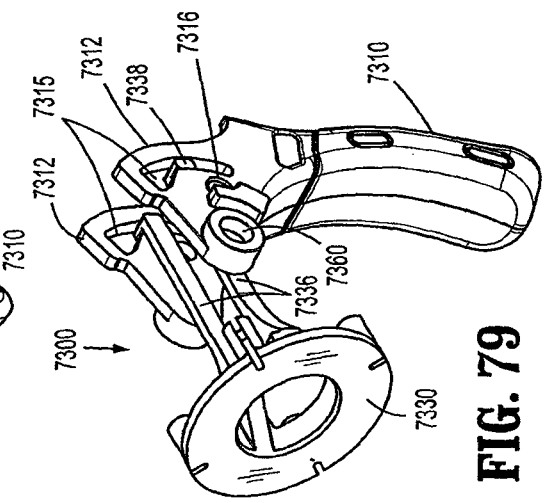
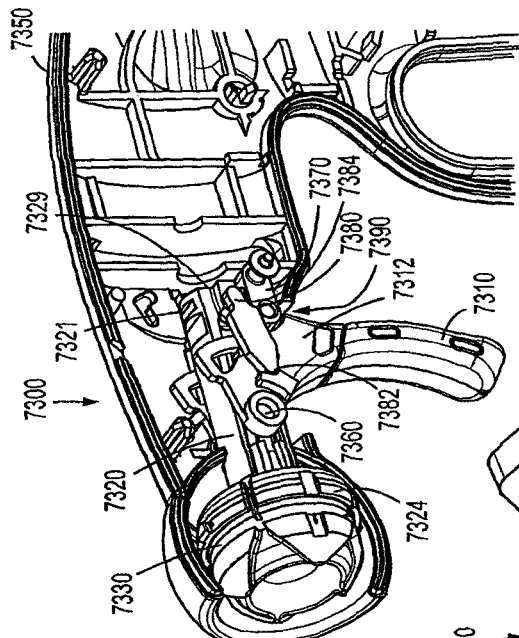
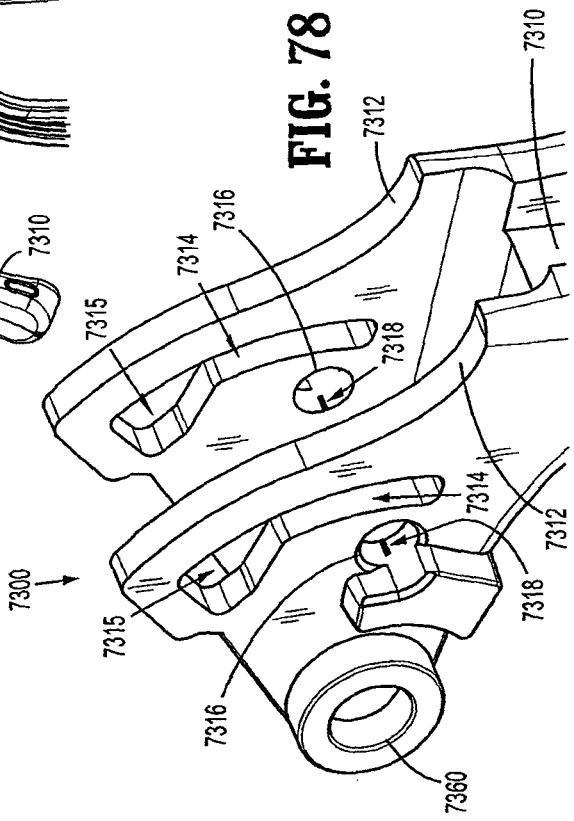

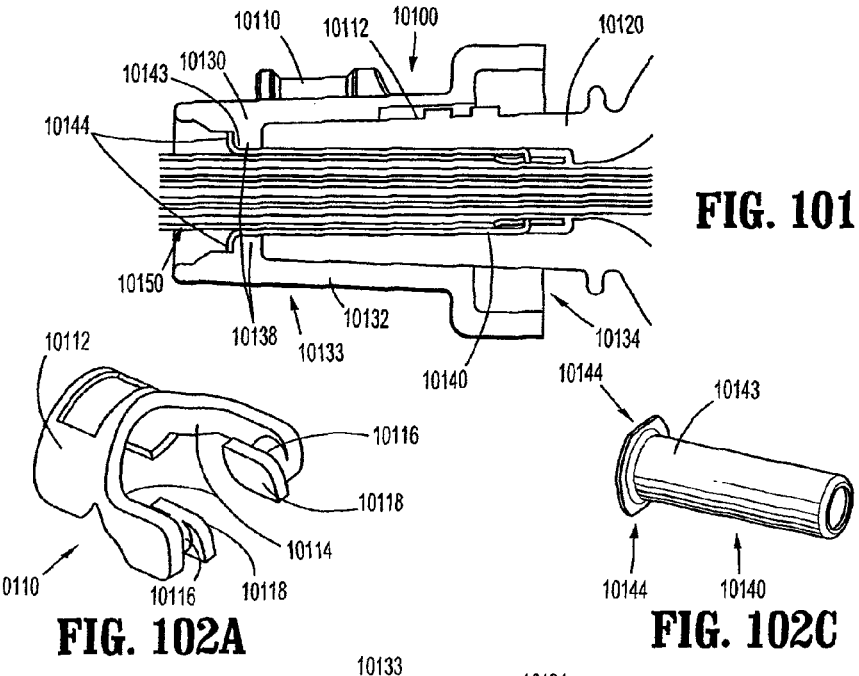
FIG. 101
FIG. 102A
FIG. 102C
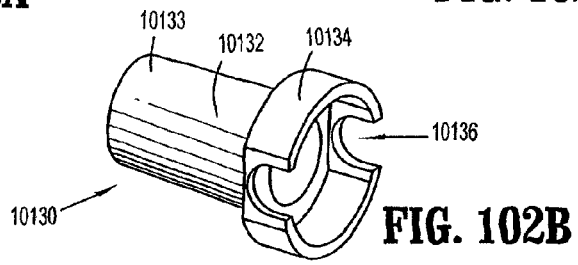
FIG. 102B
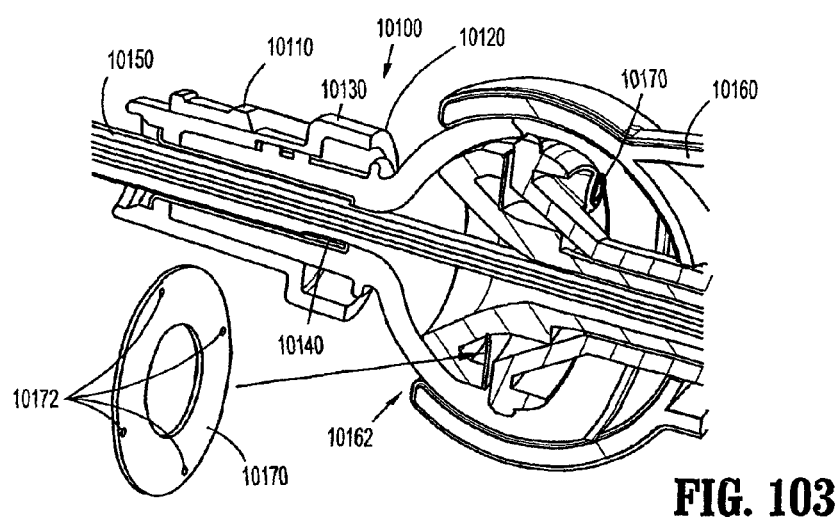
FIG. 103

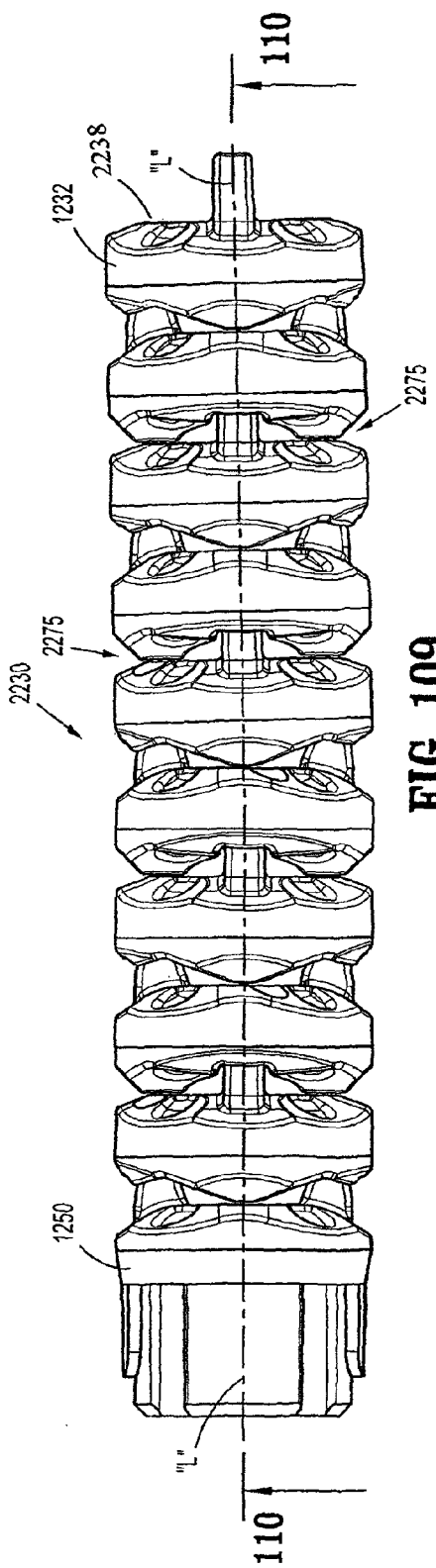
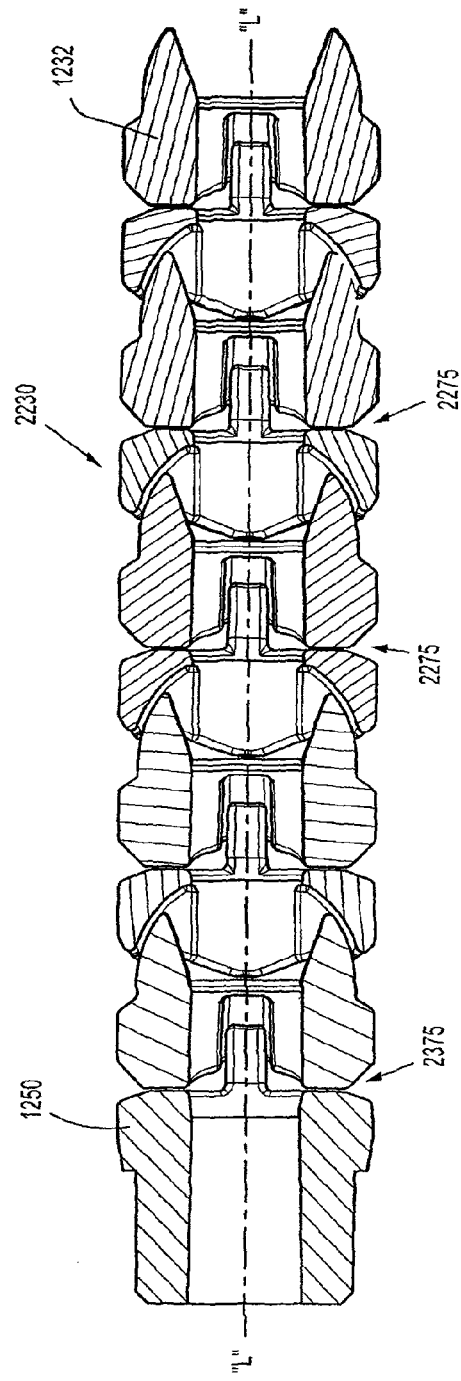
FIG. 109
FIG. 110

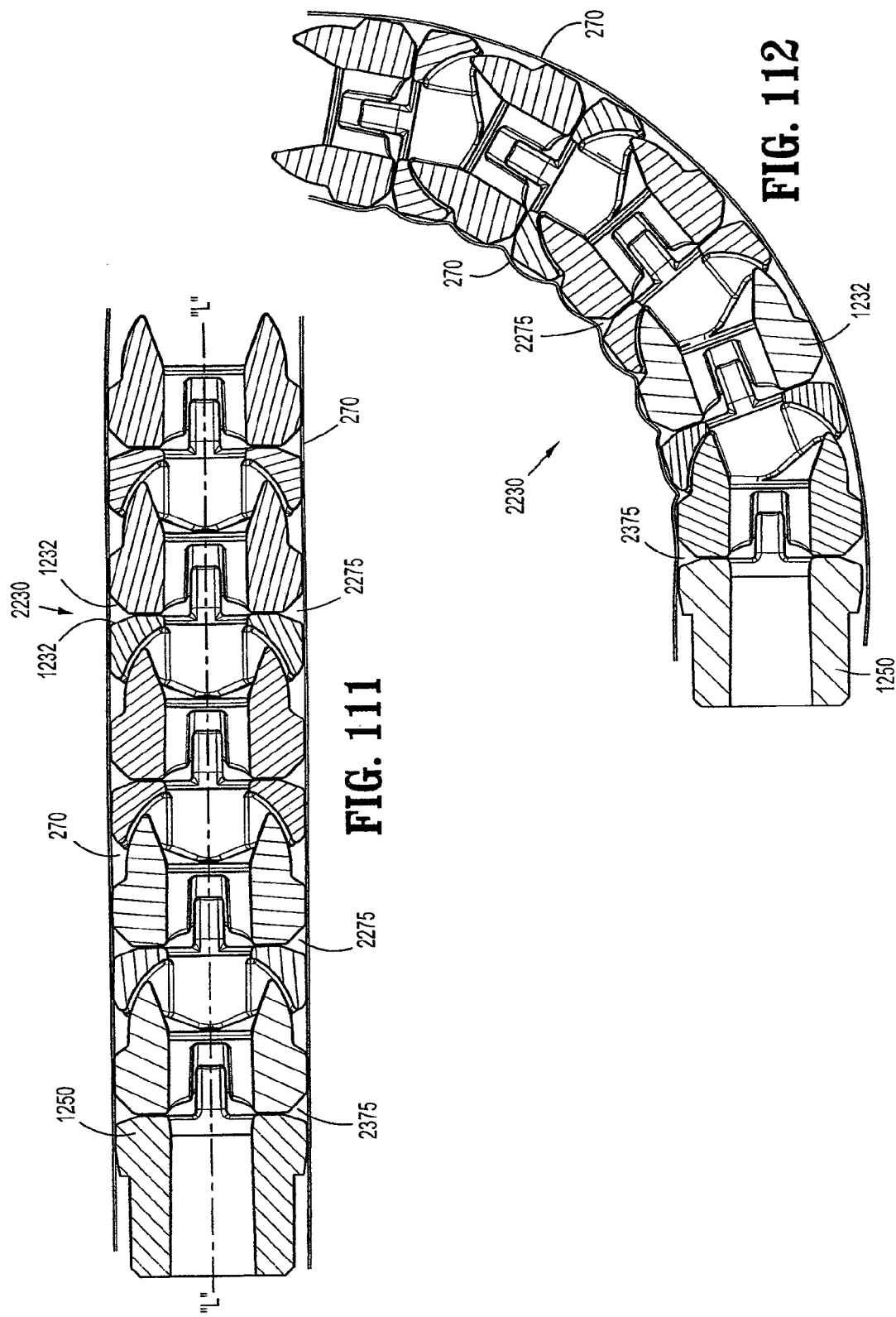

ARTICULATING SURGICAL DEVICE

CROSS-REFERENCE TO RELATED APPLICATION

This application is a Continuation-in-Part Application which claims the benefit of and priority to each of U.S. Provisional Application Ser. No. 61/424,251, filed on Dec. 17, 2010; U.S. Provisional Application Ser. No. 61/316,404, filed on Mar. 23, 2010; and U.S. patent application Ser. No. 12/511,614, filed Jul. 29, 2009, the entire disclosures of each of which is incorporated by reference herein.

U.S. Provisional Application Ser. No. 61/424,251, filed on Dec. 17, 2010, claims the benefit of and priority to U.S. patent application Ser. No. 12/511,614, filed Jul. 29, 2009, the entire disclosures of each of which is incorporated by reference herein.

U.S. Provisional Application Ser. No. 61/316,404, filed on Mar. 23, 2010, claims the benefit of and priority to U.S. patent application Ser. No. 12/511,614, filed Jul. 29, 2009, the entire disclosures of each of which is incorporated by reference herein.

U.S. patent application Ser. No. 12/511,614, filed Jul. 29, 2009, claims the benefit of and priority to U.S. Provisional Application No. 61/085,997, filed on Aug. 4, 2008, the entire disclosures of each of which are incorporated by reference herein.

BACKGROUND

1. Technical Field

The present disclosure relates to endoscopic surgical devices, and more particularly, to endoscopic surgical devices capable of multiple degrees of articulation.

2. Background of the Related Art

Endoscopic surgery is a minimally invasive technique for performing surgery intracorporeally without requiring a large incision. Typically, endoscopic surgery is conducted by inserting a number of ports through small incisions in the patient's skin to access a surgical site. One of the ports receives an endoscope, which is a video camera-like device. The surgeon views the surgical site via the endoscope and performs the surgery by inserting various surgical devices into the patient through the ports. During endoscopic surgery, the surgeon may introduce different surgical devices through the ports. For example, the surgeon may insert a hand operated endoscopic grasper, a dissector, shears, scissors and the like. This technique does not require "opening up" the patient, resulting in less invasive surgery than conventional procedures.

In an effort to reduce the number of incisions required, single incisions procedures and related surgical devices have been developed over the years. For instance, the surgeon may make one incision and maneuver a surgical device through the patient's body until it reaches the desired surgical site. However, it is often challenging to steer a surgical device through the complexities of the human anatomy. In light of this difficulty, a need exist for surgical devices capable of multitude degrees of operation and motion.

SUMMARY

The present disclosure relates to a surgical device capable of multiple degrees of articulation. This surgical device generally includes a handle assembly, an elongate member extending from the handle assembly, an articulation mechanism operatively associated with the handle assembly, and an end effector. The elongate member has an articulating section and straight section. The articulating section is configured to articulate with respect to the straight section. The articulation mechanism is operatively associated with the handle assembly and the articulating section such that the articulating section articulates toward a first direction relative to the straight section upon movement of the handle assembly towards the first direction with respect to the straight section. The end effector is operatively coupled to the articulating section of the elongate member and includes first and second jaw members. The first and second jaw members are configured to move relative to each other between an open position and an approximated position. The surgical device further includes a locking mechanism configured for fixing a relative position of first and second jaw members. The locking mechanism includes a first ratchet assembly and a second ratchet assembly positioned within the handle assembly. The first and second ratchet assemblies are moveable relative to each other between an engaged position to lock the relative position of the first and second jaw members and a disengaged position to unlock the relative position of the first and second jaw members.

In accordance with another embodiment of the present disclosure, there is provided a surgical device for performing surgery including an elongate member defining a longitudinal axis, an articulation section extending from the elongate member, and an end effector operatively coupled to the articulation section. The articulation section is transitionable between a straight position in which the articulation section is aligned with the longitudinal axis and a plurality of articulated positions in which the articulation section is offset from the longitudinal axis. The articulation section includes a plurality of articulation links arranged in a linear fashion. Each articulation link includes chamfered portions such that the chamfered portions of adjacent articulation links are in juxtaposed relation to one another.

In an embodiment, each of the plurality of articulation links may include proximal and distal surfaces, and each surface may include a pair of chamfered portions. The pair of chamfered portions may be defined at an outer periphery of the proximal or distal surface. In addition, the pair of chamfered portions may diametrically oppose each other.

In another embodiment, each articulation link may include at least a pair of bores adapted and dimensioned to receive an articulation cable therein. In addition, each articulation link may further define a channel adapted and dimensioned to receive an actuation cable therethrough for actuation of the end effector.

In yet another embodiment, the surgical device may further include a handle assembly operatively coupled to the articulation section. The articulation cable may interconnect the articulation section with the handle assembly, whereby movement of the handle assembly to angle the handle assembly with respect to the longitudinal axis of the elongate member results in corresponding articulation of the articulation section to an angled position with respect to the longitudinal axis of the elongate member.

In still another embodiment, one of the proximal and distal surfaces of the articulation link may define a pair of recesses. The other one of the proximal and distal surfaces may include a pair of extension members extending axially therefrom. The pair of extension members may be configured and dimensioned to at least partially slidably engage the pair of recesses of an adjacent articulation link.

In still yet another embodiment, the distal surface may include a contoured profile that is configured to mate with a contoured profile of the proximal surface of the adjacent articulation link.

In still yet another embodiment, the surgical device may further include a conformable sheath substantially encasing the articulation section.

BRIEF DESCRIPTION OF THE DRAWINGS

Embodiments of the presently disclosed surgical devices are described herein with reference to the accompanying drawings, wherein:

FIG. 7 is a perspective sectional view of an end effector and the articulating section of the surgical device of FIG. 1, taken around section 7 of FIG. 1 and showing a sheath covering the articulating section of the surgical device;

FIG. 8 is a perspective sectional view of the end effector and the articulating section of the surgical device of FIG. 1, depicting the articulating section without the sheath shown in FIG. 7;

FIG. 10B is a side view of an alignment tube of the surgical device of FIG. 1;

FIG. 10C is a front view of the alignment tube shown in FIG. 10B;

FIG. 10D is a front view of a rotation wheel of the surgical device of FIG. 1;

FIG. 10E is a cross-sectional view of the rotation wheel shown in FIG. 10D, taken along section line 10E-10E of FIG. 10D;

FIG. 17 is a side cross-sectional view of the surgical device of FIG. 1;

FIG. 18 is a rear cross-sectional view of the surgical device of FIG. 1; taken along section line 18-18 of FIG. 17;

FIG. 19 is a rear cross-sectional view of the surgical device of FIG. 1; taken along section line 19-19 of FIG. 17;

FIG. 32 is a perspective view of a surgical device according to another embodiment of the present disclosure, showing an end effector including shearing blades;

FIG. 33 is a perspective view of the end effector and a portion of the articulating section of the surgical device of FIG. 32;

FIG. 34 is a perspective exploded view of the end effector of the surgical device of FIG. 32;

FIG. 35 is a side cross-sectional view of the articulating section and the end effector of the surgical device of FIG. 32;

FIG. 36 is a perspective view of a surgical device according to a further embodiment of the present disclosure, showing an end effector including grasping forceps;

FIG. 37 is a perspective view of the end effector of the surgical device of FIG. 36;

FIG. 48 is a side, elevational view of the surgical device of FIG. 44, depicting the articulating section in an articulated position;

FIG. 49 is a top view of the surgical device of FIG. 44, depicting the articulating section in an articulated position;

FIG. 65A is a rear, perspective cut-away view of one embodiment of an articulation mechanism shown in a shipping position;

FIG. 65B is a side, cut-away view of the articulation mechanism of FIG. 65A shown in a use position;

FIG. 66A is a rear, perspective cut-away view of another embodiment of an articulation mechanism shown in the use position;

FIG. 66B is a front, perspective cut-away view of the articulation mechanism of FIG. 66A shown in the use position;

FIG. 67A is a side, cut-away view of another embodiment of an articulation mechanism shown in the shipping position;

FIG. 67B is a side cross-sectional view of the articulation mechanism of FIG. 67A shown moving toward the use position;

FIG. 76 is a front, perspective cut-away view of yet another embodiment of an articulation mechanism shown transitioning from the shipping position to the use position;

FIG. 77 is an isolated, rear, perspective view of the articulation mechanism of FIG. 76 shown in the use position;

FIG. 78 is an enlarged, rear perspective view of the articulation lock trigger of the articulation mechanism of FIG. 76;

FIG. 79 is an isolated, front, perspective view showing the cable plate and the articulation lock trigger of the articulation mechanism of FIG. 76 coupled to one another;

FIG. 101 is a side, cross-sectional view of a cable tensioning mechanism in accordance with the present disclosure;

FIG. 102A is a rear, perspective view of a cam member of the cable tensioning mechanism of FIG. 101;

FIG. 102B is a rear, perspective view of a pusher of the cable tensioning mechanism of FIG. 101;

FIG. 102C is a rear, perspective view of a ferrule of the cable tensioning mechanism of FIG. 101;

FIG. 103 is a rear, perspective cut-away view of the cable tensioning mechanism of FIG. 101;

FIG. 104 is a front, perspective view of a cable guide rod for use with any of the surgical devices above;

FIG. 105 is a front, perspective view of another embodiment of an articulation linkage for use with the articulating sections of any of the surgical devices above;

FIG. 106 is a rear, perspective view of the articulation linkage of FIG. 105;

FIG. 107 is a front, perspective view of another embodiment of a proximal-most linkage for use with the articulating sections of any of the surgical devices above;

FIG. 108 is a rear, perspective view of the proximal-most articulation linkage of FIG. 107;

FIG. 109 is a side, elevational view of an articulation section including a plurality of articulation links as illustrated in FIG. 105 and a proximal-most link as illustrated in FIG. 107;

FIG. 110 is a longitudinal, cross-sectional view of the articulation section of FIG. 109 taken along section line 110-110 of FIG. 109;

FIG. 111 is a longitudinal, cross-sectional view of the articulation section of FIG. 109 shown encased with a sheath; and FIG. 112 is a cross-sectional view of the articulation section of FIG. 111 shown in an articulated position.

DETAILED DESCRIPTION OF THE EMBODIMENTS

Figure 1:
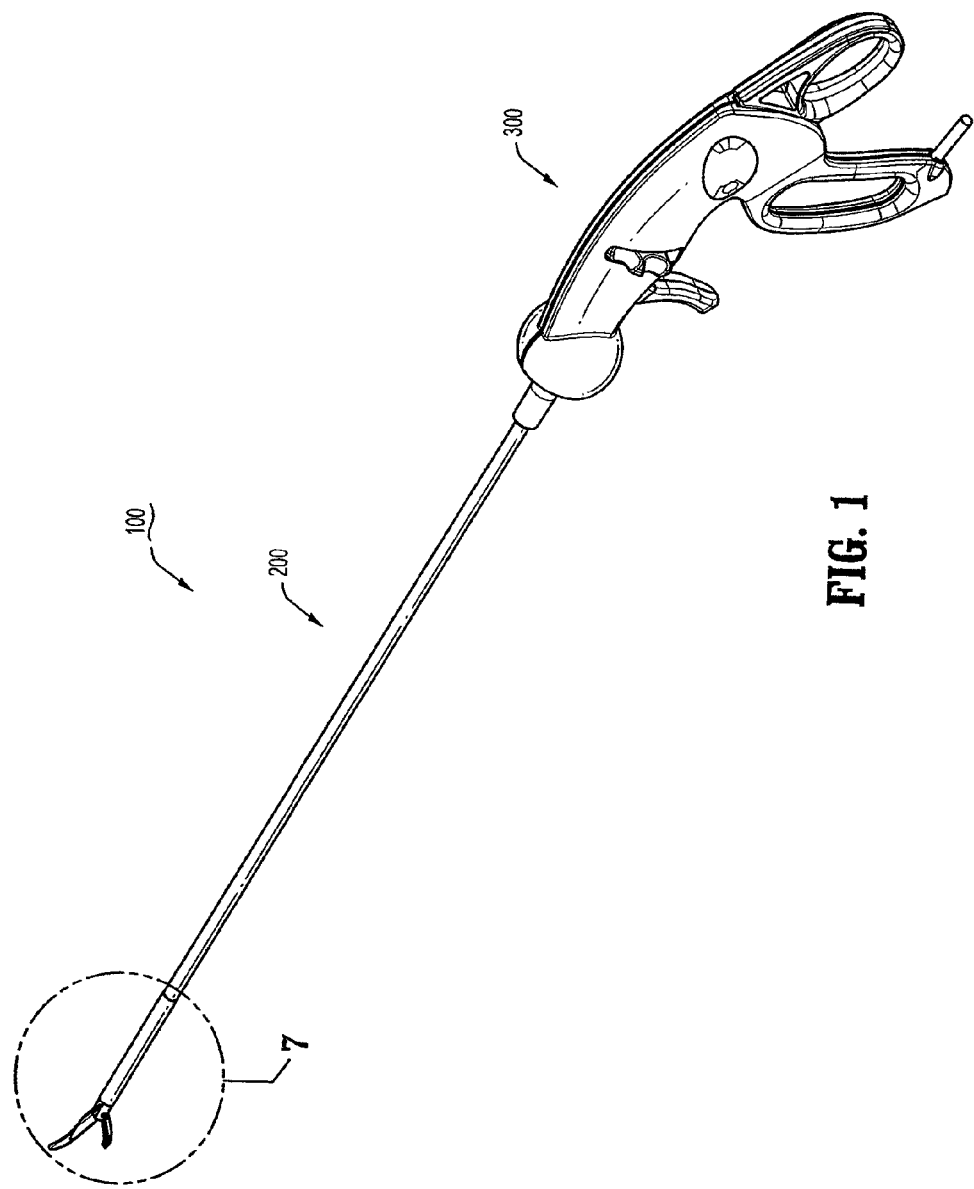
FIG. 1 is a rear, perspective view of a surgical device according to an embodiment of the present disclosure.

Embodiments of the presently disclosed surgical device are described in detail with reference to the drawings, in which like reference numerals designate identical or corresponding elements in each of the several views. As used herein the term "distal" refers to that portion of the surgical device, or component thereof, farther from the user, while the term "proximal" refers to that portion of the surgical device, or component thereof, closer to the user.

FIG. 1 illustrates an endoscopic surgical device designated with reference number 100. Surgical device 100 generally includes a handle assembly 300 and an endoscopic assembly 200 extending distally from handle assembly 300. Handle assembly 300 is configured to move relative to endoscopic assembly 200. Endoscopic assembly 200 has an elongate configuration and is operatively associated with handle assembly 300. In some embodiments, handle assembly 300 can be held and operated with only one hand.

As seen in FIGS. 2-6, endoscopic assembly 200 includes an elongate outer tube 210 having a proximal end 212 and a distal end 214. Proximal end 212 of elongate outer tube 210 is secured to handle assembly 300. In the embodiment shown in FIG. 2, elongate outer tube 210 has a straight configuration and defines a longitudinal axis "X" therealong; however, elongate outer tube 210 may have a curved configuration. In some embodiments, elongate outer tube 210 is made wholly or partly from a substantially rigid or stiff biocompatible material such as polyetheretherketone (PEEK), titanium alloy, aluminum alloy, stainless steel, cobalt chromium alloy, or any combination thereof.

With continued reference to FIGS. 2-6, endoscopic assembly 200 further includes an articulating section 230 supported on distal end 214 of elongate outer tube 210. Articulating section 230 has a proximal end 236 and a distal end 238 and is configured to articulate towards a particular direction with respect to elongate outer tube 210 upon movement of handle assembly 300 towards the same direction with respect to elongate outer tube 210.

Figure 2:
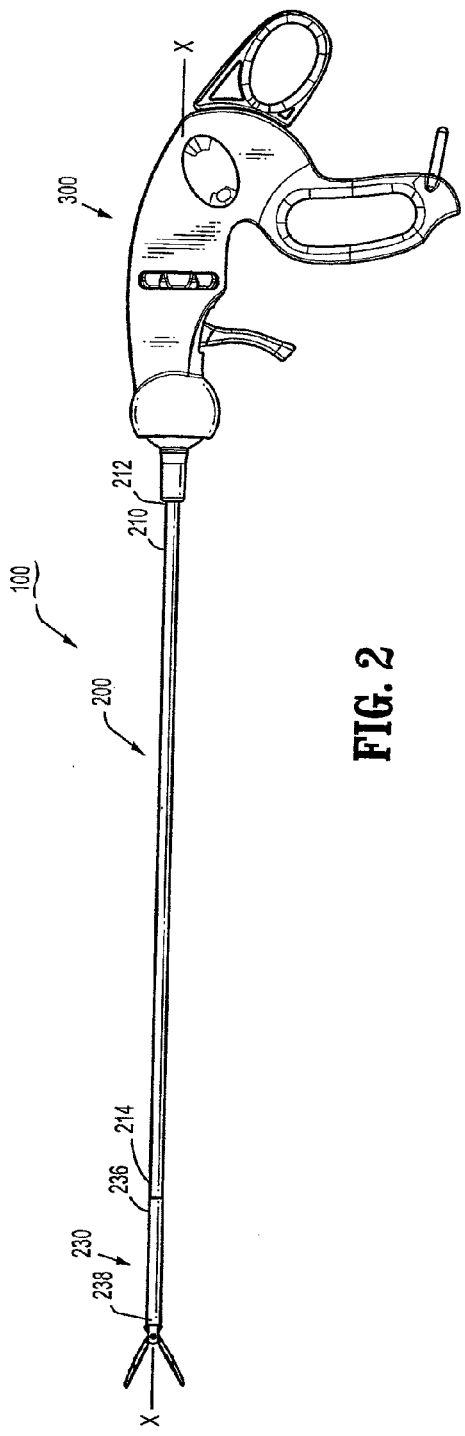
FIG. 2 is a side, elevational view of the surgical device of FIG. 1 with an articulating section in a straight position.
Figure 3:
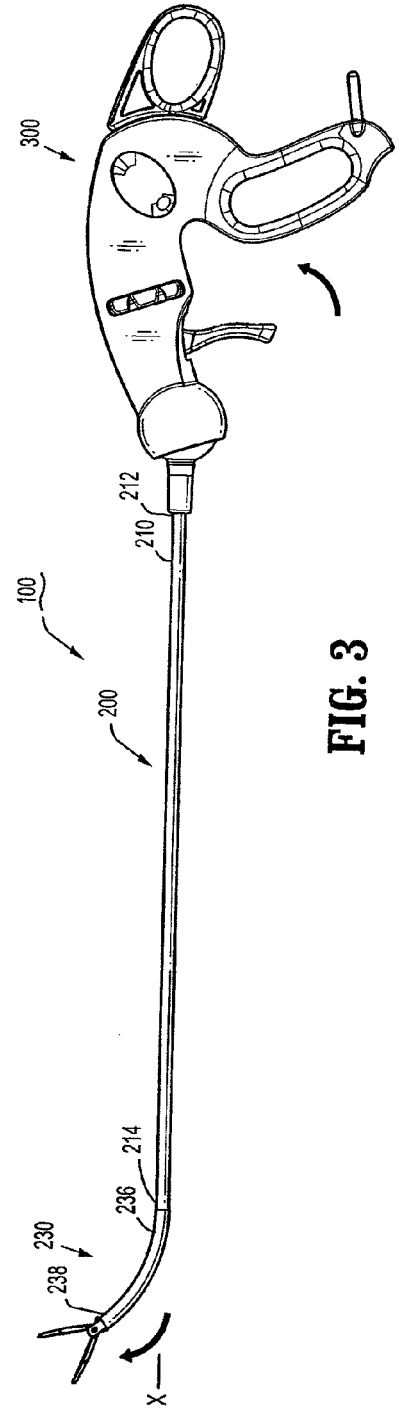
FIG. 3 is a side, elevation view of the surgical device of FIG. 1 with the articulating section in an articulated position.
Figure 4:
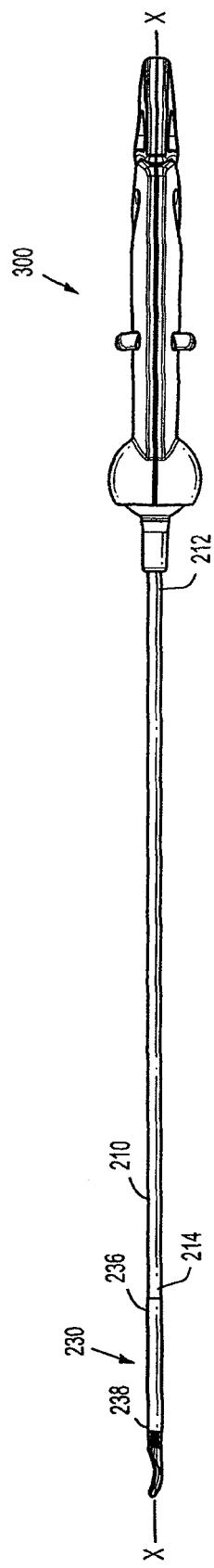
FIG. 4 is a top view of the surgical device of FIG. 1 with the articulating section in a straight position.
Figure 5:
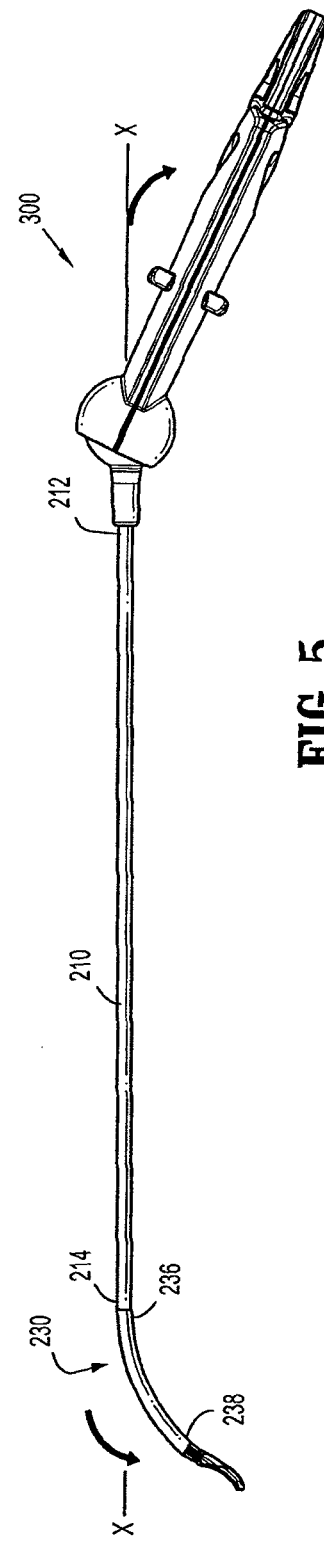
FIG. 5 is a top view of the surgical device of FIG. 1 with the articulating section in an articulated position.

Elongate outer tube 210 and articulating section 230 are longitudinally aligned with each other when handle assembly 300 is positioned in a neutral position, as seen in FIGS. 2 and 4. When handle assembly 300 is moved relative to elongate outer tube 210 toward one direction, articulating section 230 articulates toward the same direction. For example, an operator can move handle assembly 300 upwardly relative to elongate outer tube 210 to articulate articulating section 230 upwardly relative to elongate outer tube 210, as depicted in FIG. 3. In addition to this upward motion, the operator can move handle assembly 300 laterally with respect to elongate outer tube 210 to articulate articulating section 230 laterally relative to elongate outer tube 210, as illustrated in FIG. 5. Although the drawings merely show upward and lateral movements of articulating section 230, articulating section 230 has multitude of degrees of motion. Irrespective of the specific degrees of motion, the movement of articulating section 230 relative to elongate outer tube 210 mirrors the motion of handle assembly 300 with respect to elongate outer tube 210.

Figure 6:
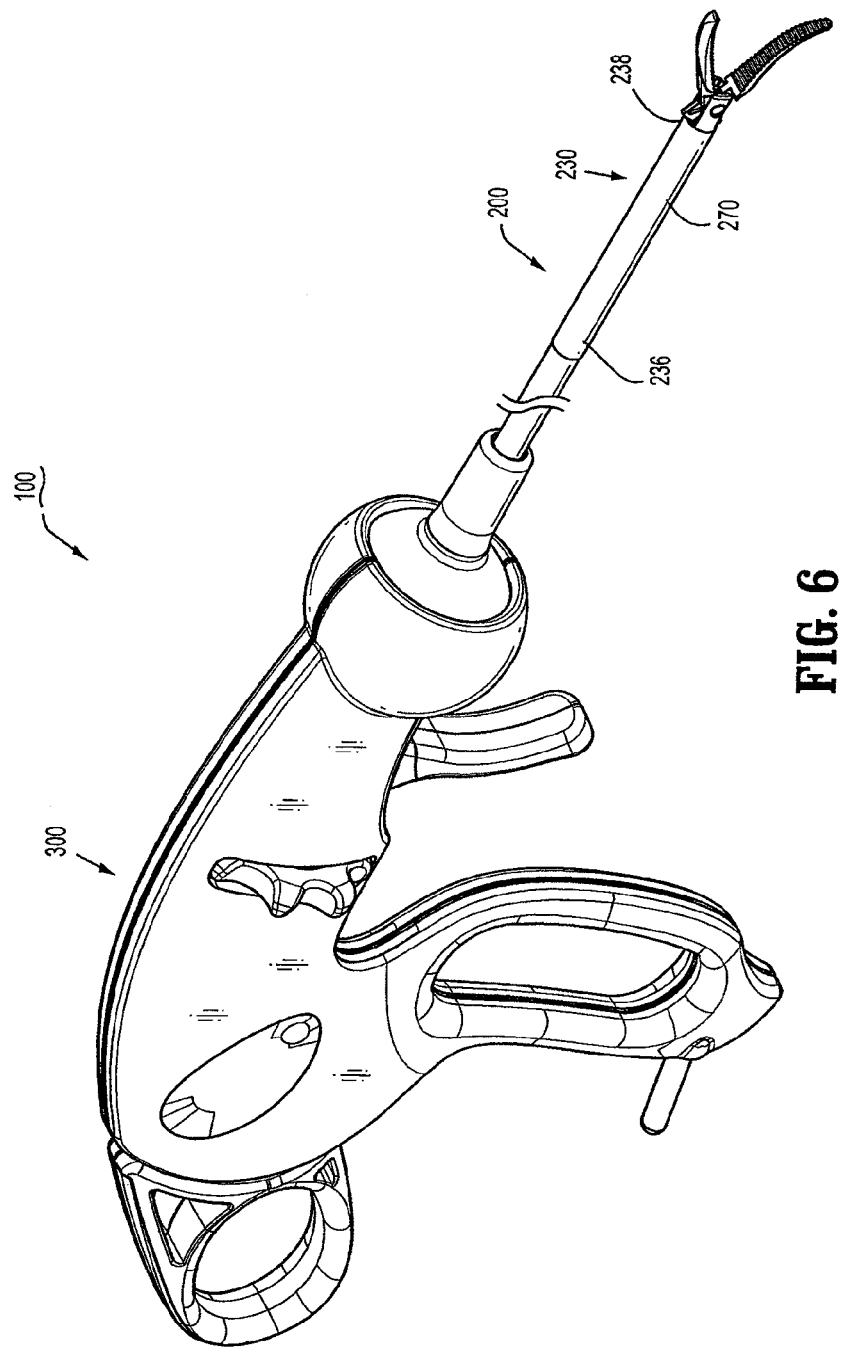
FIG. 6 is a front, perspective view of the surgical device of FIG. 1.

With reference to FIGS. 6-8, endoscopic assembly 200 further includes a tool assembly or end effector 260 operatively coupled to distal end 238 of articulating section 230. In certain embodiments, articulating section 230 includes a sheath 270 covering at least a portion of articulating section 230. Sheath 270 is made (wholly or partly) of any suitable flexible material. In some embodiments, sheath 270 is made of a biocompatible polymer. Other embodiments of surgical device 100 do not include sheath 270. Articulating section 230 additionally includes at least two articulation links 232, 234 configured for pivotable movement relative to each other. However, articulating section 230 may include more articulation links. In the depicted embodiment, articulation section 230 includes ten (10) articulation links 232, 234. It is understood that a greater number of articulation links 232, 234 provides articulating section 230 with more degrees of articulation. Regardless of the exact number of articulation links 232, 234, articulation links 232, 234 allows articulating section 230 to articulate relative to elongate outer tube 210. In particular, articulating section 230 can move from a first position longitudinally aligned with elongate outer tube 210 to a myriad of positions that are not longitudinally aligned with elongate outer tube 210.

As discussed above, articulating section 230 is operatively associated with end effector 260. Although the drawings show a specific kind of end effector 260, it is envisioned that surgical device 100 may include any end effector suitable for engaging tissue. For example, an embodiment of surgical device 100 includes the end effector described in U.S. Patent Application Publication Serial No. 2009/0012520, filed on Sep. 19, 2008, which entire contents are herein incorporated by reference.

End effector 260 includes a first jaw member 262 and a second jaw member 264 pivotally coupled to each other. First and second jaw members 262, 264 are configured to move from a first or open position to a second or approximated position. In the first position, first and second jaw members 262, 264 are spaced apart from each other and can receive tissue between them (see FIGS. 7 and 8). In the second position, first and second jaw members 262, 264 are approximated to each other and can grasp or clamp any tissue positioned between them (see FIG. 31).

Each of first and second jaw members 262, 264 includes a tissue engaging surface 266, 268 and a housing 276, 278. Tissue engaging surfaces 266, 268 each include teeth 272, 274 extending along their lengths. Teeth 272, 274 aid in grasping tissue located between first and second jaw members 262, 264 when first and second jaw members 262, 264 are located in the approximated position.

In some embodiments, tissue engaging surfaces 266, 268 are made of an electrically conductive material and housings 276, 278 are formed of an electrical insulating material. As such, tissue engaging surfaces 266, 268 are adapted to receive electrosurgical energy and conduct electrosurgical energy to the tissue grasped between first and second jaw members 262, 264. First and second jaw members 262, 264 are electrically isolated from each other and form a bipolar arrangement. This electrical arrangement allows first and second jaw members 262, 264 to effectively transfer electrical energy through tissue. In a bipolar arrangement, the electrical current travels from one tissue engaging surface (266 or 268) to another tissue engaging surface (266 or 268) through the grasped tissue to complete the circuit. In an alternate embodiment, surgical device 100 has a monopolar electrical arrangement. In this embodiment, end effector 260 transmits electrosurgical energy to the tissue grasped between first and second jaw members 262, 264 and this electrosurgical energy passes through the patient's body until it reaches a patient return electrode (not shown) to complete the circuit. This patient return electrode is electrically coupled to surgical device 100. The user may control the intensity, frequency and duration of the electrosurgical energy applied to the tissue to cauterize, dissect, coagulate, desiccate, seal, and/or simply reduce or slow bleeding during a medical procedure. The electrosurgical energy received by first and second jaw members 262, 264 originates from an electrosurgical generator (not shown) or any other suitable source of electrosurgical energy. In certain embodiments, surgical device 100 is electrically coupled to an electrosurgical generator including a high voltage direct current (HVDC) power supply configured for supplying a DC voltage, an output filter for smoothing the switching of the HVDC into a DC level, and a radio frequency (RF) output stage coupled to the HVDC and configured to convert the DC energy generated by the HVDC into RF energy. In some embodiments, surgical device 100 is electrically coupled to the electrosurgical generator described in U.S. Pat. No. RE40,388, filed on May 8, 2003, the entire contents of which are hereby incorporated by reference.

Figure 9:
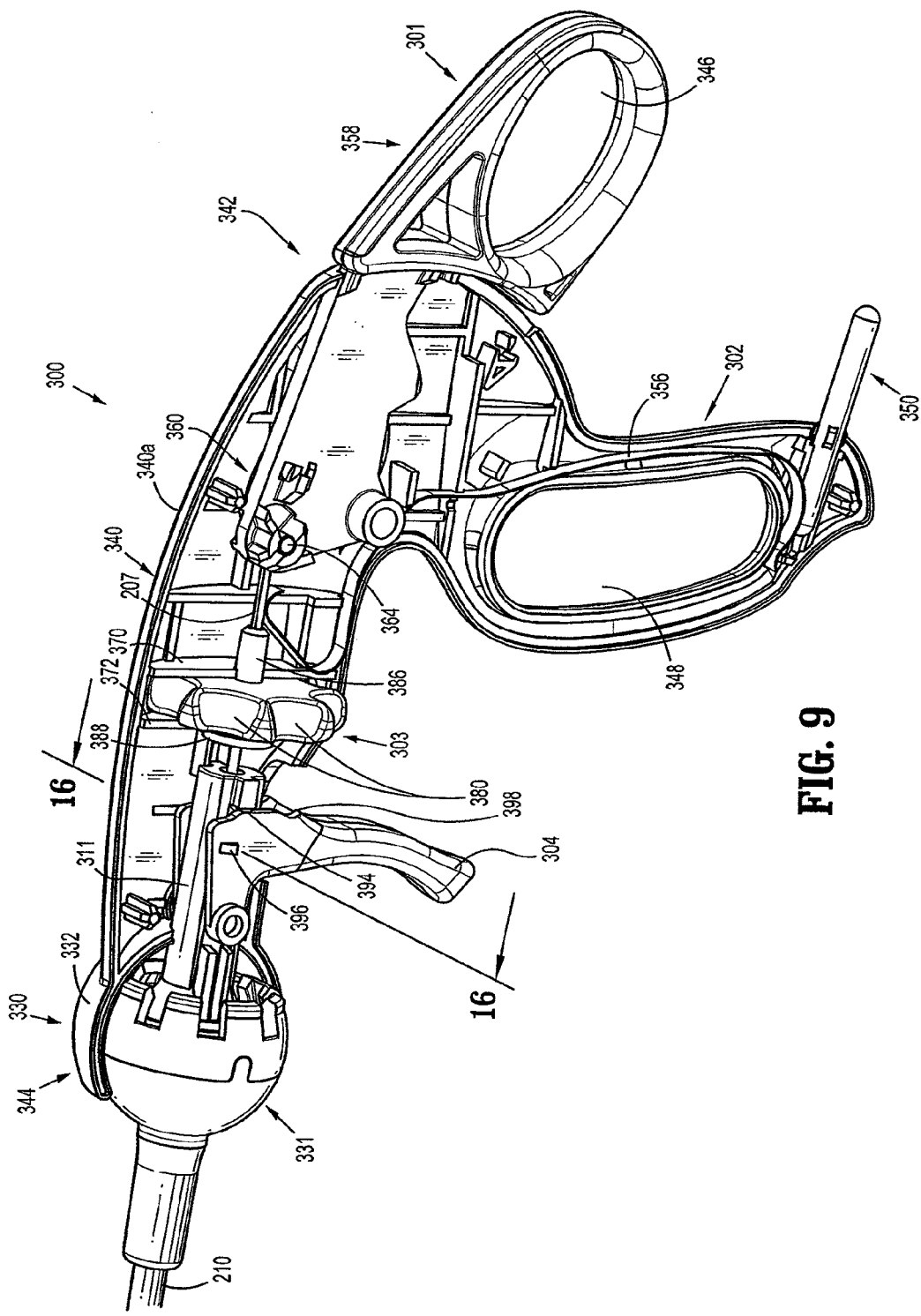
FIG. 9 is a perspective cutaway view of a handle assembly of the surgical device of FIG. 1, showing the internal components of the handle assembly.
Figure 10A:
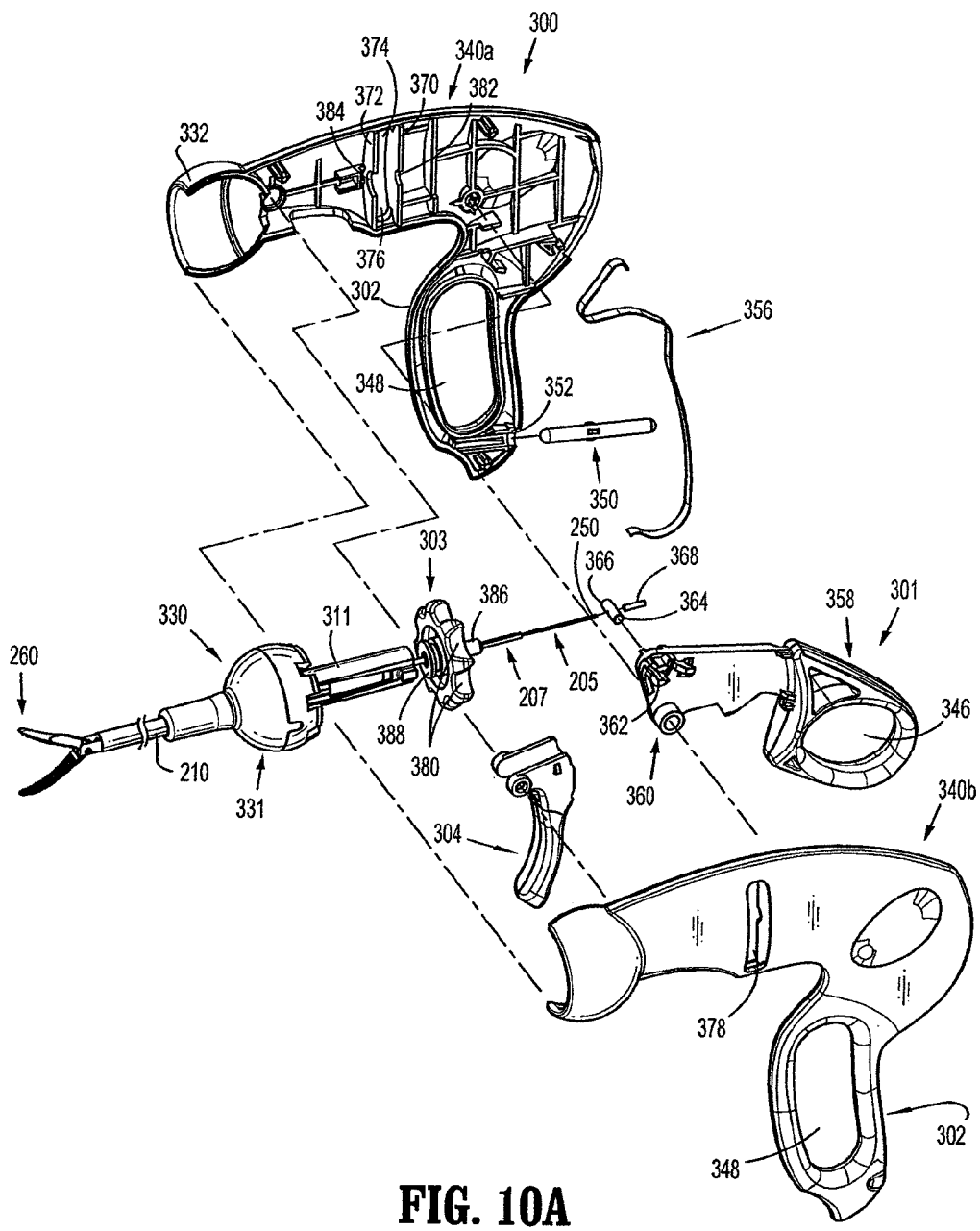
FIG. 10A is a perspective exploded view of the surgical device of FIG. 1.

With reference to FIGS. 9 and 10, handle assembly 300 is configured to be electromechanically coupled to an electrosurgical generator (not shown) and includes a housing 340 for storing, among other things, at least some parts of an articulation mechanism 330. As seen in FIG. 10A, housing 340 includes a first half 340a and a second half 340b configured to attach to one another. In several embodiments, first and second halves 340a, 340b may be made of a polymer (or any other suitable material). First and second halves 340a, 340b collectively form a cup 332 for holding a ball 331 of articulation mechanism 330. Cup 332 is positioned on a distal end portion 344 (FIG. 9) of handle assembly 300. Handle assembly 300 further includes a movable thumb loop 301 positioned on a proximal end portion 342 (FIG. 9) thereof. Movable thumb loop 301 is operatively connected to end effector 260 (FIG. 7) and is configured to move upwardly and downwardly relative to housing 340. In various embodiments, movable thumb loop 301 is pivotally secured to housing 340. Moving movable thumb loop 301 with respect to housing 340 causes end effector 260 to move between the open position and the approximated position, as discussed in detail below. Movable thumb loop 301 defines an aperture 346 dimensioned to receive a user's finger. Aperture 346 is located in a proximal end portion 358 of movable thumb loop 301. At least a distal end portion 360 of movable thumb loop 301 is positioned inside housing 340.

Handle assembly 300 further includes a finger loop 302 defining an opening 348 dimensioned to receive a user's finger. Finger loop 302 remains stationary relative to housing 340. Finger loop 302 includes a longitudinal cavity 352 (FIG. 10A) for retaining a post 350 adapted to facilitate electromechanical coupling between surgical device 100 and an electrosurgical generator (not shown). Post 350 is partially positioned within finger loop 302 and is made wholly or partly of an electrically conductive material. In one embodiment, an electrical and thermal insulating sheath (not shown) wraps a portion of post 350 located outside of finger loop 302. This insulating sheath protects the user from the electrical current traveling through post 350 during the operation of surgical device 100. The portion of post 350 located inside finger loop 302 is electromechanically coupled to an electrical connector 356 made of an electrically conductive material. Electrical connector 356 extends through finger loop 302 into an inner portion of housing 340. A portion of electrical connector 356 located inside housing 340 is disposed in electromechanical cooperation with an alignment tube 207 made of an electrically conductive material. Alignment tube 207 surrounds a portion of an actuation cable 205 (FIG. 10A). In some embodiments, actuation cable 205 is made of an electrically conductive material. In these embodiments, an electrical current traveling through alignment tube 207 can reach actuation cable 205.

A proximal end 250 (FIG. 10A) of actuation cable 205 is operatively connected to distal end portion 360 of movable thumb loop 301. In certain embodiments, distal end portion 360 of movable thumb loop 301 defines a longitudinal recess 362 aligned transversely relative to actuation cable 205. Longitudinal recess 362 is dimensioned to receive a pin 364. Pin 364 has a hole 366 longitudinally aligned with actuation cable 205. Longitudinal hole 366 is adapted to receive proximal end 250 of actuation cable 205. Ferrule 368 surrounds proximal end 250 of inner shaft 205 and retains proximal end 250 of actuation cable 205 within longitudinal hole 366 of pin 364. Pin 364 in turn connects proximal end 250 of actuation cable 205 to distal end portion 360 of movable thumb loop 301. Alignment tube 207 is crimped onto the actuation cable 205 distally of pin 364. Thus, ferrule 368 and alignment tube 207 sandwich pin 364, maintaining the axial relationship between actuation cable 205 and pin 364. Accordingly, when pin 364 is moved, actuation cable 205 moves as well. However, actuation cable 205 is capable of axial rotation in relation to the pin 364.

As seen in FIGS. 10B and 10C, alignment tube 207 does not have a circular external cross shape. Instead, alignment tube 207 has one or more flat sides. At least one side of alignment tube 207 may have a round profile. The non-circular external cross section of alignment tube 207 corresponds to the internal cross section of the internal passageway 399 extending through proximal elongated portion 386 (FIGS. 10A, 10D, and 10E) of rotation wheel 303. Thus, when the rotation wheel 303 is rotated, alignment tube 207 rotates as well and, because it is crimped to actuation cable 205, the actuation cable 205 will also rotate.

Figure 20:
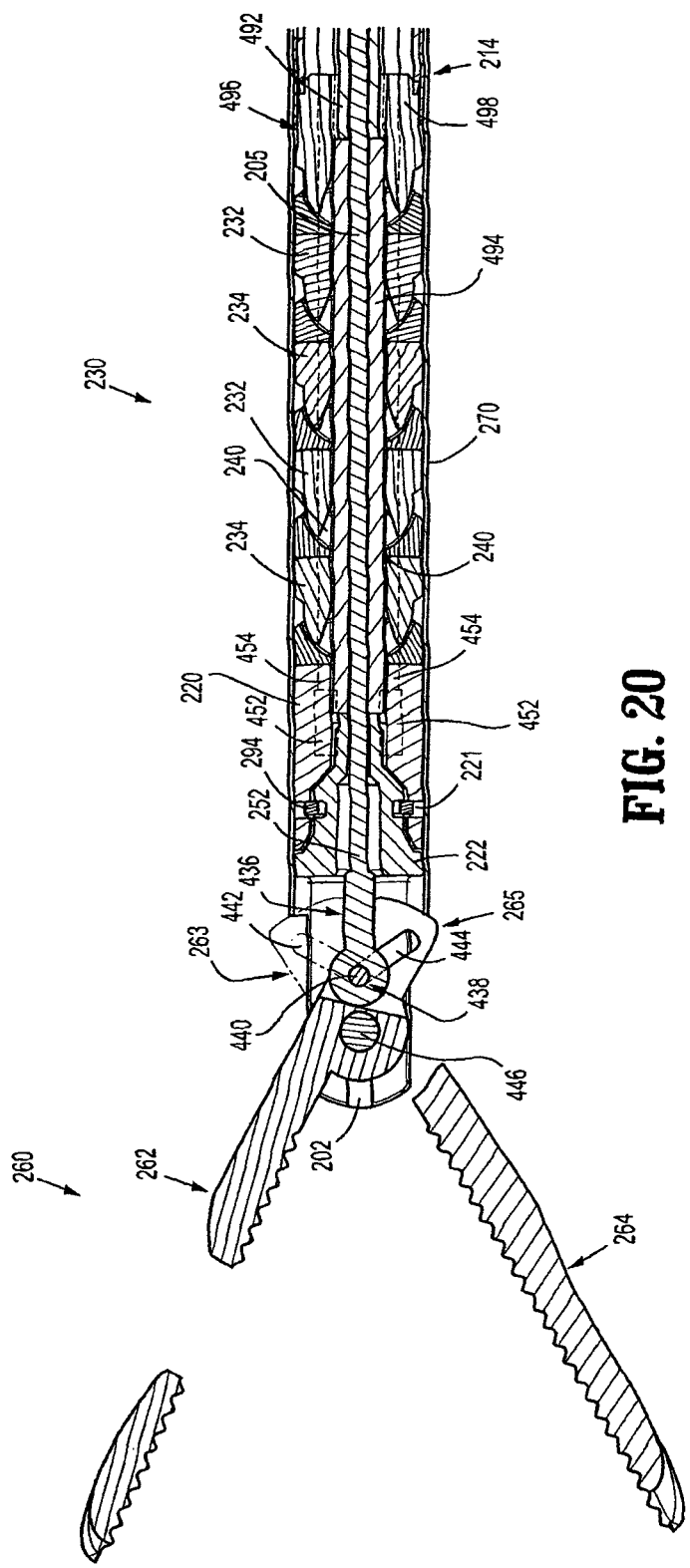
FIG. 20 is a side cross-sectional view of the end effector and the articulating section of the surgical device of FIG. 1, taken around section 20 of FIG. 17.
Figure 31:
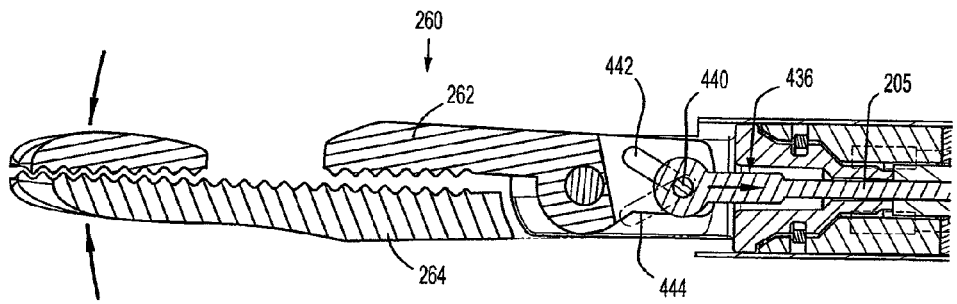
FIG. 31 is a side cross-sectional view of the end effector and a portion of the articulating section of the surgical device of FIG. 1, depicting end effector moving an approximated position in response to an actuation of the movable thumb loop shown in FIG. 30.

Movable thumb loop 301 is configured to move relative to housing 340 to actuate end effector 260. In various embodiments, movable thumb loop 301 can pivot toward and away from finger loop 302. When an operator moves movable thumb loop 301 toward finger loop 302, actuation cable 205 translates in a proximal direction. As a result of this proximal translation, first and second jaw members 262, 264 of end effector 260 move from an open position (FIG. 20) to an approximated position (FIG. 31). Moving movable thumb loop 301 away from finger loop 301, on the other hand, urges actuation cable 205 in a distal translation. In response to this distal translation, first and second jaw members 262, 264 of end effector 260 move from the approximated position (FIG. 31) to the open position (FIG. 20).

Handle assembly 300 also includes a rotation wheel 303 mounted on alignment tube 207. Rotation wheel 303 is configured to rotate relative to housing 340. Some portions of rotation wheel 303 stick out of housing 340, allowing an operator to reach rotation wheel 303. Other portions of rotation wheel 303 are secured within housing 340. Housing 340 includes a first inner wall 370 and a second inner wall 372 spaced apart from each other. First and second inner walls 370, 372 define a gap 374 (FIG. 10A) therebetween. Gap 374 is dimensioned to receive at least a portion of rotation wheel 303 and is disposed in communication with a first slot 376 (FIG. 10A) of first half 340a and a second slot 378 (FIG. 10A) of second half 340b of housing 340. At least some portions of rotation wheel 303 exit housing 340 through first and second slots 376, 378, thereby providing access to rotation wheel 303. Each of first and second inner walls 370, 372 defines a recess 382 and 384 (FIG. 10A) for holding portions of rotation wheel 303. Specifically, recess 382 of inner wall 370 supports a proximal elongate portion 386 of rotation wheel 303. Proximal elongate portion 386 extends proximally from rotation wheel 303 and surrounds at least a portion of alignment tube 207 (see FIG. 9). Recess 384 of second inner wall 372 supports a distal tubular member 388 releasably attached to a distal end of rotation wheel 303.

Figure 11A:
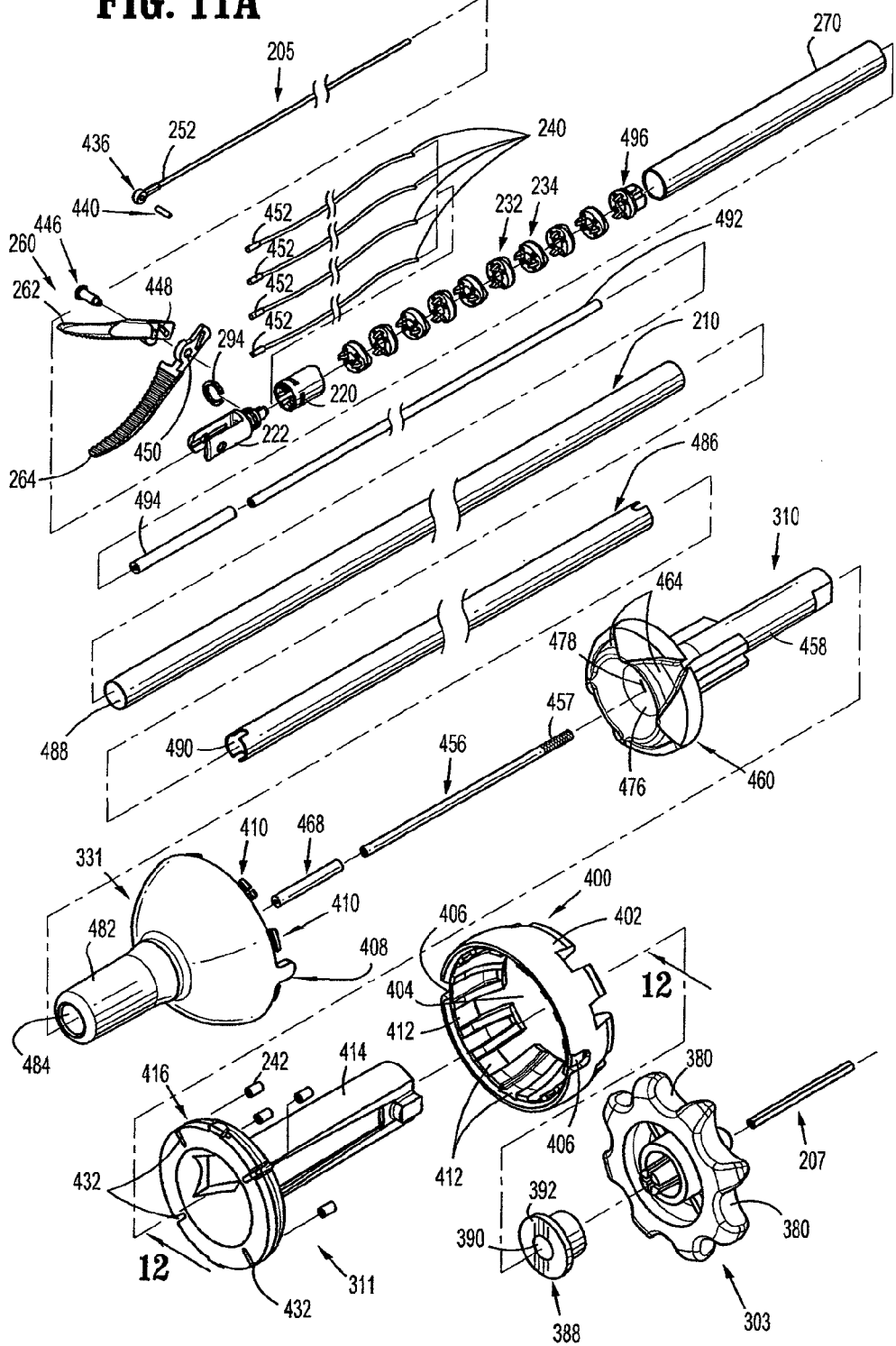
FIG. 11A is a perspective exploded view of an articulation mechanism, the end effector, and the articulating section of the surgical device of FIG. 1.
Figure 11B:
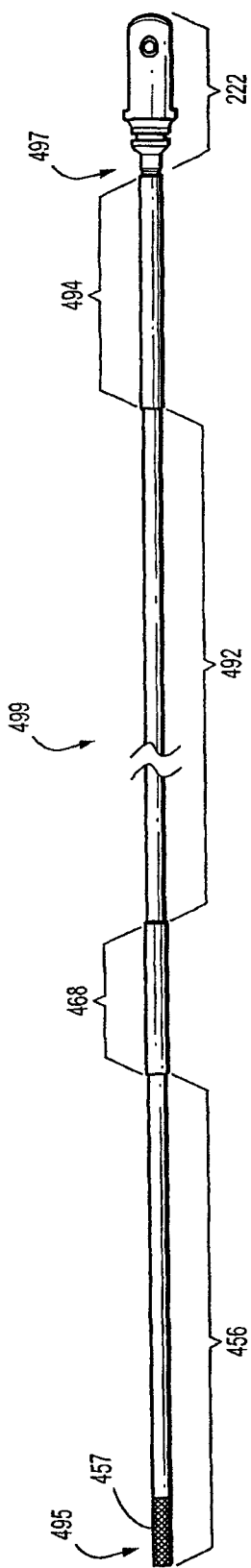
FIG. 11B is a side view of a torque shaft of the surgical device of FIG. 1.
Figure 11C:
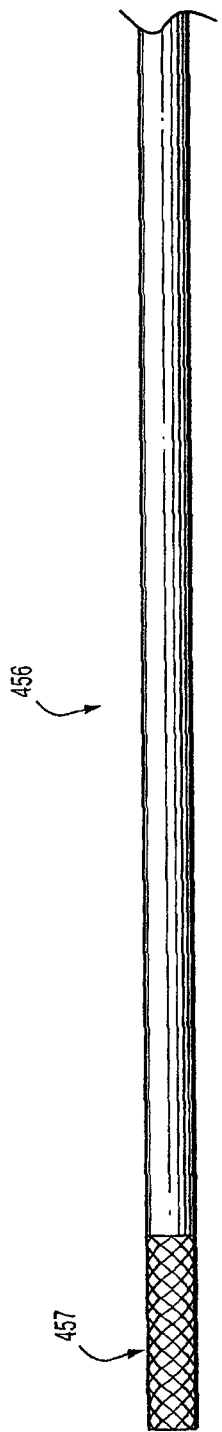
FIG. 11C is a side view of a proximal torque tube of the torque shaft shown in FIG. 11B.
Figure 21:
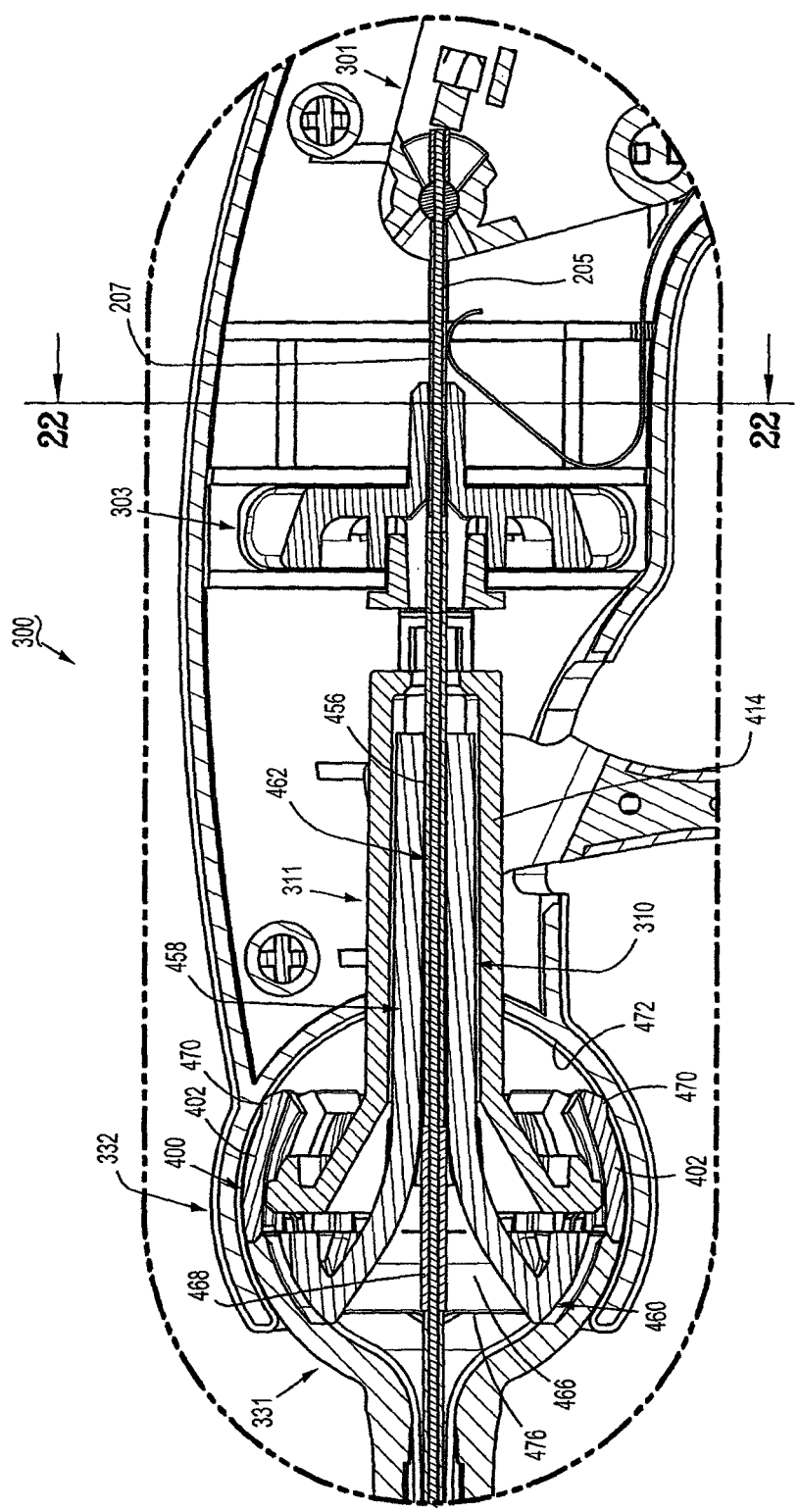
FIG. 21 is a side cross-sectional view of a portion of the handle assembly of the surgical device of FIG. 1, taken around section 21 of FIG. 17.
Figure 22:
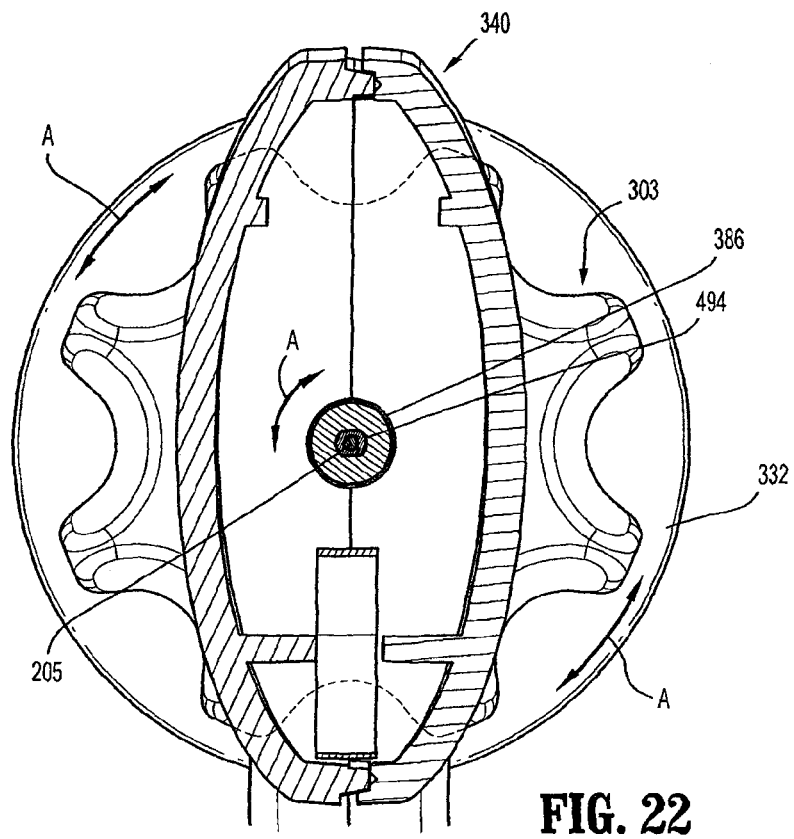
FIG. 22 is a rear cross-sectional view of a portion of the handle assembly of the surgical device of FIG. 1, taken along section line 22-22 of FIG. 21.

With reference to FIGS. 11B and 11C, a torque shaft 499 has a proximal end portion 495 and a distal end portion 497 and, during operation, transfers rotational torque from rotation wheel 303 (FIG. 11A) to end effector 260 (FIG. 8). The distal end portion 497 of torque shaft 499 is operatively connected to coupling member 222, while the proximal end portion 495 of torque shaft 499 is coupled rotation wheel 303 (FIG. 21). Torque shaft 499 includes a proximal torque tube 456, a proximal torque coil 468, a distal torque tube 492, and a distal torque coil 494. Each component of torque shaft 499 is connected to one another. In certain embodiments, all the components comprising torque shaft 499 are welded together and distal torque coil 494 is welded to coupling member 222. In some embodiments, proximal torque coil 468 and distal torque coil 494 are each made of three layers of torque coil sold by ASAHI INTECC CO. or equivalents. The different layers of the torque coil have opposite direction winds so that the coil can be rotated in either direction without unwinding. As seen in FIG. 11C, proximal torque tube 456 includes a diamond knurl patterned section 457 at its proximal end.

Figure 11D:
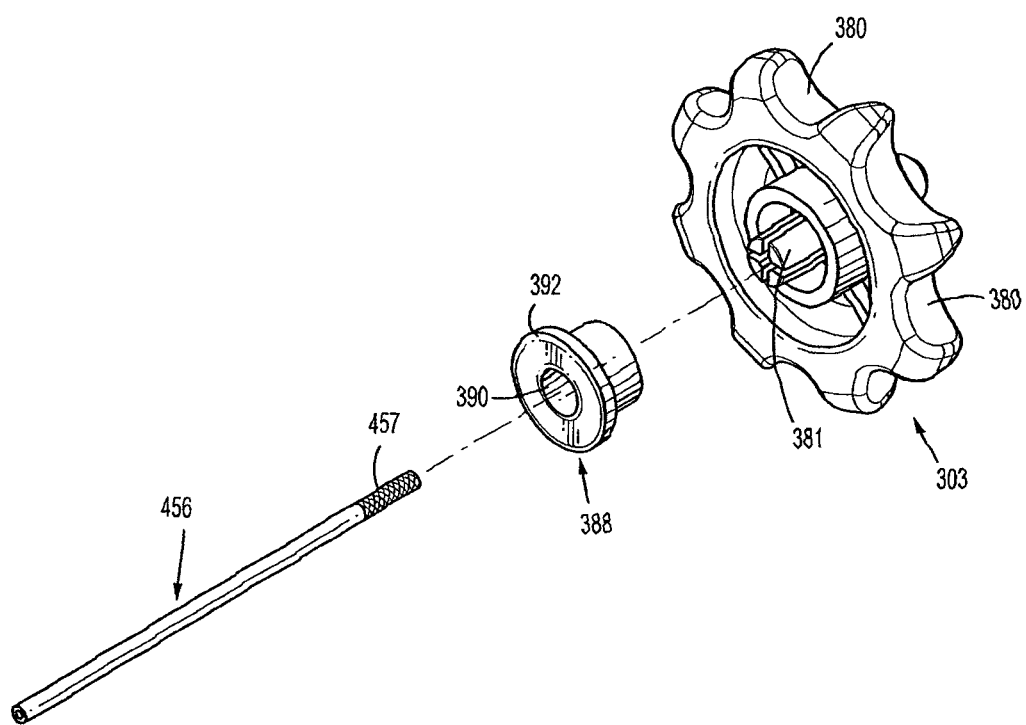
FIG. 11D is a perspective view of a rotation wheel, a distal tubular member 388, and a proximal torque tube 456 of the surgical device of FIG. 1.
Figure 23:
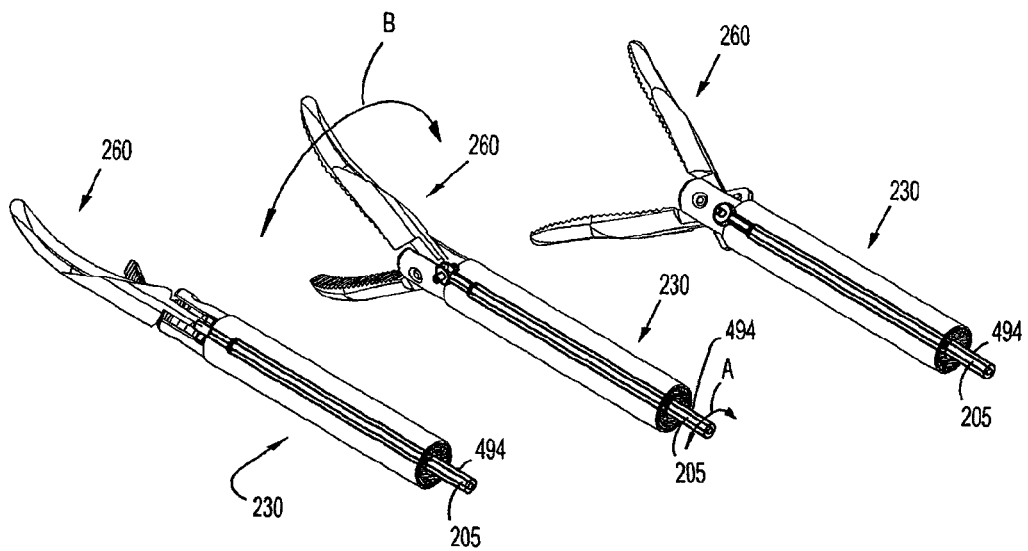
FIG. 23 is a perspective view of the end effector and the articulating section of the surgical device of FIG. 1 during various stages of rotation along its longitudinal axis.

Referring to FIG. 11D, rotating rotation wheel 303 causes proximal torque tube 456 to rotate in the same direction. The torque and resulting rotation is then transferred through the other elements of torque shaft 499 to the coupling member 222, thus rotating the end effector 260 (see FIG. 23). Rotation wheel 303 includes a plurality of undulations 380 positioned around its periphery and four distal extension members 381. Undulations 380 are ergonomically configured to receive a user's fingers and facilitate rotation of wheel 303 by the user. Proximal torque tube 456 fits within the four distal extension members 381 with at least a portion of the diamond knurled pattern section 457 contacting the inner surfaces of the four distal extending members 381. A distal tubular member 388 is placed over the four distal extension members 381. Distal tubular member 388 defines a longitudinal opening 390 dimensioned for receiving the four distal extension members 381 and includes a flange 392 disposed around a distal end thereof. Longitudinal opening 390 of distal tubular member 388 contacts the external surfaces of the four distal extension members 381. The internal diameter of the longitudinal opening 390 is such that, when distal tubular member 388 is placed over the four extension members 381 and the proximal torque tube 456, the four extension members 381 are pressed into the diamond knurled pattern section 457, creating a press fit.

With continued reference to FIGS. 9 and 10, articulation mechanism 330 includes an articulation lock trigger 304 positioned distally of rotation wheel 303 and configured for locking the position of articulating section 230 (FIG. 2) relative to elongate outer tube 210. Articulation lock trigger 304 is operatively coupled to an articulation cable plate 311 and can move relative to housing 340. In several embodiments, articulation lock trigger 304 can pivot with respect to housing 340 between a first or unlocked position and a second or locked position. When an operator moves articulation lock trigger 304 from the unlocked position toward the locked position, articulation cable plate 311 moves proximally with respect to housing 340 to lock the position of articulating section 230 with respect to elongate outer tube 210, as discussed in detail below. In the depicted embodiment, articulation lock trigger 304 defines a detent recess 398 positioned on a proximal surface therefore and adapted to receive a detent 394 of articulation cable plate 311. Detent 394 of articulation cable plate 311 engages detent recess 398 when articulation lock trigger 304 is located in the locked position. Articulation lock trigger 304 also include at least one tab 396 positioned within housing 340. In some embodiments, articulation lock trigger 304 includes two tabs 396 located on opposite sides of articulation lock trigger 304.

Figure 12:
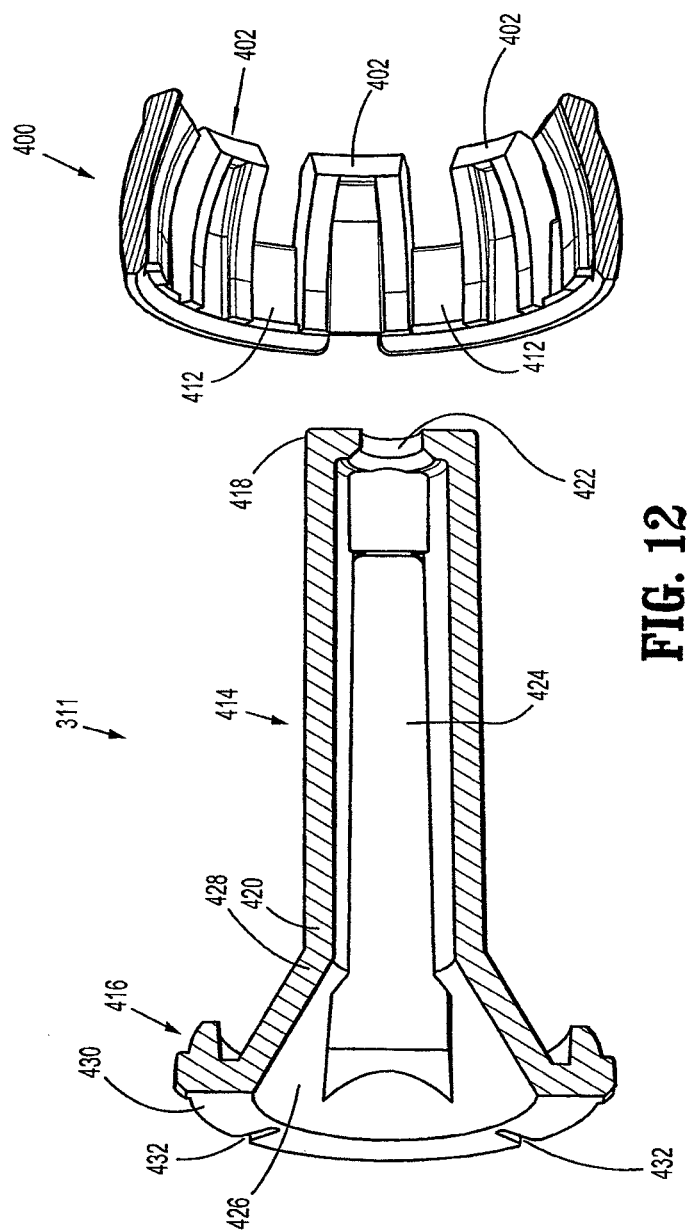
FIG. 12 is a perspective cross-sectional view of an articulation cable plate and an articulation lock ring of the articulation mechanism of FIG. 11A, taken along section line 12-12 of FIG. 11A.

Referring to FIGS. 11 and 12, articulation mechanism 330 includes an articulation lock ring 400 partially surrounding articulation lock plate 311. Articulation lock ring 400 defines an opening 404 (FIG. 11A) dimensioned to receive articulation lock plate 311 and includes a plurality of locking fingers 402 extending proximally therefrom. Locking fingers 402 are positioned around a periphery of articulation lock ring 400 and may be (wholly or partly) made of a resilient material. Articulation lock ring 400 is positioned inside cup 332 of housing 340 (FIG. 9) and includes two lateral slots 406 (FIG. 11A) disposed in a diametrically opposed relation to each other. Each lateral slot 406 is adapted to receive an extension member 408 of ball 331. In some embodiments, ball 331 includes two extension members 408 disposed in diametrically opposed relation to each other. Each extension member 408 extends proximally from ball 331. When extension members 408 of ball 331 engage slots 406 of articulation lock ring 400, ball 331 is precluded, or at least hindered, from rotating relative to articulation lock ring 400. Ball 331 further includes snap-fit detents 410, or any other apparatus, mechanism, or means suitable for facilitating secure engagement between the ball 331 and articulation lock ring 400. Snap-fit detents 410 are configured to securely engage engagement walls 412 located around an inner surface of articulation lock ring 400 and between fingers 402.

As shown in FIG. 11A, articulation lock ring 400 partially surrounds an articulation cable plate 311. Articulation cable plate 311 has an elongate portion 414 and a cable engaging portion 416. Elongate portion 414 of articulation cable plate 311 has a proximal end 418 and a distal end 420 and defines an opening 422 at proximal end 418 and a bore 424 extending therethrough. Opening 422 leads to bore 424 and is dimensioned to receive proximal torque tube 456 (FIG. 12). Bore 424 is also dimensioned to receive elongate section 458 of annular hub 310 (FIG. 10A).

With continued reference to FIG. 12, cable engaging portion 416 of articulation cable plate 311 is coupled to a distal end 420 of elongate portion 414 and defines an inner cavity 426. In some embodiments, cable engaging portion 416 has a frusto-conical shape. Inner cavity 426 is disposed in communication with bore 424. Additionally, cable engaging portion 416 includes a proximal section 428 connected to elongate portion 414 and a distal section 430 defining a plurality of channels 432. Channels 432 are positioned around the perimeter of distal section 430 of cable engaging portion 416 and each is configured to accommodate an articulation cable 240 (FIG. 11A) and a ferrule or crimp 242 (FIG. 11A).

Returning to FIG. 12, articulation mechanism 330 includes one or more articulation cables 240 operatively coupled to articulation cable plate 311. In the depicted embodiment, four articulation cables 240 are operatively connected to articulation cable plate 311. A ferrule 242 retains each of the four articulation cables 240 in articulation cable plate 311. Specifically, a ferrule 242 is positioned in a channel 432 of articulation cable plate 311 which surrounds and holds a portion of an articulation cable 240, thereby maintaining articulation cable 240 connected to articulation cable plate 311.

Figure 13:
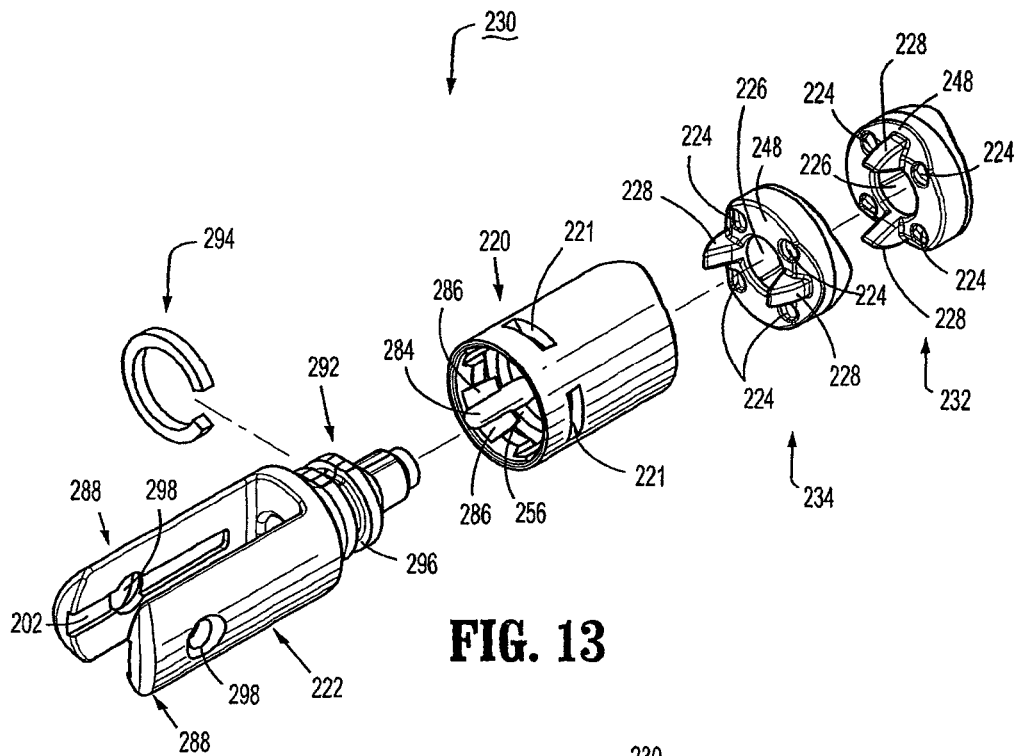
FIG. 13 is a front, exploded view of a portion of the articulating section of the surgical device of FIG. 1.
Figure 14:
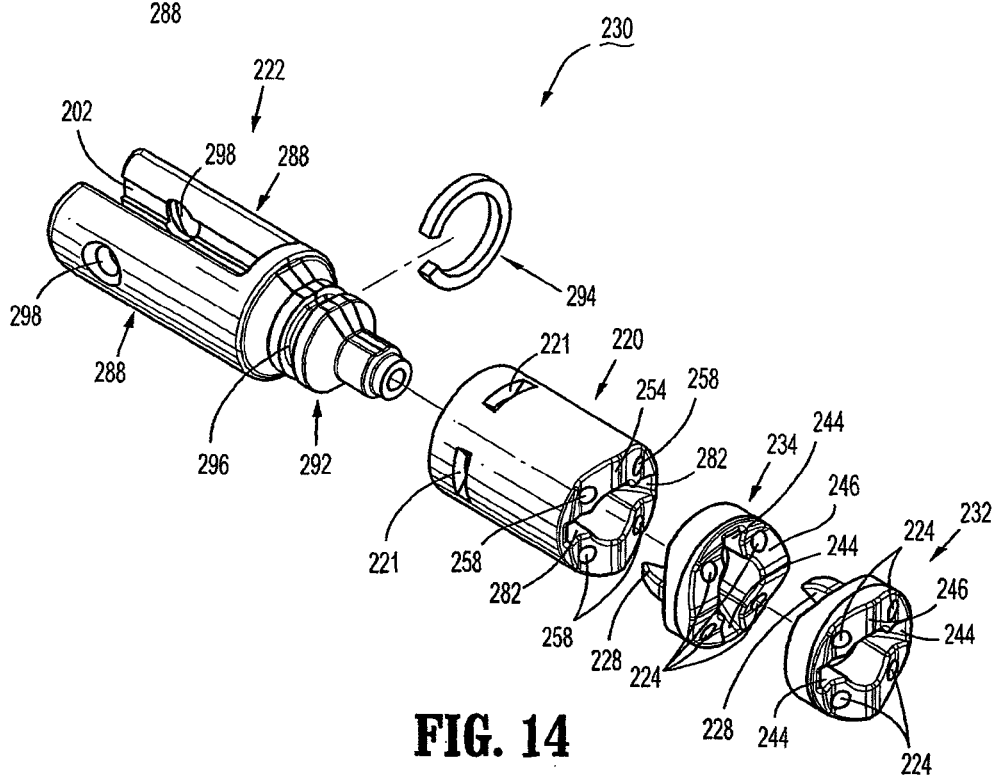
FIG. 14 is a rear, exploded view of a portion of the articulating section the surgical device of FIG. 1.
Figure 15:
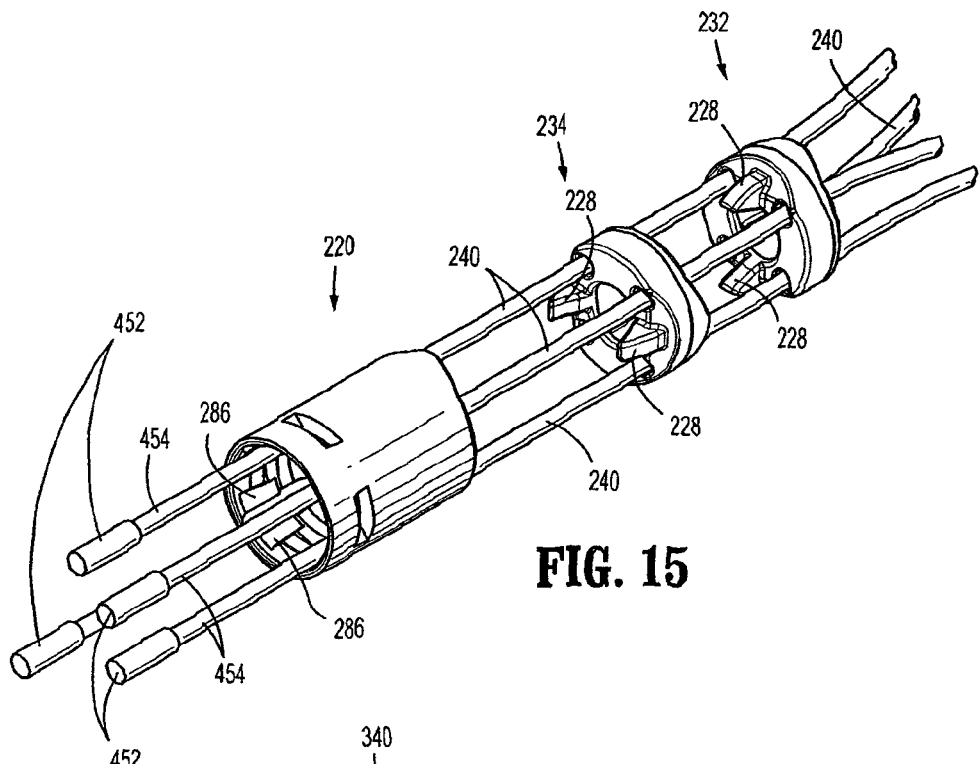
FIG. 15 is a perspective view of the articulating section of the surgical device of FIG. 1, showing articulation cables passing through articulation links and a distal outer tube of the articulating section.

With reference to FIGS. 13-15, articulation cables 240 are operatively coupled to articulating section 230 (see also FIG. 20). Articulating section 230 includes a plurality of articulation links 232, 234 (see also FIG. 11A), a distal outer tube 220, and a coupling member 222. In certain embodiments, coupling member 22 is a knuckle coupler. Each articulation link 232, 234 defines at least one bore 224 adapted to receive an articulation cable 240 (FIG. 15) and a central opening 226 adapted to receive distal torque tube 492 (FIG. 20). In the depicted embodiment, each articulation link 232, 234 includes four bores 224 located around central opening 226. Articulation links 232, 234 further include extension members 228 extending distally therefrom and recesses 244 (FIG. 14) for receiving extension members 228. Recesses 244 are positioned on a proximal surface 246 of each articulation link 232, 234. Proximal surfaces 246 of articulation links 232, 234 each have a contoured profile. The contoured profile of proximal surfaces 246 is configured to mate with the contoured profile of distal surfaces 248 of articulation links 232, 234. Although proximal surfaces 246 and distal surfaces 248 mate with each other, the contoured profile of these surfaces 246, 248 provide articulation links 232, 234 certain degree of motion relative to each other. In addition, articulation links 232, 234, albeit substantially similar, have different orientations with respect to each other. In some embodiments, articulation link 232 is oriented about 90 degrees relative to articulation link 234, as shown in FIG. 13.

With continued reference to FIGS. 13-15, distal outer tube 220 has a proximal surface 254 contoured to mate with distal surface 248 of either articulation link 232 or 234 while permitting movement of the adjacent articulation link 232 or 234 relative to distal outer tube 220. Recesses 282 are defined on proximal surface 254 and each is configured to receive an extension member 228 of articulation links 232, 234. Proximal surface 254 of distal outer tube 220 further defines one or more holes 258 dimensioned to receive articulation cables 240. In the depicted embodiment, distal outer tube 220 has four holes 258. It is envisioned, however, that distal outer tube 220 may have more or fewer holes 258. Moreover, distal outer tube 220 defines a central opening 256 adapted to receive at least a portion of coupling member 222 and at least one channel 284 for holding a portion of an articulation cable 240 within distal outer tube 220. In some embodiments, distal outer tube 220 includes four channels 284 disposed around an inner surface of distal outer tube 220. In addition, distal outer tube 220 include two retaining wall 286 positioned on opposite sides of each channel 284 to retain an articulation cable 240 in channel 284. (See also FIG. 15).

With continued reference to FIGS. 13-15, coupling member 222 includes two legs 288 defining a space therebetween and a proximal projection 292. Each leg 288 of coupling member 222 includes a transverse opening 298 and a longitudinal track 202 disposed along an inner surface thereof. Proximal projection 292 of coupling member 222 defines an annular recess 296 adapted to receive a seal or band 294. In the illustrated embodiment, band or seal 294 has a substantially C-shaped. Band 294 aids in securing coupling member 222 to distal outer tube 220 when band 294 is placed in recess 296 and proximal projection 292 is positioned inside distal outer tube 220. When projection 292 is placed within distal outer tube 220, portions of band 294 stick out through circumferential slots 221 of distal outer tube 220, securing coupling member 222 to distal outer tube 220. Distal outer tube 220 may have one or more circumferential slots 221. In the depicted embodiment, distal outer tube 220 has four circumferential slots 221 positioned around a periphery thereof.

Figure 16:
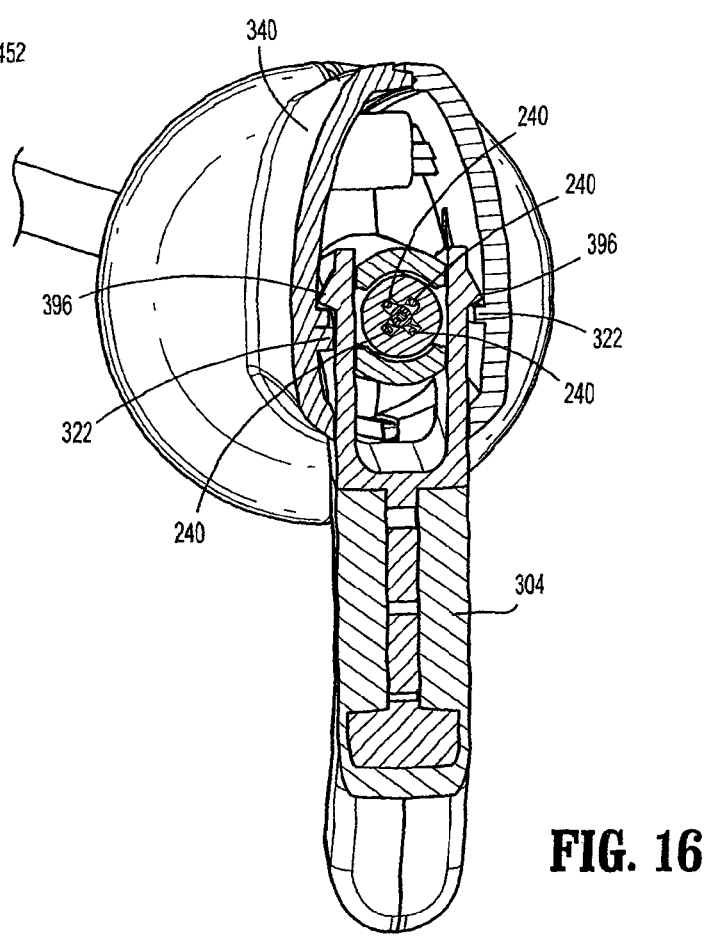
FIG. 16 is a rear cross-sectional view of the handle assembly of FIG. 9, taken along section line 16-16 of FIG. 9.

Referring to FIG. 16, articulation cables 240 are operatively coupled to articulation lock trigger 304. In some embodiments, articulation lock trigger 304 includes two tabs 396 located on opposite sides of articulation lock trigger 304, as discussed above. Articulation lock trigger 304 can move relative to housing 340 between a locked position and an unlocked position, as discussed in detail below. Additionally, in some embodiments, as will be discussed in detail below (see FIGS. 65A-68B), articulation lock trigger 304 may initially be disposed in a "shipping" configuration wherein articulation cables $240_A$, $240_B$, $240_C$, $240_D$ are substantially un-tensioned. Upon the initial actuation of articulation lock trigger 304, articulation lock trigger 304 is permanently moved into a "use" configuration, wherein the articulation lock trigger 304 may be moved between the locked and unlocked positions. When articulation lock trigger 304 is placed in the locked position, articulation mechanism 330 (FIG. 9) fixes the position of articulation cables 240, thus precluding, or at least inhibiting, articulation of articulating section 230 relative to longitudinal axis "X." (See FIG. 2). Conversely, when articulation lock trigger 304 is placed in the unlocked position (FIG. 16), articulation mechanism 330 (FIG. 9) allows articulating section 230 to articulate relative to longitudinal axis "X." (See FIG. 2). In the unlocked position, tabs 396 of articulation lock trigger 304 seat on internal ribs 322 of housing 340, thereby holding articulation lock trigger 304 in the unlocked position.

As seen in FIGS. 17-19, an embodiment of surgical device 100 includes four (4) articulation cables $240_A$, $240_B$, $240_C$, $240_D$. Each articulation cable $240_A$, $240_B$, $240_C$, $240_D$ extends from articulation cable plate 311 to articulating section 230. While extending through surgical device 100, articulation cables $240_A$, $240_B$, $240_C$, $240_D$ change their position 180 degrees (see FIGS. 18 and 19), allowing articulating section 230 to articulate in the same direction as handle assembly 300.

With reference to FIG. 20, articulating section 230 is operatively coupled to end effector 260. Actuation cable 205 extends through articulating section 230 and is connected to end effector 260. A distal torque coil 494 surrounds a portion of actuation cable 205 extending through articulating section 230. In one embodiment, distal torque coil 494 is a SUS304 or SUS316 grade stainless steel torque coil sold by ASAHI INTECC CO., LTD. Distal end 252 of actuation cable 205 is operatively coupled to end effector 260. In some embodiments, a coupling 436 connects distal end 252 of actuation cable 205 to end effector 260 (see also FIG. 11A). Coupling 436 defines a transverse hole 438 dimensioned to receive a pin 440. In these embodiments, pin 440 passes through hole 438 and cam slots 442, 444 of first and second jaw members 262, 264, thereby pivotally coupling actuation cable 205 to end effector 260. First jaw member 262 has a cam slot 444 located at a proximal portion 265 thereof. Cam slot 444 defines an oblique angle relative to actuation cable 205. Second jaw member 264 has a cam slot 442 located at a proximal portion thereof 263. Cam slot 442 defines an angle with respect to actuation cable 205. Pin 440 is slidably positioned in cam slots 442, 442. As a consequence, first and second jaw members 262, 264 move between open and approximated positions upon longitudinal translation of actuation cable 205. As discussed in detail below, an operator can move first and second jaw members 262, 264 from the open position to the approximated position by moving movable thumb loop 301 toward finger loop 302 (see FIG. 17). As movable thumb loop 301 moves toward finger loop 302, actuation cable 205 translates proximally to urge pin 440 in a proximal direction. When pin 440 is urged proximally, pin 440 slides along cam slots 442, 440, causing first and second jaw members 262, 264 to move toward each other.

With continued reference to FIG. 20, first and second jaw members 262, 264 are pivotally coupled to each other. In certain embodiments, a pivot pin 446 pivotally interconnects first and second jaw members 262, 264. First jaw member 262 defines an opening 448 (FIG. 11A) dimensioned to receive pivot pin 446. Second jaw member 264 defines an opening 450 (FIG. 11A) dimensioned to receive pivot pin 446. As seen in FIGS. 13 and 14, coupling member 222 has a pair of traverse openings 298 configured to receive pivot pin 446 (FIG. 20). Longitudinal tracks 202 engage pivot pin 446 and guide the translation of pivot pin 446 during actuation of end effector 260.

FIG. 20 shows (in phantom) articulation cables 240 secured within distal outer tube 220 of articulating section 230. Articulation cables 240 pass through bores 224 (FIG. 13) of articulation links 232, 234 until reaching distal outer tube 220. In some embodiments, a ferrule or crimp 452 is attached to the distal end 454 of each articulation cable 240. (See also FIGS. 11 and 15). Ferrules 452 (shown in phantom) help retain distal ends 454 of articulation cables 240 within distal outer tube 220. As discussed above, distal outer tube 220 is operatively coupled with an articulation link 234. Articulation links 232, 234 are operatively coupled to each other. Such connection allows articulating section 230 to articulate relative to longitudinal axis "X" (FIG. 2). It is envisioned that the degrees of motion of articulating section 230 is directly proportional to the number of articulation links 232, 234. Articulating section 230 includes a most-proximal link 496. Most-proximal articulation link 496 is substantially similar to articulation links 232, 234. However, most-proximal articulation link 496 includes an extension 498 protruding proximally. Extension 498 is adapted to be securely received within distal end 214 of endoscopy assembly 200.

Referring to FIG. 21, actuation cable 205 is operatively connected to movable thumb loop 301. Alignment tube 207 surrounds a portion of actuation cable 205 extending from movable thumb loop 301 to rotation wheel 303. Handle assembly 300 further includes a proximal torque tube 456 surrounding a portion of actuation cable 205 extending from rotation wheel 303 to articulation cable plate 311 (see also FIG. 11A). Proximal torque tube 456 is partially positioned within an annular hub 310. Annular hub 310 is partially positioned inside articulation cable plate 311 and includes an elongate section 458 and a cable holding section 460. Elongate section 458 of annular hub 310 is at least partially positioned within elongate portion 414 of articulation cable plate 311 and defines a bore 462 dimensioned to receive actuation cable 205 and proximal torque tube 456. Cable holding section 460 includes a plurality of recesses 464 (FIG. 11A)

configured to accommodate articulation cables 240 and an cavity 466 leading to bore 462 of elongate section 458. Another proximal torque coil 468 is partially positioned in cavity 466 and surrounds a portion of actuation cable 205 extending from elongate section 458 to cable holding portion 460 of annular hub 310 (see also FIG. 11A). In certain embodiments, proximal torque coil 468 is made of a flexible material. In several embodiments, proximal torque coil 468 is (wholly or partly) made of a shape-memory material such Nickel Titanium Alloy. In some embodiments, proximal torque coil 468 is made (wholly or partly) of a stainless steel torque coil sold by ASAHI INTECC CO., LTD. Cable holding section 460 further includes an elastic wall 476 covering cavity 466. Elastic wall 476 has a slit 478 (FIG. 11A) that allows passage of proximal torque coil 468 through elastic wall 476. Articulation lock ring 400 encircles at least a portion of annular hub 310. As discussed above, articulation lock ring 400 includes a plurality of locking fingers 402. Each locking finger 402 includes a detent 470 for engaging an inner surface 472 of cup 332. As explained below, inner surface 472 of cup 332 defines a plurality of cavities 474 (FIG. 26) each adapted to retain a detent 470. When detents 474 are placed in cavities 474, end effector 260 (FIG. 11A) is maintained in the neutral position.

In an alternate embodiment, rotating wheel 303 in a first direction causes actuation cable 205 to rotate in the same direction, as indicated by arrows "A". Upon rotation of actuation cable 205 in the first direction, end effector 260 rotates in the same direction, as indicated by arrows "B." For example, a clockwise rotation of rotation wheel 303 with respect to housing 340 causes end effector 260 to rotation in a clockwise direction as well.

Figure 24:
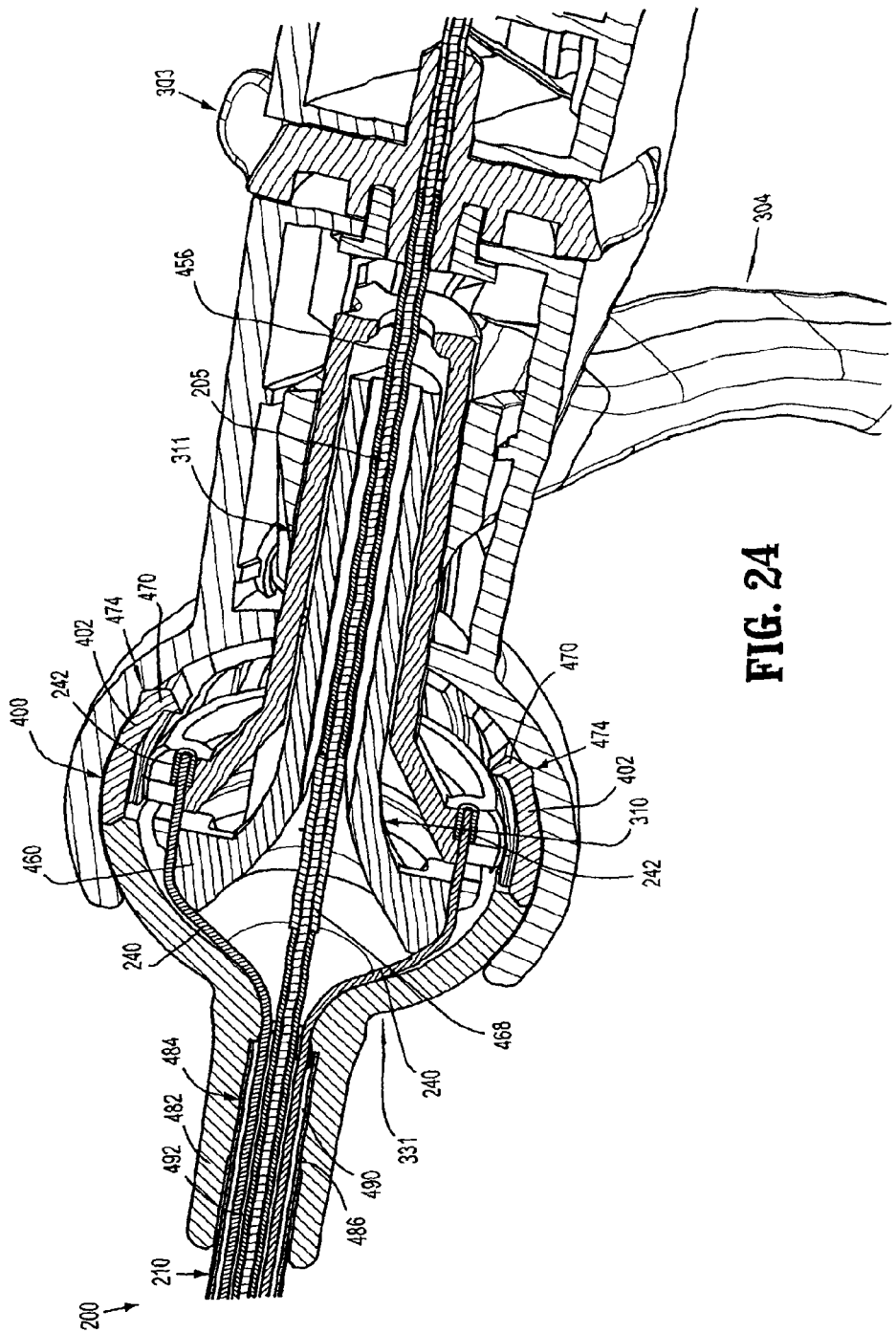
FIG. 24 is a perspective cutaway view of the handle assembly of the surgical device of FIG. 1.
Figure 25:
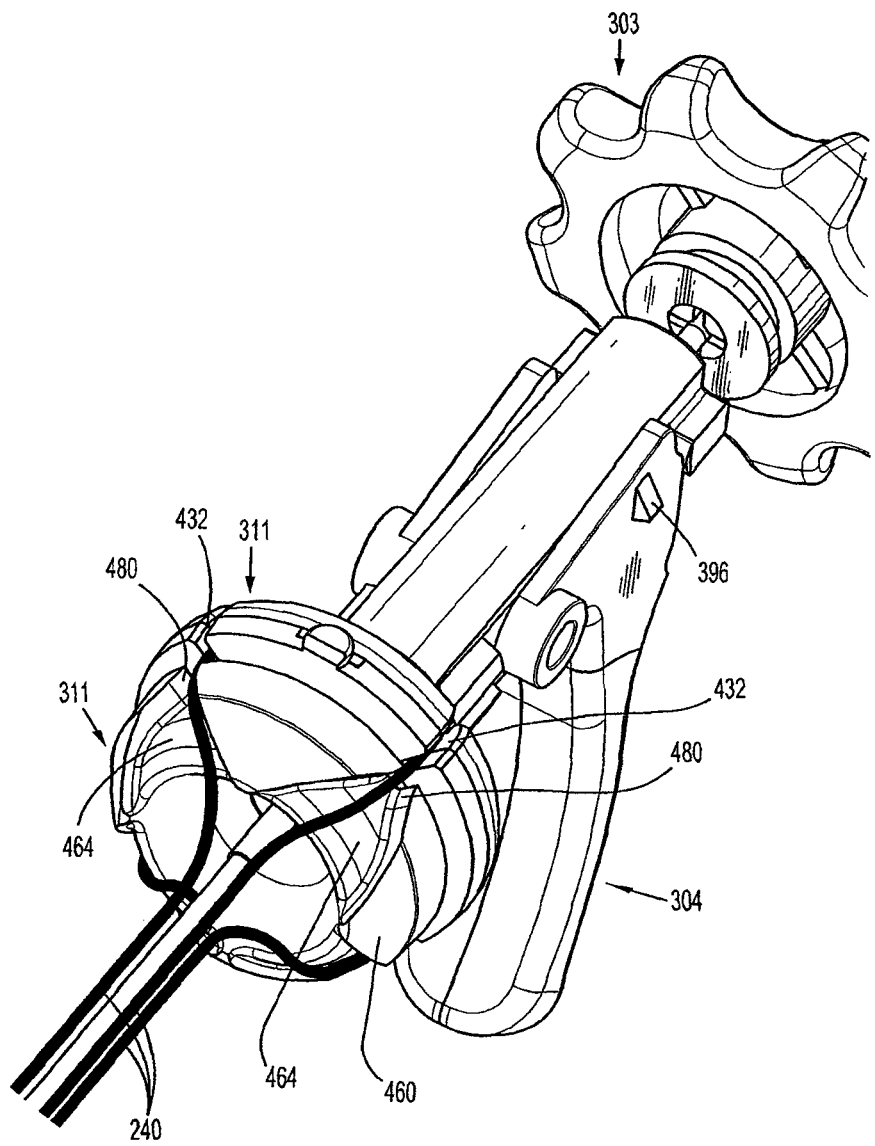
FIG. 25 is a perspective view of a portion of the articulation mechanism of the surgical device of FIG. 1.

With reference to FIGS. 24 and 25, articulation cables 240 are connected to articulation cable plate 311 through ferrules 242. Ferrules 242 are positioned in channels 432 (FIG. 25) of articulation cable plate 311. As a result, articulation cables 240 extend distally from channels 432 of articulation cable plate 311. Channels 432 are aligned with openings 480 (FIG. 25) defined around the perimeter of cable holding section 460. Each opening 480 leads to a recess 464 (FIG. 25) of cable holding section 460. Accordingly, each articulation cable 240 passes through a channel 432, an opening 480, and a recess 464. In certain embodiments, recesses 464 have a triangular profile. Articulation cables 240 also pass through ball 331 and endoscopic assembly 200, as shown in FIG. 24.

With continued reference to FIG. 24, ball 331 includes a distal tube 482 extending distally therefrom. Distal tube 482 defines a bore 484 dimensioned to receive a portion of elongate outer tube 210 and a portion of an elongate inner tube 486 of endoscopic assembly 200. Elongate outer tube 210 defines a bore 488 (FIG. 11A) configured to receive elongate inner tube 486. In turn, elongate inner tube 486 defines a bore 490 adapted to receive actuation cable 205, articulation cables 240, and a distal torque tube 492. Distal torque tube 492 surrounds a portion of actuation cable 205 extending from ball 331 to distal end 214 of endoscopic assembly 200 (see FIG. 20).

Figure 26:
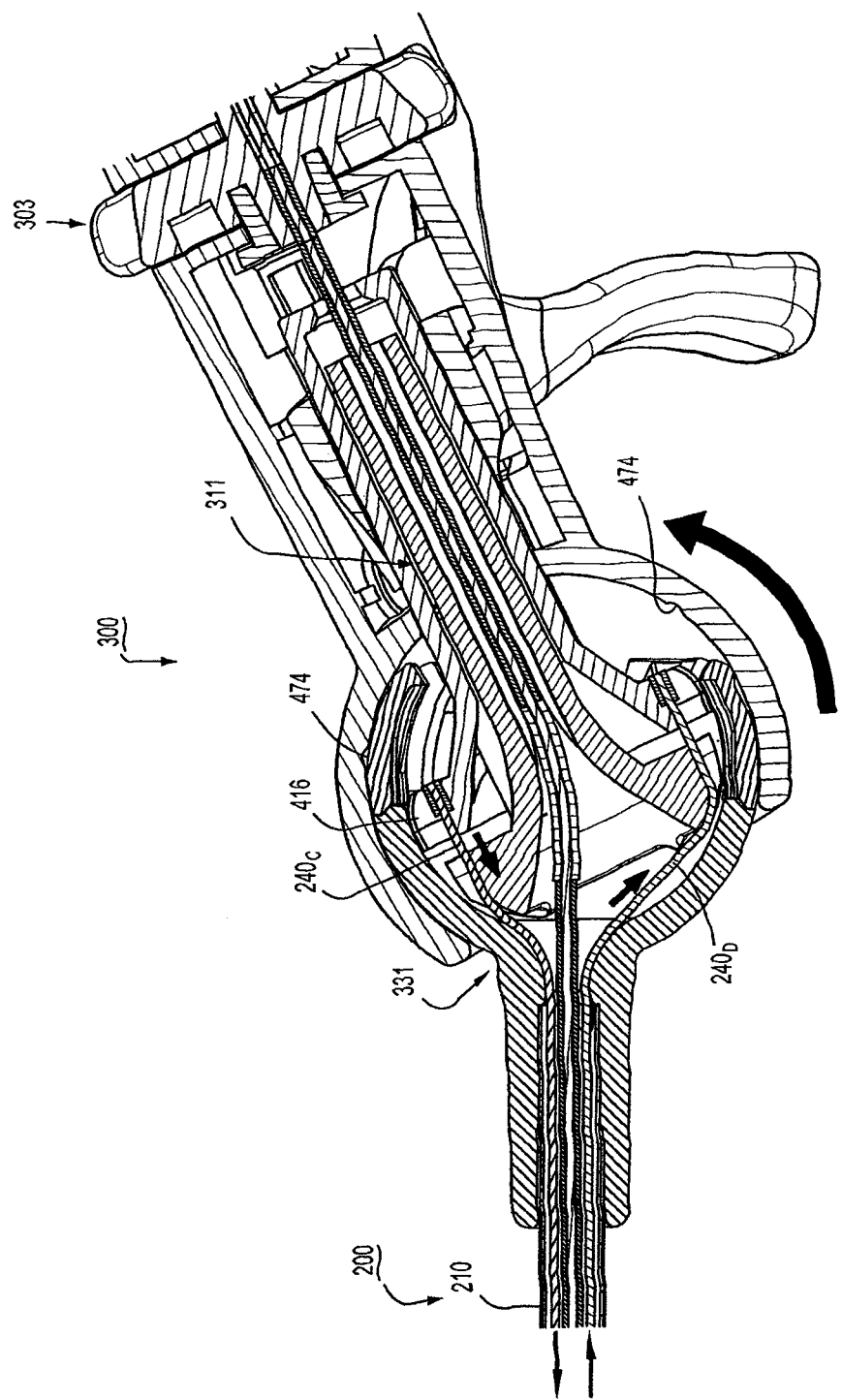
FIG. 26 is a side cross-sectional view of articulation mechanism of the surgical device of FIG. 1, showing a cup moving upwardly relative to a ball of the handle assembly.
Figure 27:
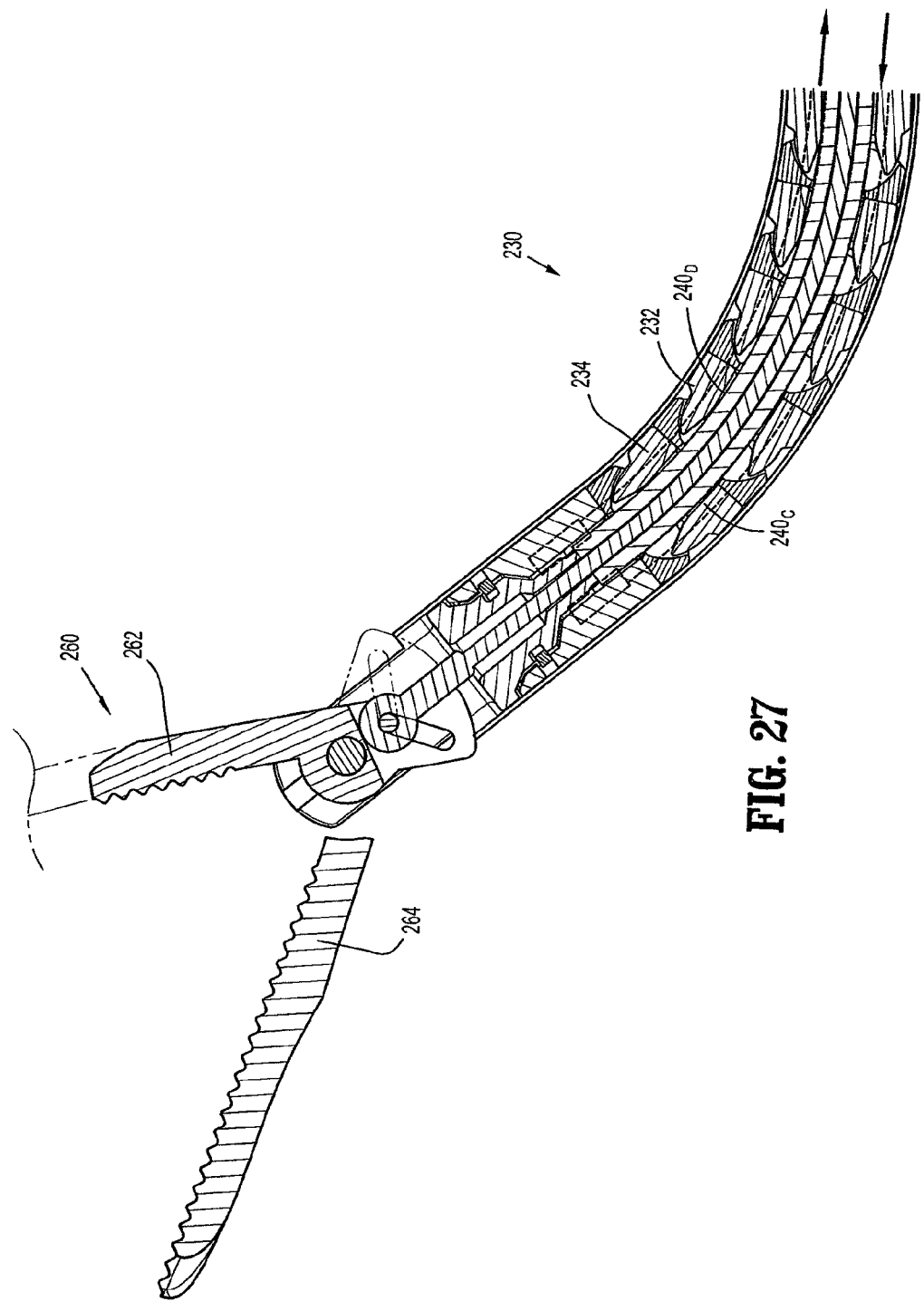
FIG. 27 is a side cross-sectional view of the end effector and the articulation section of the surgical device of FIG. 1, showing the articulating section in an articulated position.

Referring to FIGS. 26 and 27, surgical device 100 allows an operator to articulate articulating section 230 relative to longitudinal axis "X" (FIG. 2) with only one hand. In use, the operator grabs handle assembly 300 with one hand. For example, the operator may place the thumb in movable thumb loop 301 (FIG. 9) and some of the other fingers in finger loop 302 (FIG. 9). Once the operator has grabbed handle assembly 300, the operator moves the wrist to articulate handle assembly 300 relative to elongate outer tube 210 and ball 331. The operator may articulate handle assembly in any direction.

FIG. 26, for example, shows handle assembly 300 articulated upwardly with respect to the elongate outer tube 210 (see also FIG. 3). Handle assembly 300, however, may be articulated downwardly or laterally, as shown in FIG. 5. Regardless of the articulation direction, articulating handle assembly 300 with respect to elongate outer tube 210 causes the articulation of articulating section 230, as seen in FIGS. 3 and 5. Articulating section 230 mirrors the movement of handle assembly 300 and articulates relative to elongate outer tube 210 in the same direction as handle assembly 300.

For instance, when the operator articulates handle assembly 300 upwardly with respect to elongate outer tube 210, one articulation cable $240_D$ moves proximally while another articulation cable $240_C$ moves distally. As a results, articulation cable $240_D$ tightens, while articulation cable $240_C$ slacks. In particular, articulation cable plate 311 moves along with handle assembly 300 upon articulation of handle assembly 300 while ball 331 remains stationary relative to elongate outer tube 210. Since articulation cable plate 311 is attached to articulation cables 240, moving articulation cable plate 311 causes articulation cables 240 to move. When articulation cable plate 311 is slanted upwardly relative to ball 331, an articulation cable $240_C$ move distally, while articulation cable $240_D$ moves proximally, as depicted in FIG. 26.

As seen in FIG. 27, the combination of a proximal motion by one articulation cable $240_D$ and the distal motion by articulation cable $240_C$ causes articulating section 230 to articulate upwardly relative to longitudinal axis "X" (FIG. 2). As explained above, articulation cables $240_C$, $240_D$ change positions along elongate outer tube 210. (See FIGS. 18 and 19). Although articulation cable $240_C$ is positioned above articulation cable $240_D$ at the proximal end 212 (FIG. 2) of elongate outer tube 210, articulation cables $240_C$, $240_D$ switch positions at some point along elongate outer tube 210. As a result, articulation cable 240C is positioned below articulation cable 240D at the distal end 214 (FIG. 2) of elongate outer tube 210 and in articulating section 230 (FIG. 27). Therefore, a distal translation of articulation cable $240_C$ allows articulation cable $240_C$ to slack, thereby loosening a lower portion of articulating section 230. Conversely, a proximal translation of articulation cable $240_D$ causes tightening on articulation cable 240D, compressing an upper portion articulating section 230. As a result of the compression of an upper portion of articulating section 230, articulating section 230 articulates upwardly relative to longitudinal axis "X" (FIG. 2). The operator may similarly articulate articulating section 230 downwardly or laterally by moving handle assembly 300 with respect to longitudinal axis "X" (FIG. 2). Upon movement of handle assembly 300 with respect to longitudinal axis "X," articulating section 230 articulates in the same direction as handle assembly 300.

Figure 28:
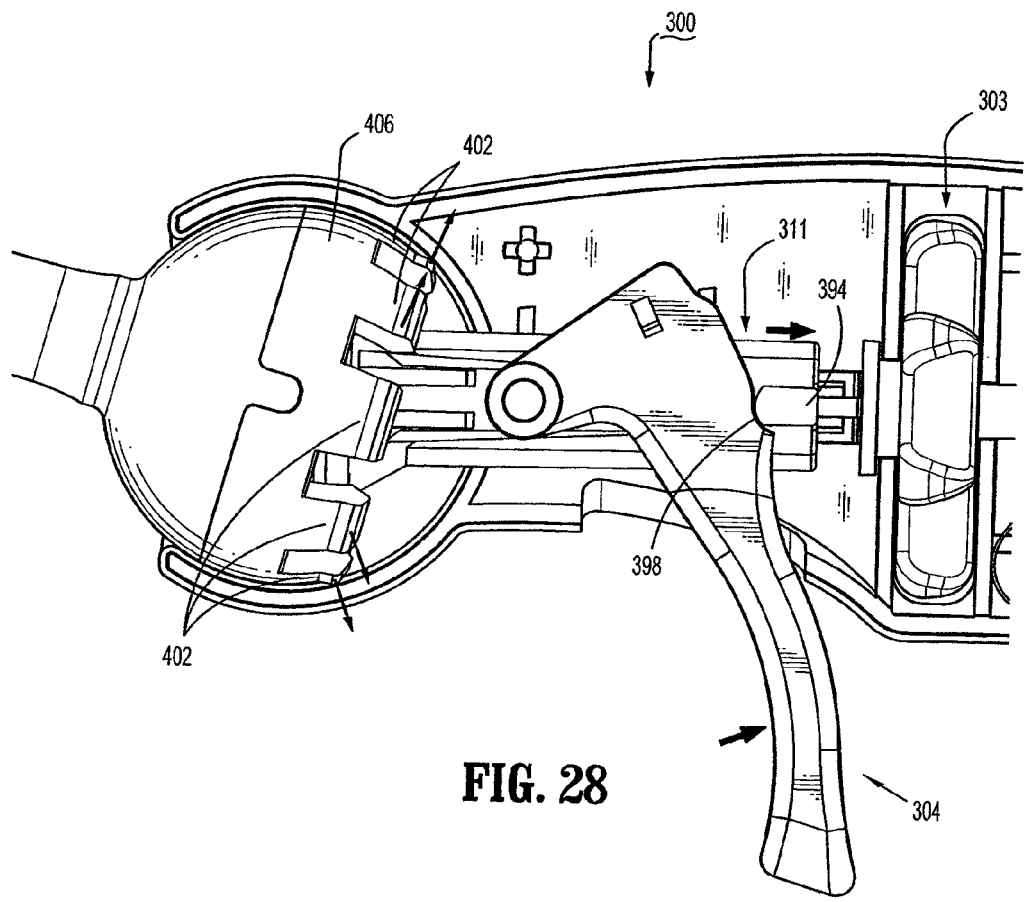
FIG. 28 is a side cutaway view of a portion of the articulation mechanism of the surgical device of FIG. 1, showing an articulation lock trigger being actuated.
Figure 29:
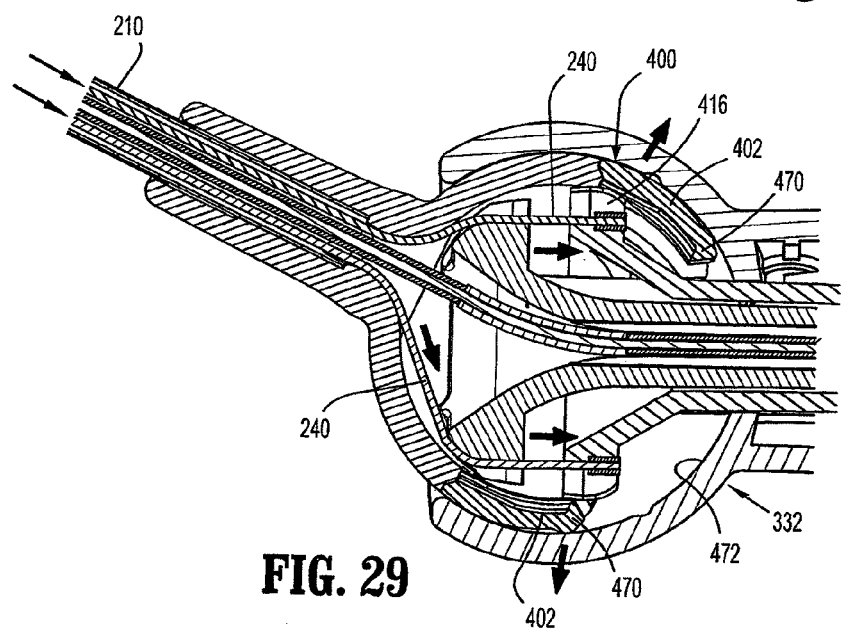
FIG. 29 is a side cross-sectional view of a portion of the articulation mechanism of the surgical device of FIG. 1, depicting articulation cables moving proximally in response to an actuation of the articulation lock trigger shown in FIG. 28.

Referring to FIGS. 28 and 29, the operator can fix the position of articulating section 230 by actuating articulation lock trigger 304. To actuate articulation lock trigger 304, the operator moves articulation lock trigger 304 toward rotation wheel 303, as shown in FIG. 28. Upon actuation of articulation lock trigger 304, detent recess 398 engages detent 394 of articulation cable plate 311, urging articulation cable plate 311 in a proximal direction. As articulation cable plate 311 moves proximally, cable engaging portion 416 of pushes fingers 402 of articulation lock ring 400 outwardly toward inner surface 472 of cup 332. When fingers 402 flex outwardly, detents 470 of fingers 402 frictionally engage inner surface 472 of cup 322, thereby locking the position of handle assembly 300 with respect to elongate outer tube 210 and ball 331. In addition, the proximal translation of articulation cable plate 311 causes all articulation cables 240 to move proximally. As a consequence of this proximal motion, all articulation cables 240 are tightened, compressing articulation links 232, 234 together. Therefore, the compressed articulation links 232, 234 fix the position of articulating section 230 (FIG. 27) relative to elongate outer tube 210.

Figure 30:
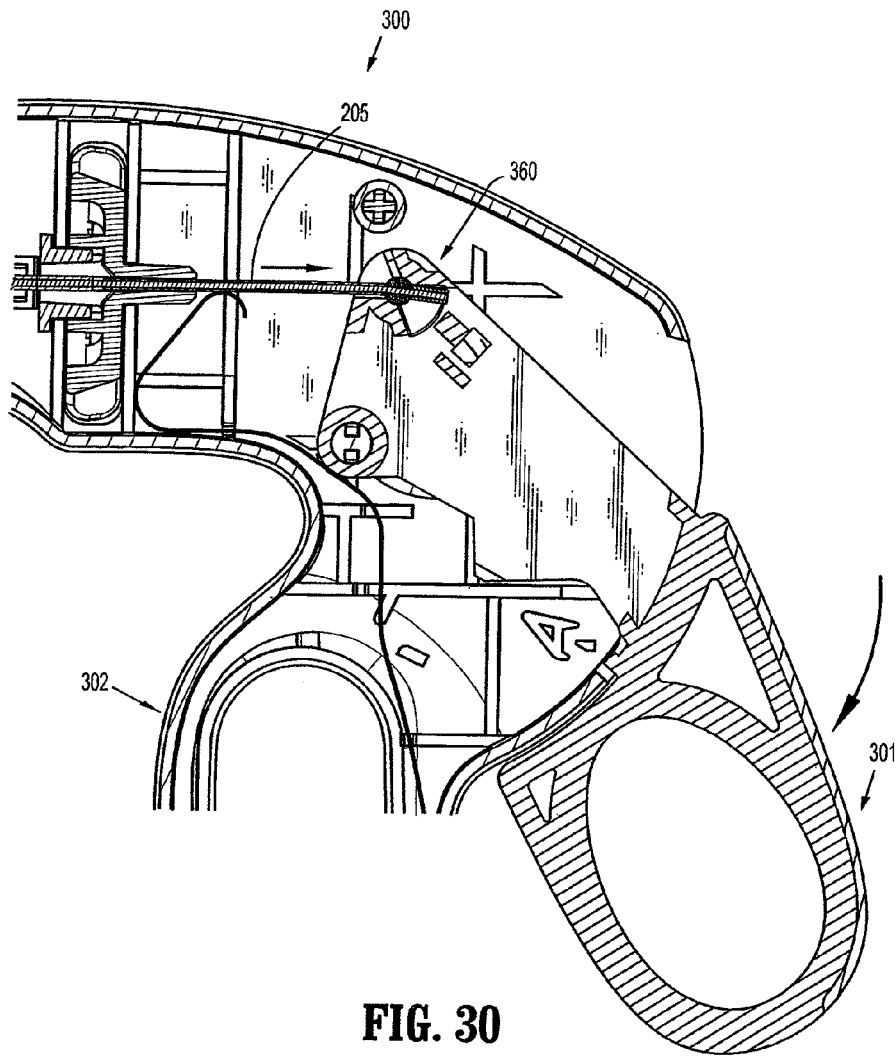
FIG. 30 is a side cross-sectional view of a portion of the handle assembly of the surgical device of FIG. 1, showing a movable thumb loop being actuated.

With reference to FIGS. 30 and 31, the operator can move first and second jaw members 262, 264 between an open position (FIG. 27) and an approximated position (FIG. 31) by actuation of movable thumb loop 301. To actuate end effector 260, the operator moves movable thumb loop 301 toward finger loop 302, as shown in FIG. 30. Since distal end portion 360 of movable thumb loop 301 is operatively connected to actuation cable 205, the actuation of movable thumb loop 301 causes the proximal translation of actuation cable 205. As actuation cable 205 moves proximally, coupling member 436, which interconnects end effector 260 and actuation cable 205, urges pin 440 proximally. The proximal motion of pin 440 along cam slots 442, 444 urges first and second jaw members 262, 264 toward each other. An operator may initial place tissue between first and second jaw members 262, 264 while end effector 260 is in the open position and then move first and second jaw members 262, 264 to the approximated position to clamp the tissue.

FIGS. 32 and 33 show an embodiment of surgical device 100 substantially similar to the embodiments depicted in FIGS. 1-4, except for end effector 1260. End effector 1260 includes first and second shearing blades 1262, 1264 configured to mechanically or electromechanically cut tissue. First and second shearing blades 1262, 1264 are electrically isolated from one another and are adapted to move between an open position and an approximated position.

With reference to FIGS. 34 and 35, although coupling member 222 connects articulating section 230 to end effector 1260, end effector 1260 additionally includes a clevis coupler 1500. Clevis coupler 1500 is attached to actuation cable 205 and includes two legs 1538, 1540 extending distally therefrom. First and second legs 1538, 1540 define a space therebetween dimensioned to receive proximal portions 1572, 1574 of first and second shearing blades 1262, 1264. Each leg 1538, 1540 defines a hole 1548, 1550 adapted to receive a pin 1580. Pin 1580 is also configured to be slidably received in cam slots 1442, 1444 of first and second shearing blades 1262, 1264. Cam slot 1442 is defined along a proximal portion 1572 of shearing blade 1262, whereas cam slot 1444 is defined along a proximal portion 1574 of shearing blade 1264. A disk made 1600 of electrically insulating material electrically isolates shearing blades 1262, 1264 from each other. As seen in FIG. 34, disk 1600 is positioned between first and second shearing blades 1262, 1264 and defines a hole 1602 configured to receive pin 1580.

Figure 38:
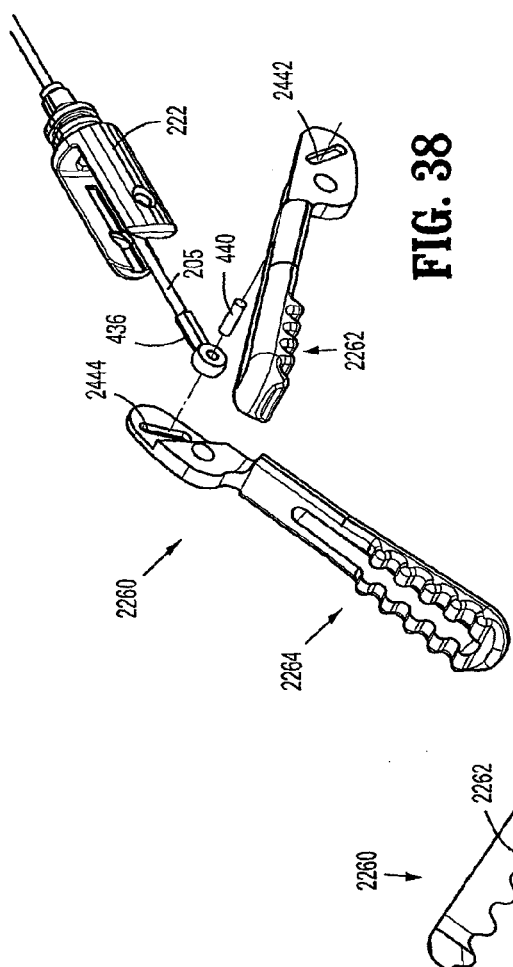
FIG. 38 is a perspective exploded view of the end effector of the surgical device of FIG. 36.

FIGS. 37 and 38 depict another embodiment of surgical device 100. The structure and operation of this embodiment is substantially similar to the embodiment shown in FIGS. 1-5. This embodiment of surgical device 100 includes an end effector 2260 configured for grasping tissue. End effector 2260 includes first and second grasping forceps 2262, 2264 configured to grasp tissue. Although the drawings of this embodiment show surgical device 100 without a post 350 (FIG. 10A), this embodiment of surgical device 100 may include a post 350 for electrically coupling end effector 2226 to a generator. First and second grasping forceps 2262, 2264 are configured to move between an open position and an approximated position. Each of the first and second grasping forceps 2262, 2264 includes a tissue engaging surface 2266, 2268. Both tissue engaging surfaces 2266, 2268 includes a plurality of teeth 2272, 2274 for engaging tissue.

Figure 39:
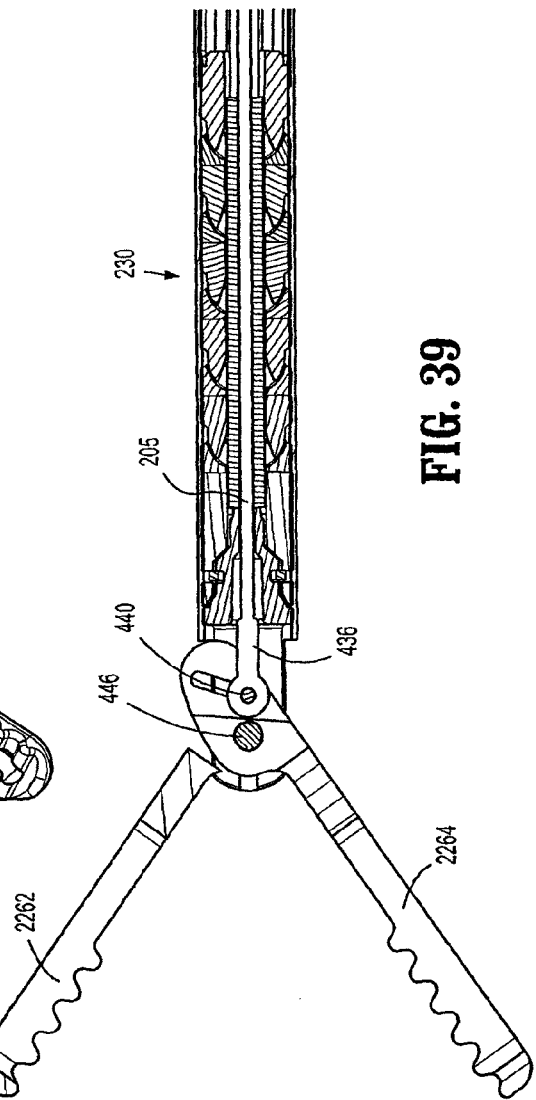
FIG. 39 is a side cross-sectional view of an articulating section and the end effector of the surgical device of FIG. 36.
Figure 40:
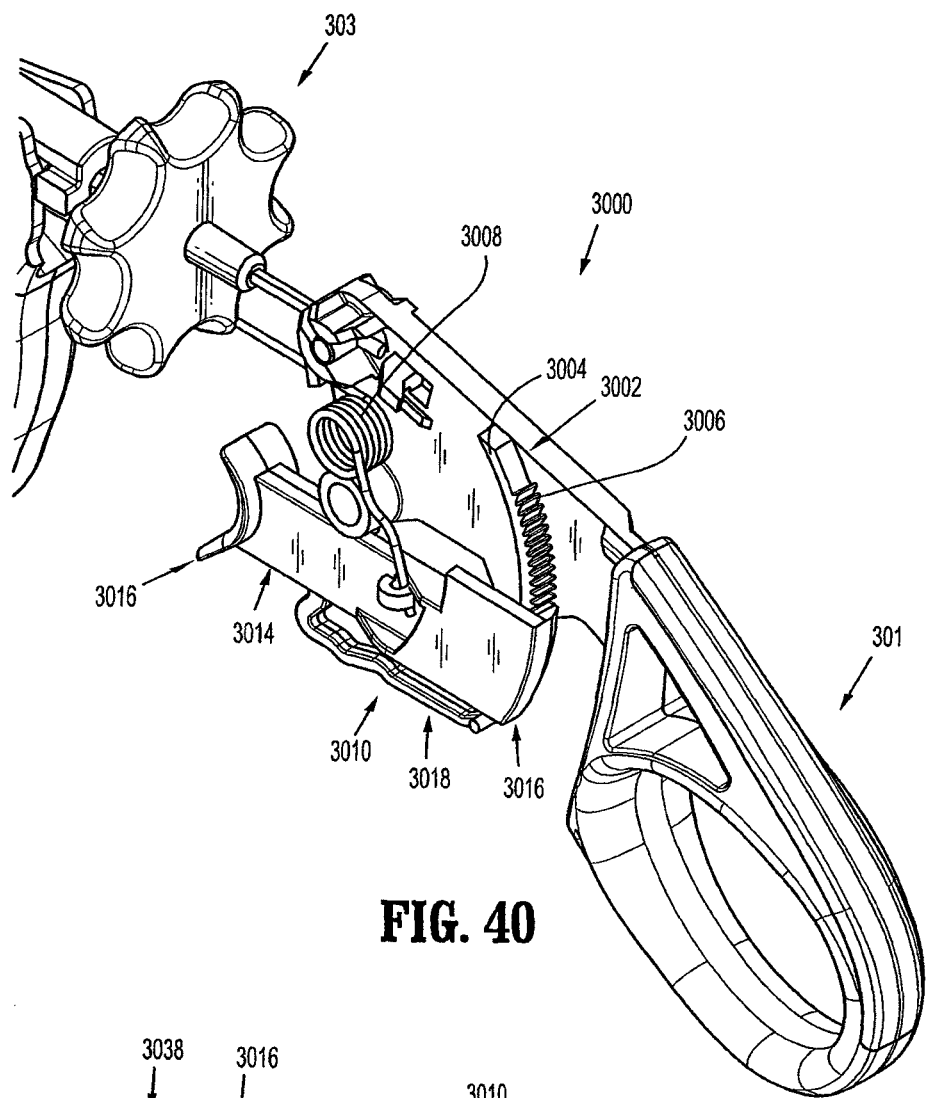
FIG. 40 is a perspective view of a locking mechanism for any of the embodiments of the surgical device shown above.
Figure 41:
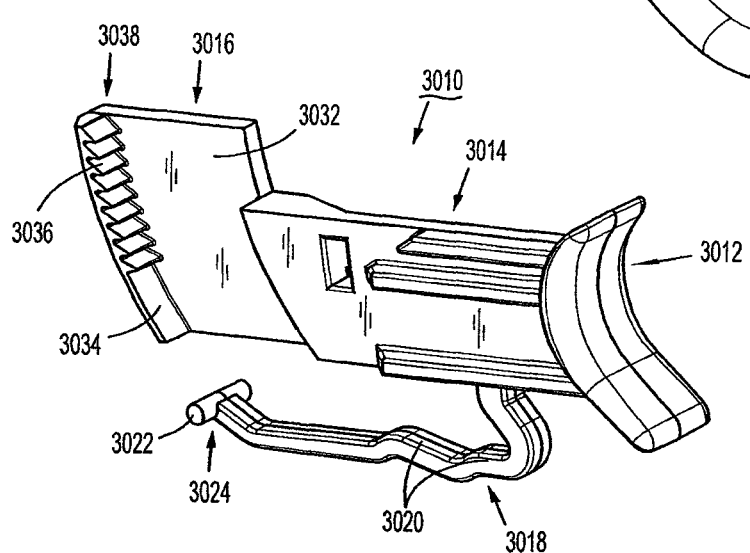
FIG. 41 is a perspective view of a release assembly of the locking mechanism of FIG. 40.

With reference to FIGS. 38 and 39, first and second grasping forceps 2262, 2664 are pivotally connected to each other by pivot pin 446. End effector 2260 is operatively coupled to actuation cable 205 through coupling 436 and pin 440. Each of the first and second grasping forceps 2262, 2264 includes cam slots 2442, 2444 adapted for slidably receiving pin 440. Such connection allows first and second grasping forceps 2262, 2264 to move to the approximated position upon a proximal motion of actuation cable 205.

Referring to FIGS. 40-43, any of the embodiments of surgical device 100 may include a locking mechanism 3000 for fixing the relative position of first and second jaw members 262, 264. As discussed above, movable thumb loop 301 is operatively coupled to first and second jaw members 262, 264. In operation, pivoting movable thumb loop 301 toward finger loop 301 causes first and second jaw members 262, 264 to move from the open position and the approximated position. (See FIGS. 30 and 31). Thus, maintaining movable thumb loop 301 close to finger loop 302 would keep first and second jaw members 262, 264 in the approximated position. In use, locking mechanism 3000 can maintain thumb loop 301 close to finger loop 302 to fix first and second jaw members 262, 264 in the approximated position. In some embodiments, locking mechanism 3000 includes a first ratchet assembly 3002 attached to the movable thumb loop 301. Specifically, first ratchet assembly 3002 is attached to the lateral wall of a portion of movable thumb loop located inside handle assembly 300. First ratchet assembly 3002 includes a curved column 3004 and a plurality of teeth 3006 extending proximally from curved column 3004. Each tooth 3006 is angled upwardly relative to movable thumb loop 301.

Locking mechanism 3000 further includes biasing member 3008, such as a spring, secured to a portion of movable thumb loop 301 located within handle assembly 300 and operatively coupled to a release assembly 3010. Biasing member 3008 biases release assembly 3010 in a distal direction. In the depicted embodiment, biasing member 3008 is a torsion spring. It is contemplated, however, that biasing member 3008 may be any apparatus or means suitable for biasing release assembly 3010 distally.

Release assembly 3010 includes a trigger 3012 adapted to receive a finger, an elongate section 3014 extending proximally from trigger 3012, a second ratchet assembly 3016 configured to securely engage first ratchet assembly 3002, and a guiding bar 3018 protruding from a lower portion of elongate section 3014.

Guiding bar 3018 has camming surfaces 3020 and transverse pin 3022 disposed at a proximal end 3024 thereof. Camming surfaces 3020 are configured to slidably engage projections 3026, 3028 of handle assembly 300 (FIGS. 42 and 43) to guide the translation of release assembly 3010 through handle assembly 300. Transverse pin 3022 is configured to engage a mechanical stop 3030 disposed inside handle assembly 300 to prevent, or at least inhibit, further proximal advancement of release assembly 3010.

Figure 62:
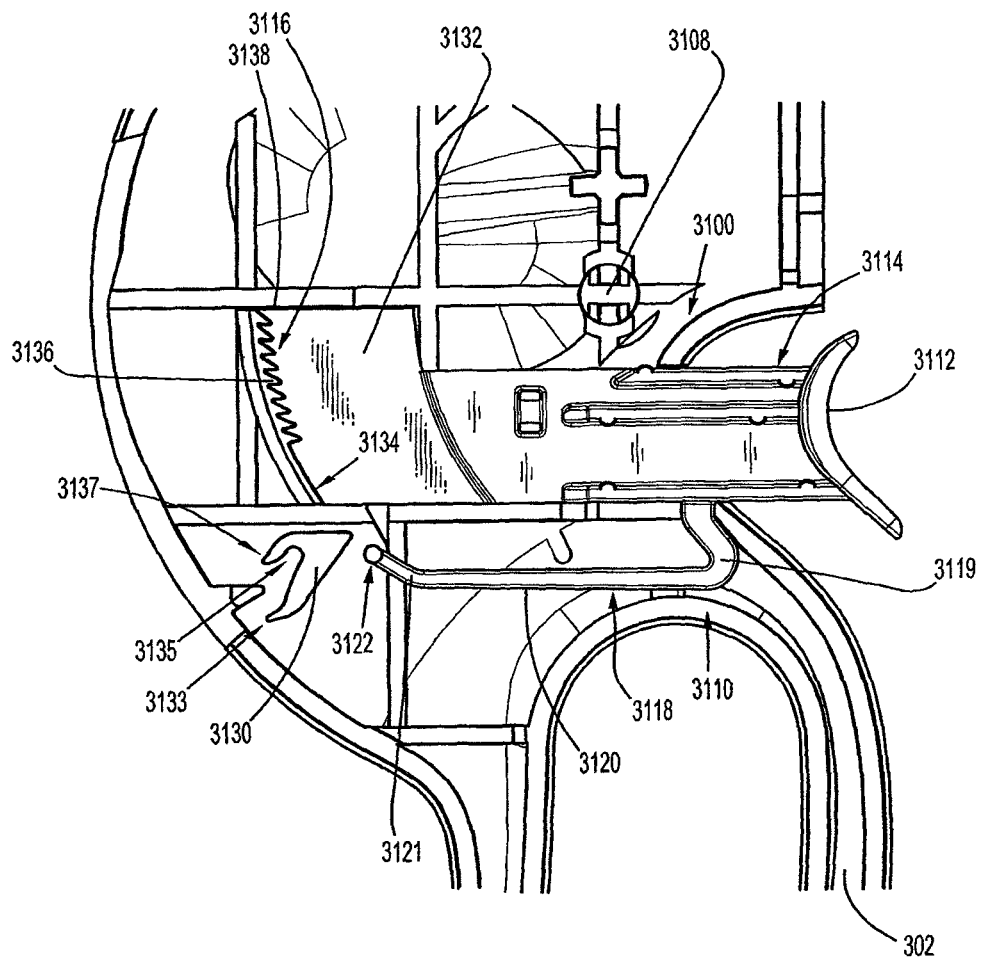
FIG. 62 is a side cross-sectional view of a further embodiment of a locking mechanism for any of the embodiments of the surgical device shown above, wherein the locking mechanism is shown in a locked position.
Figure 63:
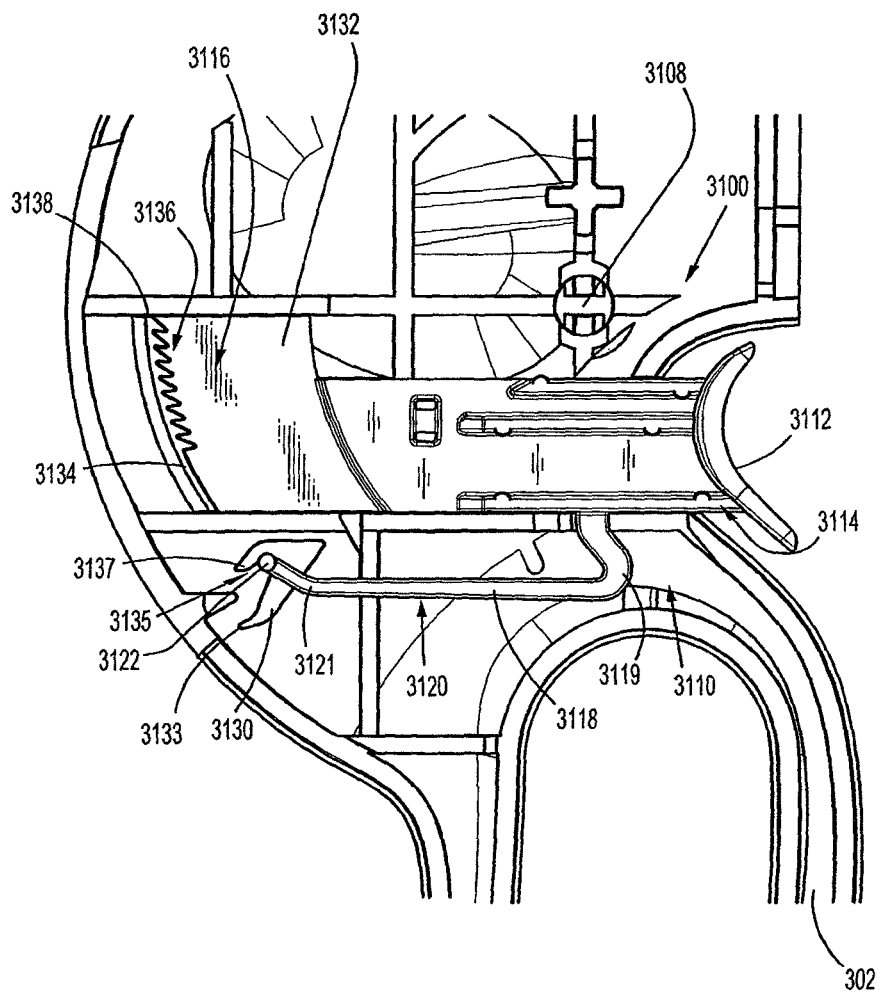
FIG. 63 is a side cross-sectional view of the locking mechanism of FIG. 62 shown in an unlocked position.
Figure 64:
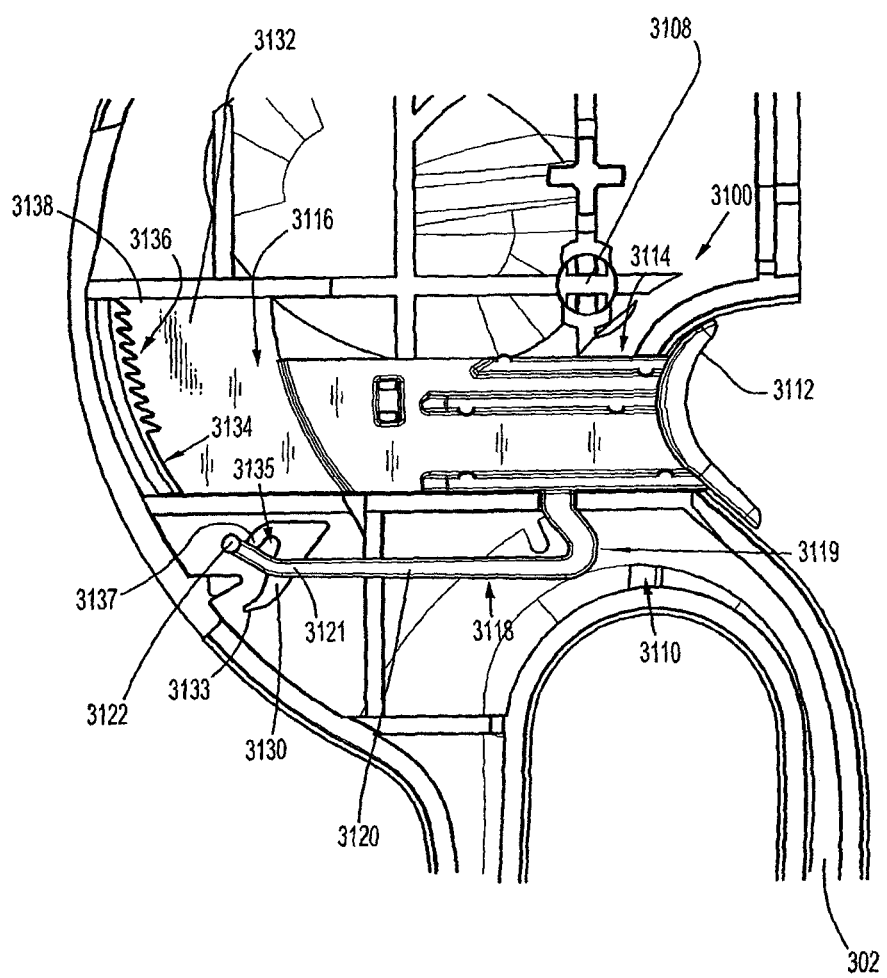
FIG. 64 is a side cross-sectional view of the locking mechanism of FIG. 62 transitioning between the unlocked position and the locked position.

Turning momentarily to FIGS. 62-64, a locking mechanism 3100 according to another embodiment of the present disclosure is shown. Locking mechanism 3100 includes a release assembly 3110 having a trigger 3112, an elongate section 3114, a second ratchet assembly 3116 configured to engage the first ratchet assembly (see FIGS. 42-43) and a guiding bar 3118 extending from elongate section 3114. Guiding bar 3118 includes a proximal portion 3119 extending from elongate section 3114, a longitudinally extending portion 3120 and a distal portion 3121 extending from proximal portion 3119. The distal portion 3121 of guiding bar 3118 includes a transverse pin 3122 that is configured and dimensioned to cam along and engage a stop member 3130 during translation of guiding bar 3118 between the locked and the unlocked position.

Longitudinally extending portion 3120 remains substantially parallel to elongate section 3114 when locking mechanism 3100 is in the locked position (FIG. 62) and when locking mechanism 3100 is in the unlocked position (FIG. 63). This substantially parallel configuration of longitudinally extending portion 3120 corresponds to an un-stressed position of guiding bar 3118. Alternatively, longitudinally extending section 3120 of guiding bar 3118 may be configured such that longitudinally extending section 3120 is disposed at a predetermined angle with respect to elongate section 3114 in both the locked and the unlocked position so long as the predetermined angle corresponds to an un-stressed state of guiding bar 3118. In other words, the configuration of release assembly 3110 and stop member 3130 allow guiding bar 3118 to be maintained in an un-stressed state in both the locked and the unlocked position. As can be appreciated, with guiding bar 3118 in an un-stressed state in both of the stable positions, i.e., the locked position and the unlocked position, the flexibility, resiliency, and durability of guiding bar 3118 is not affected by prolonged disposition of locking mechanism 3100 in either the locked or the unlocked position.

As discussed above, both embodiments of the release assembly, e.g., release assembly 3010 (FIGS. 40-43) and release assembly 3100 (FIGS. 62-64), include a second ratchet assembly 3016, 3116 configured to engage first ratchet assembly 3002. Second ratchet assembly 3016, 3116 includes a wall 3032, 3132 extending proximally from elongate section 3014, 3114 and a curved column 3034, 3134 positioned along a proximal end 3038, 3138 of wall 3032, 3132. A plurality of teeth 3036, 3136 protrude distally from at least a portion of curved column 3034, 3134. Teeth 3036, 3136 are adapted to securely engage teeth 3006 of first ratchet assembly 3002. In some embodiments, teeth 3036, 3136 are angled downwardly with respect to movable thumb loop 301. When teeth 3036, 3136 of second ratchet assembly 3016, 3116 engage teeth 3006 of first ratchet assembly 3002, the position of movable thumb loop 301 is fixed relative to finger loop 302. (See FIG. 42).

In operation, an operator can utilize the locking mechanism 3000, 3100 to fix the relative position of first and second jaw members 262, 264 (FIG. 31). Initially, the locking mechanism 3000, 3100 is in the locked position (see FIGS. 42, 62), such that at least a portion of teeth 3006 of first ratchet 3002 are engaged with at least a portion of teeth 3036, 3136 of second ratchet 3016, 3116. As the operator moves movable thumb loop 301 toward finger loop 302, to move first and second jaw members 262, 264 (FIG. 31) toward the approximated position, teeth 3006 of first ratchet assembly 3002 further engage teeth 3036, 3016 of second ratchet assembly 3016, 3116.

Figure 42:
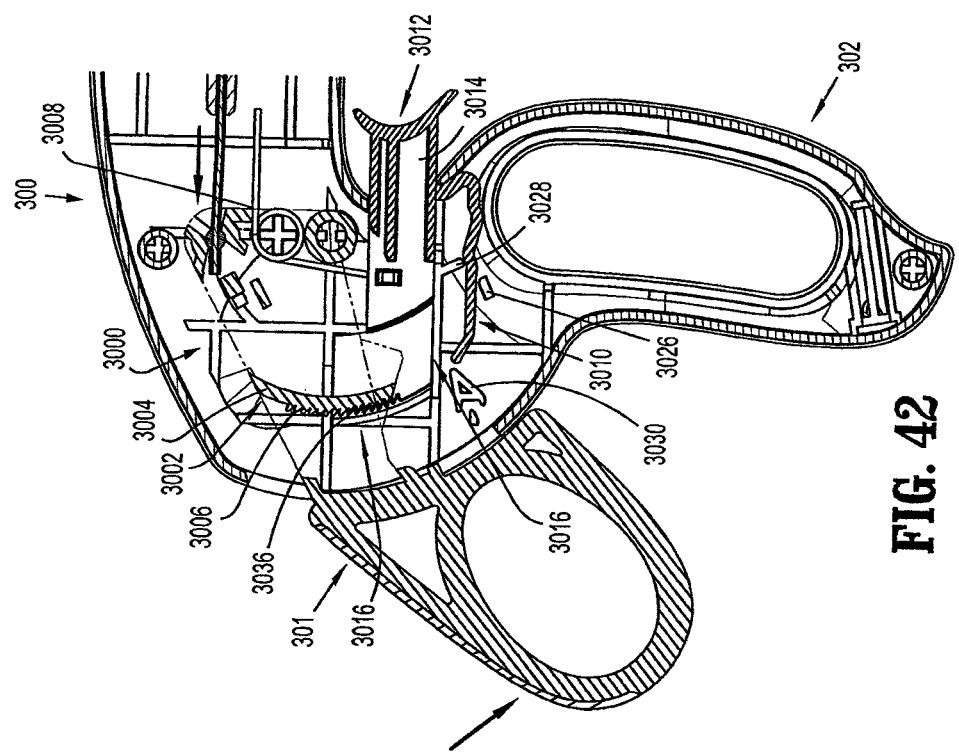
FIG. 42 is a side cross-sectional view of the locking mechanism of FIG. 40 in a locked position.

The orientation of teeth 3006 and teeth 3036, 3136 precludes, or at least hinders, movable thumb loop 301 from moving away from finger loop 302 while allowing movable thumb loop 301 to move further toward finger loop 302. In other words, teeth 3006 of first ratchet assembly 3002 and teeth 3036, 3136 of second ratchet assembly 3016, 3116 are configured as a one-way ratchet. Accordingly, the locking mechanism 3000, 3100, when in the locked position, may be used to incrementally fix the position of movable thumb loop 301 relative to finger loop 302, as shown in FIG. 42. Since movable thumb loop 301 is operatively connected to first and second jaw members 262, 264 (FIG. 31), the relative position of first and second jaw members 262, 264 is incrementally fixed when locking mechanism 3000, 3100 fixes the position of movable thumb loop 301 with respect to finger loop 302. As can be appreciated, the operator may further advance movable thumb loop 301 toward finger loop 302 until first and second jaw members 262, 264 (FIG. 31) reach the approximated position. At this point, the locking mechanism 3000, 3100 operates to fix the first and second jaw members 262, 264 (FIG. 31) in the approximated position.

Figure 43:
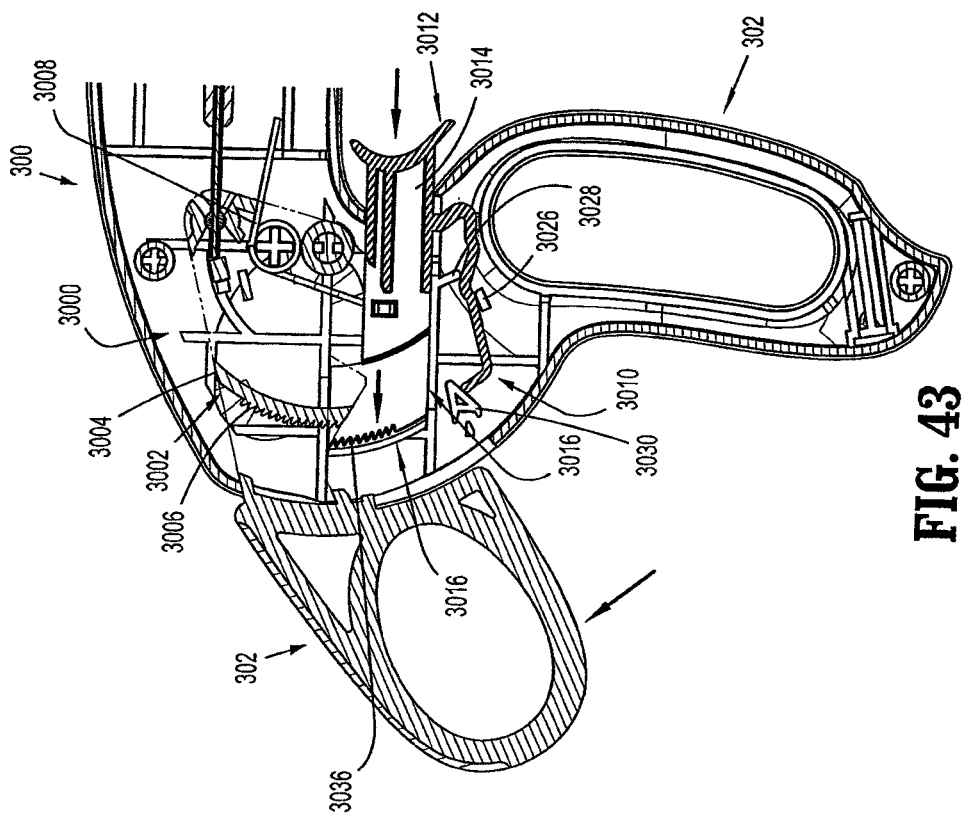
FIG. 43 is a side cross-sectional view of the locking mechanism of FIG. 40 in an unlocked position.

To release movable thumb loop 301, the operator presses the trigger 3012, 3112 proximally against the influence of biasing member 3008, 3108. When trigger 3012, 3112 moves proximally, elongate section 3014, 3114 and guiding bar 3018, 3118 are translated proximally. Simultaneously, teeth 3036, 3136 of second ratchet assembly 3016, 3116 are moved proximally, disengaging teeth 3002 of first ratchet assembly 3002. Consequently, movable thumb loop 301 moves away from finger loop 302 under the influence of biasing member 3008, 3108 thereby moving first and second jaw members 262, 264 toward the open position, as shown in FIG. 43. (See also FIG. 20).

Upon further pressing of trigger 3012, 3112, guiding bar 3018, 3118 is translated proximally such that transverse pin 3022, 3122 cams along a surface of stop member 3030, 3130 (see FIG. 43) and around lower flange 3133 (FIGS. 62-64). Upon release of trigger 3012, 3112, due to the configuration of stop member 3030, 3130, transverse pin 3022, 3122 is pulled distally under the bias of biasing member 3008, 3108 into groove 3135 (see FIG. 63). More specifically, the engagement of transverse pin 3022, 3122 within groove 3135 of stop member 3130 prevents guiding bar 3018, 3118 from returning fully distally under the bias of biasing member 3008, 3108 to the locked position. Groove 3135 of stop member 3130 retains guiding bar 3018, 3118 in a proximal, or unlocked position wherein teeth 3036, 3136 of second ratchet 3016, 3116 are spaced apart, or disengaged, from teeth 3006 of first ratchet 3002. When locking mechanism 3000, 3100 is in this unlocked position, moveable thumb loop 301 may still be moved toward finger loop 302 to move first and second jaw members 262, 264 (FIG. 31) toward the approximated position. However, since the teeth 3036, 3136 of second ratchet 3016, 3116 and teeth 3006 of first ratchet 3002 are disengaged in the unlocked position, the position of the moveable thumb loop 301, and thus the relative position of the first and second jaw members 262, 264 (FIG. 31), is not incrementally fixed by the locking mechanism 3000, 3100.

As mentioned above, and as shown in FIG. 63, guiding bar 3118 is in an un-stressed position when transverse pin 3122 is engaged within groove 3135 of stop member 3130. More specifically, groove 3135 of stop member 3130 is dimensioned and positioned such that distal portion 3121 of guiding bar 3118 is not deflected (either upwardly or downwardly) when transverse pin 3122 is engaged within groove 3135. In other words, guiding bar 3118 is maintained at a fixed angle, or position, e.g., substantially parallel, with respect to elongate section 3114, when in the locked position and in the unlocked position. Maintaining guiding bar 3118 in an un-stressed state maintains the resiliency and durability of guiding bar 3118, allowing transverse pin 3122 to accurately and consistently cam along stop member 3130 and over lower flange 3133 into groove 3135 and from groove 3135 over upper flange 3137, as is required during repeated locking and unlocking of the locking mechanism 3100.

In order to re-lock the locking mechanism 3000, 3100 trigger 3012, 3112 is once again pressed. As trigger 3012, 3112 is once again pressed, guiding bar 3018, 3118 is translated proximally from the unlocked position (FIG. 63) toward the locked position (FIG. 64). More specifically, transverse pin 3022, 3122 is translated proximally from groove 3135 of stop member 3130 and around upper flange 3137 (FIG. 64). The translation of transverse pin 3022, 3122 around upper flange 3137 releases, or frees transverse pin 3022, 3122 from groove 3135 of stop member 3130. Accordingly, upon release of trigger 3012, 3112, transverse pin 3022, 3122 and thus guiding bar 3018, 3118 are returned to the proximal, or locked position (FIG. 62) under the bias of biasing member 3008, 3108. Simultaneously, teeth 3036, 3136 of second ratchet assembly 3016, 3116 are brought into engagement with teeth 3006 of first ratchet assembly 3002. Thus, with the locking mechanism 3000, 3100 back in the locked position, the relative position of first and second jaw members 262, 264 (FIG. 31) may once again be fixed.

Figures 44, 45, 46:
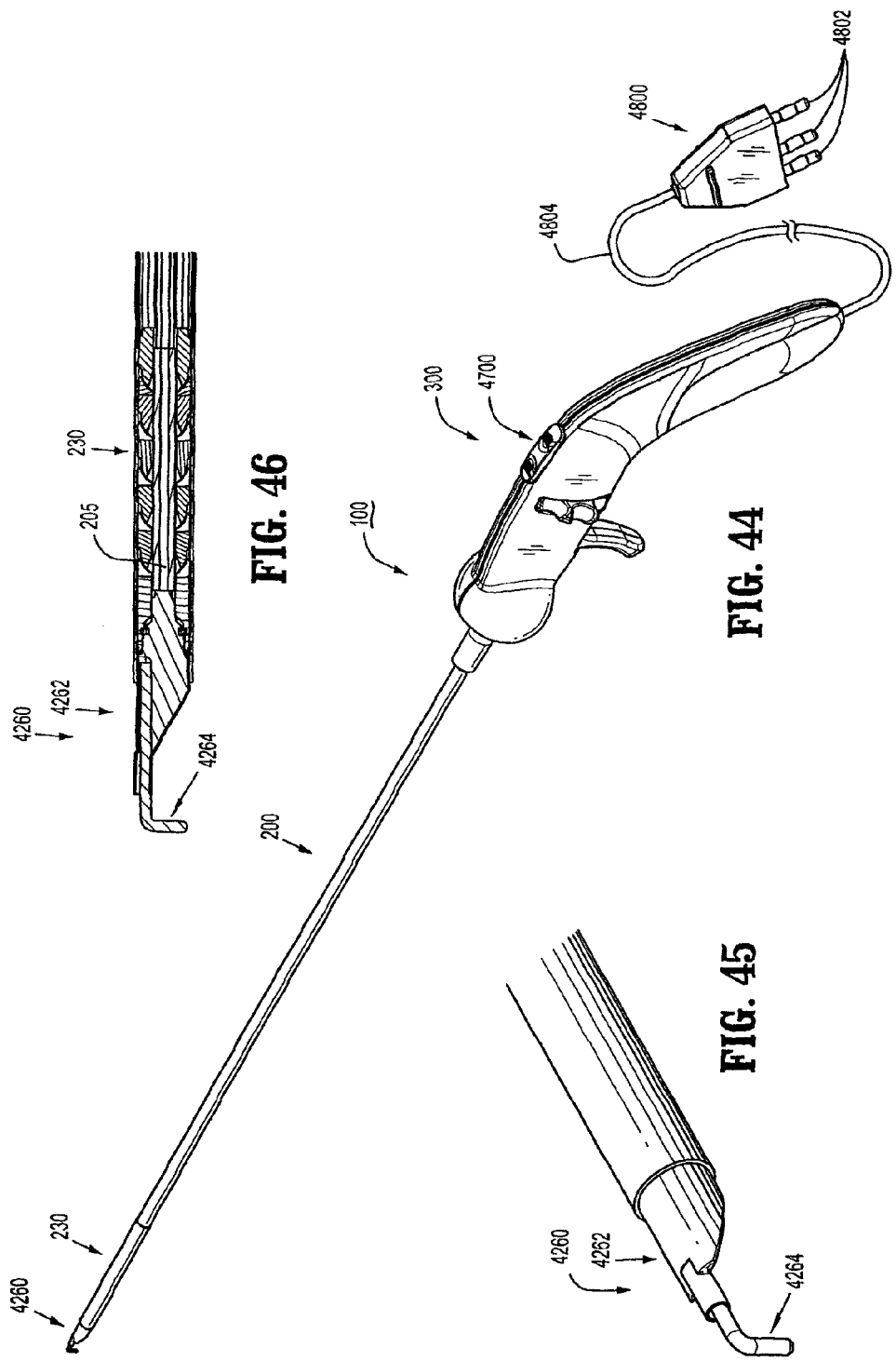
FIG. 44 is a perspective view of a surgical device according to another embodiment of the present disclosure, showing an end effector having a probe.
FIG. 45 is a perspective view of the end effector and a portion of an articulating section of the surgical device of FIG. 44.
FIG. 46 is a side cross-sectional view of the end effector and the articulating section of the surgical device of FIG. 44.

FIGS. 44-46 show another embodiment of surgical device 100. The operation and structure of this embodiment of surgical device 100 is substantially similar to the embodiments described above. In this embodiment, surgical device 100 includes an end effector 4260 including an electrode assembly 4262. Electrode assembly 4262 includes at least one probe or electrode 4264 adapted to conduct and apply electrosurgical energy to tissue. In the depicted embodiment, electrode assembly 4262 has one probe 4264 having a hook-like shape. Probe 4264, however, may have any suitable shape or configuration. Regardless of its shape, probe 4264 is electrically linked to actuation cable 205 of surgical device 100, as shown in FIG. 46.

With continued reference to FIGS. 44-46, this embodiment of surgical device 100 includes an electrical switch 4700 supported on handle assembly 300. Electrical switch 4700 is configured to set surgical device 100 to one of a number of modes of operation, such as cutting, blending, and/or coagulating. More specifically, electrical switch 4700 is adapted to vary the waveform and/or amount of energy that is delivered from the source of electrosurgical energy to electrode assembly 4262. In several embodiments, electrical switch 4700 has two discrete positions. In a first discrete position, electrical switch 4700 sets surgical device 100 to transmit "a cutting waveform" output to electrode assembly 4262 and, in a second discrete position, electrical switch 4700 sets surgical device 100 to transmit a "coagulating waveform" output to electrode assembly 4262. It is envisioned that electrical switch 4700 may also include some measure of tactile feedback capable of being felt by the operator and/or some measure of audible feedback produced by electrical switch 4700 (e.g., "click" sound).

In addition to electrical switch 4700, surgical device 100 includes an electrical interface or plug 4800 configured to be mechanically and electrically connected to a source of electrosurgical energy such as a generator. Plug 4800 includes a plurality of prongs 4802 adapted to mechanically and electrically coupled plug 4800 to a source of electrosurgical energy. An electrical cable 4804 electrically links plug 4800 with handle assembly 300.

Figure 47:
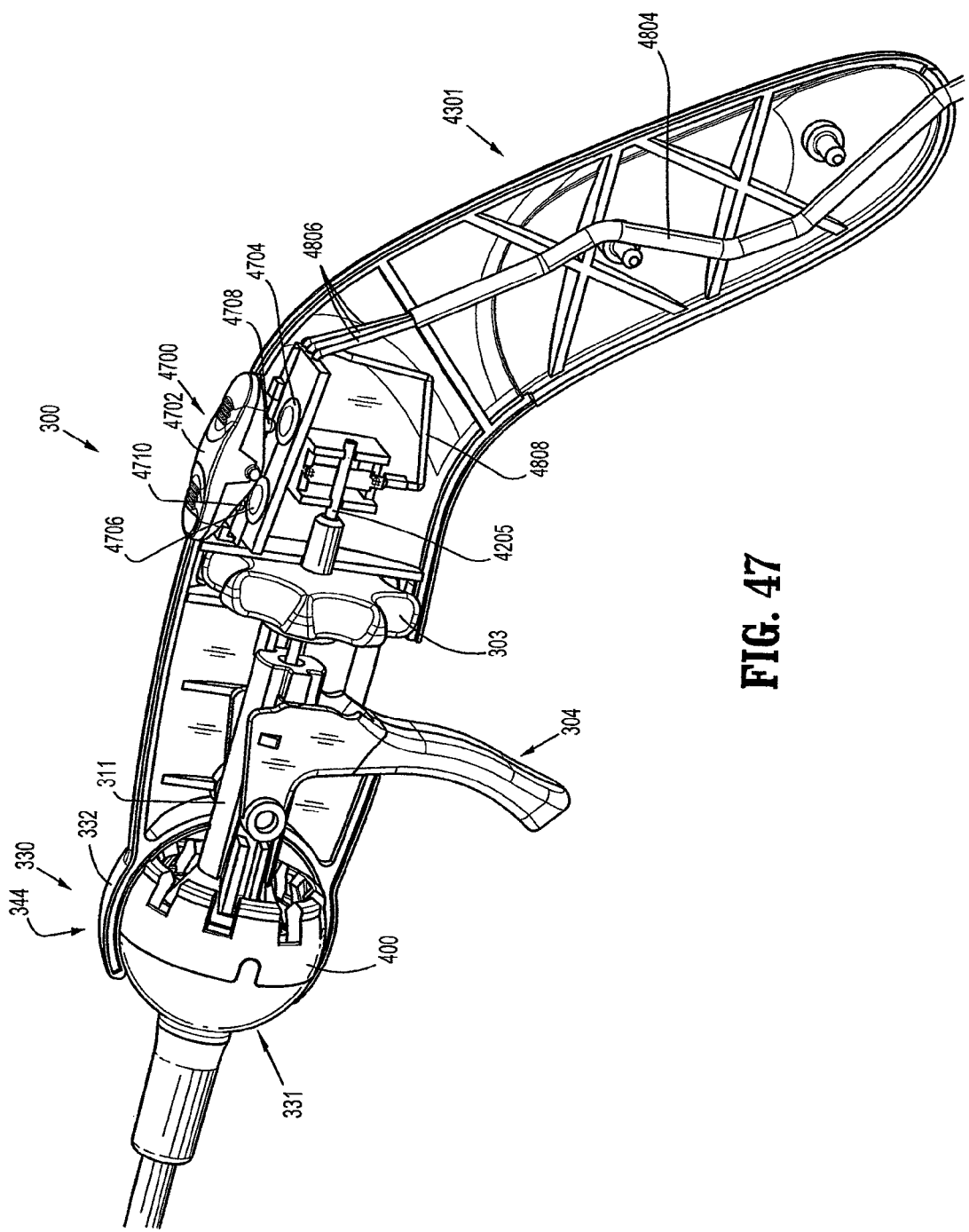
FIG. 47 is a side, cutaway view of a handle assembly of the surgical device of FIG. 44.

Referring to FIG. 47, this embodiment of surgical device 100 includes a stationary handle 4301 housing a portion of electrical cable 4804. Electrical cable 4804 encompasses a plurality of electrical wires 4806 configured to transmit electrosurgical energy from a source of electrosurgical energy (not shown). Electrical wires 4806 are electrically coupled to electrical switch 4700.

In the embodiment shown in FIG. 47, electrical switch 4700 includes a button 4702 configured to move between a first position and a second position and first and second transducers 4704, 4706. It is contemplate that transducers 4704, 4706 may be pressure transducers. Button 4702 includes first and second prongs 4708, 4710 extending downwardly toward first and second transducers 4704, 4706. When button 4702 is located in the neutral position, as shown in FIG. 47, first and second prongs 4708, 4710 are not in contact with first and second transducers 4704, 4706. Button 4702, however, may be moved between first and second positions. In the first position, first prong 4708 contacts and applies pressure to first transducer 4704. In response, first transducer 4704 converts this pressure into a signal that is transmitted to the electrosurgical generator (not shown) via electrical wires 4806. In turn, the electrosurgical generator transmits a corresponding amount of electrosurgical energy (such as RF energy) or an appropriate waveform output to electrode assembly 4262. As such, button 4702, in combination with first and second transducers 4704, 4706 allow the operator to control the amount of energy and/or waveform output of the electrosurgical generator (not shown) electrically coupled to surgical device 100. For example, when button 4702 is placed in the first position, a "cutting-type" waveform is selected. Conversely, when button 4702 is placed in the second position, second prong 4710 contacts and applies pressure to second transducer 4706. In turn, second transducer 4706 converts this pressure into a signal that is transmitted to the electrosurgical generator (not shown) via electrical wires 4806. In response to this signal, electrosurgical generator transmits a "cutting-type" waveform output to electrode assembly 4262. Accordingly, the operator can select the therapeutic effect desired by simply moving button 4702 between the first and second positions. It is envisioned that surgical device 100 may be deactivated (i.e., de-energized) when button 470 is in the neutral position.

Handle assembly 300 further includes an electrical wire 4808 electrically linking electrical switch 4700 and inner rod 4205. Inner rod 4205 is made of an electrically conductive material and electrically couples electrode assembly 4262 with an electrosurgical generator (not shown) connected to surgical device 100.

With continued reference to FIG. 47, this embodiment of surgical device 100 also includes articulation mechanism 330 operatively associated with articulating section 230 of endoscopic assembly 200. Articulating section 230 is configured to articulate towards a particular direction with respect to elongate outer tube 210 upon movement of handle assembly 300 toward the same direction with respect to elongate outer tube 210, as seen in FIGS. 48 and 49.

Figure 50:
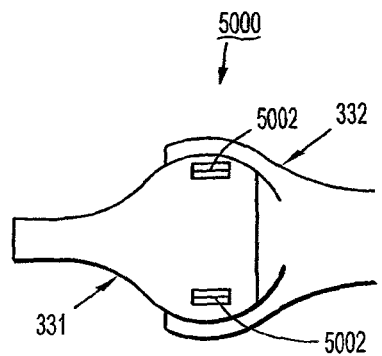
FIG. 50 is a side, cutaway view of an embodiment of a straightening mechanism for incorporation in any of the embodiments of the surgical device discussed above.
Figure 51:
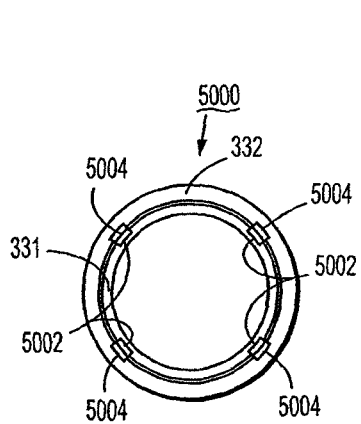
FIG. 51 is a front view of the straightening mechanism of FIG. 50.
Figure 52:
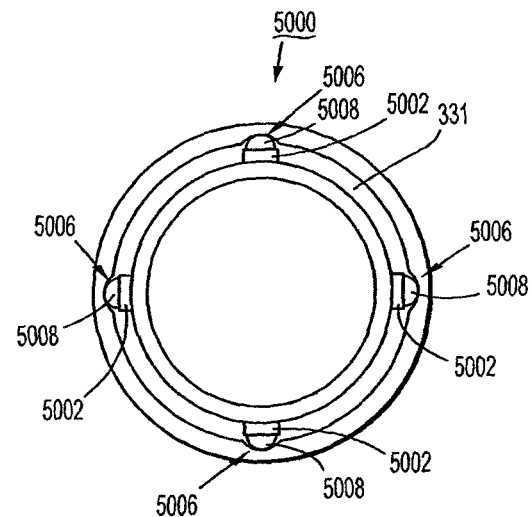
FIG. 52 is a front view of the straightening mechanism of FIG. 50 with detents for securing an articulation mechanism in a neutral position.

Referring to FIGS. 50-51, any of the embodiments of surgical device 100 may include a straightening mechanism 5000 for returning articulating section 230 (FIG. 2) into longitudinal alignment with elongate outer tube 210 (FIG. 2) after articulation. Straightening mechanism 5000 includes a first set of magnets 5002 attached to ball 331 and a second set of magnets 5004 attached to cup 332. It is envisioned that magnets 5002, 5004 may be rear earth magnets 5002. Magnets 5002, 5004 may be permanent magnets or electromagnets. In the embodiments where magnets 5002, 5004 are permanent magnets, magnets 5002, 5004 are oriented so that opposite poles of magnets 5002, 5004 face each other, thus triggering attraction forces. Magnets 5002 are disposed around the periphery of ball 331, whereas magnets 5004 are positioned around an inner surface of cup 331. (See FIG. 51). When articulating section 230 is longitudinal aligned with elongate outer tube 210, magnets 5002 are radially aligned with magnets 5004. The position and orientation of magnets 5002 relative to magnets 5004 trigger attraction forces between them. The attraction forces between magnets 5002, 5004 maintain cup 332 aligned with ball 331. As discussed above, when ball 331 is aligned with cup 332, articulating section 230 is longitudinal aligned with elongate outer tube 210. (See FIG. 2). If cup 332 is moved relative to ball 331 to articulate articulating section 230, the attraction forces of magnets 5002, 5002 draws ball 331 back into alignment with cup 332, as seen in FIG. 2. As seen in FIG. 51, in some embodiments, ball 331 includes detents 5008 attached to each magnets 5002. In turn, cup 332 includes concavities 5006 adapted to securely receive detents 5008. The engagement between detents 5008 and concavities 5006 help secure ball 331 in the neutral position.

Figure 53:
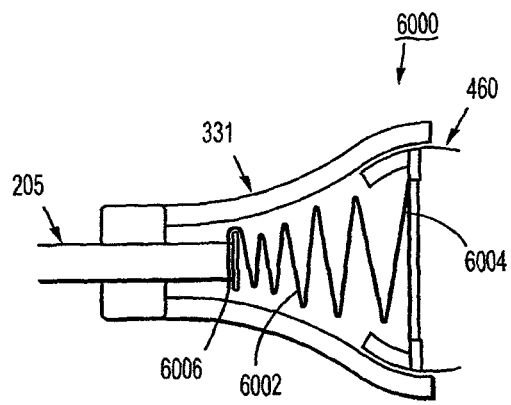
FIG. 53 is side, cutaway view of another embodiment of a straightening mechanism with a helix spring for incorporation in any of the embodiments of the surgical device discussed above.

With reference to FIG. 53, any of the embodiments of surgical device 100 may include a straightening mechanism 6000 for returning articulating section 230 (FIG. 2) into longitudinal alignment with elongate outer tube 210 (FIG. 2) after articulation. Straightening mechanism 6000 includes a conical helical spring 6002 positioned within ball 331. Conical helical spring 6002 has a proximal end 6004 attached to cable holding section 460 and a distal end 6006 attached to actuation cable 205. When handle assembly 300 is articulated relative to elongate outer tube 210 (FIG. 3), one side of conical helical spring 6002 is in tension, while the other side of conical helical spring 6002 is in compression, creating a moment that urges handle assembly 300 back to its neutral position (see FIG. 2). As discussed above, when handle assembly 300 is in its neutral position, articulating section 230 is longitudinally aligned with elongate outer tube 210. It is envisioned that conical helical spring 6002 may be pre-tensioned to increase the moment.

Figure 54:
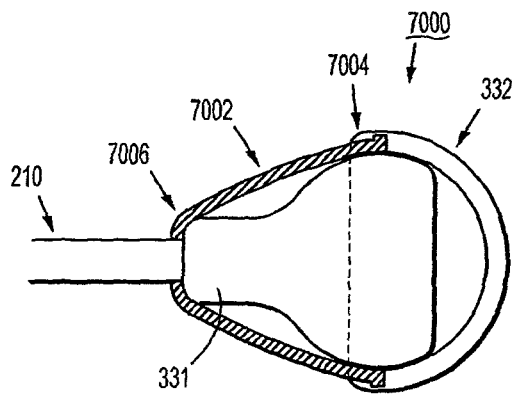
FIG. 54 is a side cross-sectional view of an embodiment of a straightening mechanism including an elastomeric boot for incorporation in any of the embodiments of the surgical device discussed above.

With reference to FIG. 54, any of the embodiments of surgical device 100 may include a straightening mechanism 7000 for returning articulating section 230 (FIG. 2) into longitudinal alignment with elongate outer tube 210 (FIG. 2) after articulation. Straightening mechanism 7000 includes a flexible boot 7002 covering ball 331. It is contemplated that flexible boot 7002 may be made of an elastomeric material or any other suitable material. Flexible boot 7002 has a proximal end portion 7004 attached to cup 332 and a distal end portion 7006 attached to a portion of elongate outer tube 210 located adjacent ball 331. In operation, when cup 332 is moved relative to ball 331, one side of flexible boot 7002 stretches and is in tension, creating a moment that urges ball 331 back to its neutral position (see FIG. 2).

Figure 55:
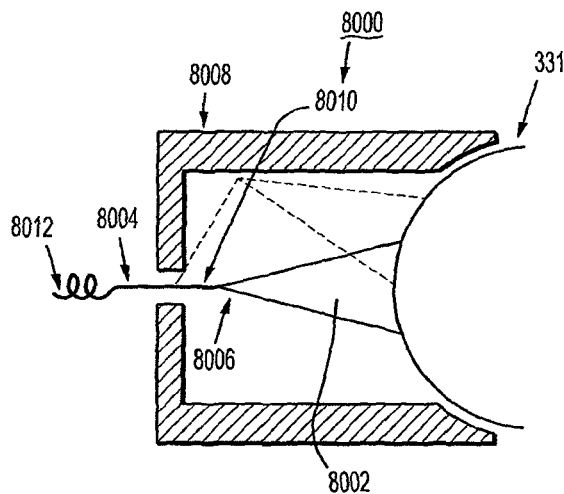
FIG. 55 is a side cross-sectional view of an embodiment of a straightening mechanism having an elastomeric member for incorporation in any of the embodiments of the surgical device discussed above.

With reference to FIG. 55, any of the embodiments of surgical device 100 may include a straightening mechanism 8000 for returning articulating section 230 (FIG. 2) into longitudinal alignment with elongate outer tube 210 (FIG. 2) after articulation. Straightening mechanism 8000 includes a protruding member 8002 extending proximally from ball 331 and an elastic member 8004 attached to a proximal end 8006 of protruding member 8002. Elastic member 8004 has a distal end 8010 attached to protruding member 8002 and a proximal end 8012 attached to articulation cable plate 311 (FIG. 21). A housing 8008 encloses protruding member 8002 and at least a portion of elastic member 8004. In operation, when ball 331 is moved relative to cup 332 (FIG. 21), elastic member 8004 stretches (as shown in phantom). As a result, tension builds up on elastic member 8004. This tension creates a restoring moment that biases ball 331 toward the neutral position. (See FIG. 2).

Figure 56:
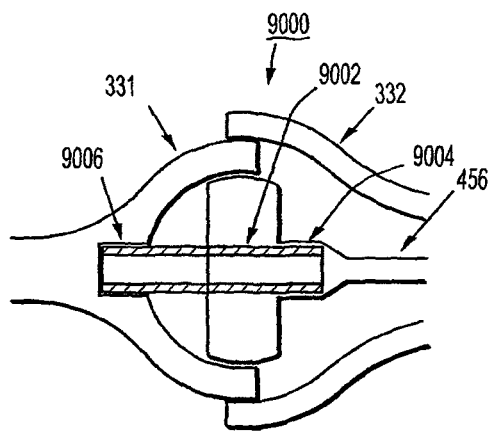
FIG. 56 is a side cross-sectional view of an embodiment of a straightening mechanism having a superelastic member for incorporation in any of the embodiments of the surgical device discussed above.

With reference to FIG. 56, any of the embodiments of surgical device 100 may include a straightening mechanism 9000 for returning articulating section 230 (FIG. 2) into longitudinal alignment with elongate outer tube 210 (FIG. 2) after articulation. Straightening mechanism 9000 includes a tube or rod 9002 made of a material exhibiting superelastic properties. It is envisioned that tube 9002 is substantially resilient. In some embodiments, tube 9002 is wholly or partly made of a shape memory material such as Nitinol. Tube 9002 has a proximal end 9004 and a distal end 9006. Proximal end 9004 of rod 9002 is attached to proximal torque tube 456, while distal end 9006 of rod 9002 is fixed to ball 331. When ball 331 is articulated with respect to cup 332, tube 9002 articulates and creates a moment that biases ball 331 towards its neutral position (see FIG. 2). In some embodiments, tube 9002 corresponds to proximal torque coil 468 shown in FIG. 24.

Figure 57:
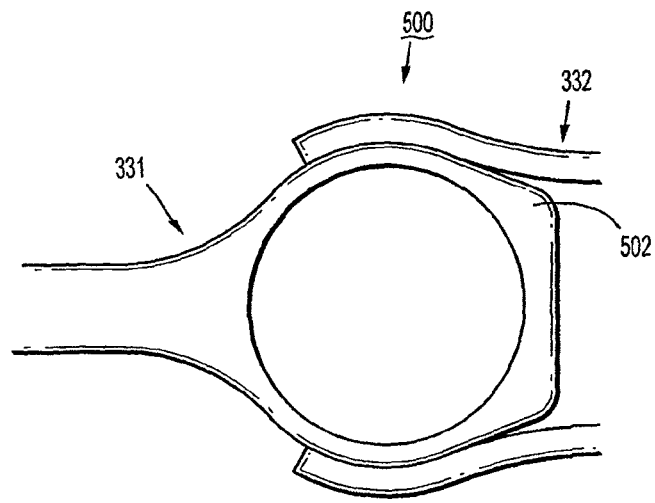
FIG. 57 is side, cut-away view of an embodiment of a straightening mechanism with an elongate ball for incorporation in any of the embodiments of the surgical device discussed above.

With reference to FIG. 57, any of the embodiments of surgical device 100 may include a straightening mechanism 500 for returning articulating section 230 (FIG. 2) into longitudinal alignment with elongate outer tube 210 (FIG. 2) after articulation. In straightening mechanism 500, ball 331 includes an elongate portion 502 extending proximally therefrom. When ball 331 is moved relative to cup 332, elongate portion 502 spreads cup 332. As a consequence, cup 332 exerts a force on elongate portion 502 and urges ball 331 to its neutral position (see FIG. 2).

Figure 58:
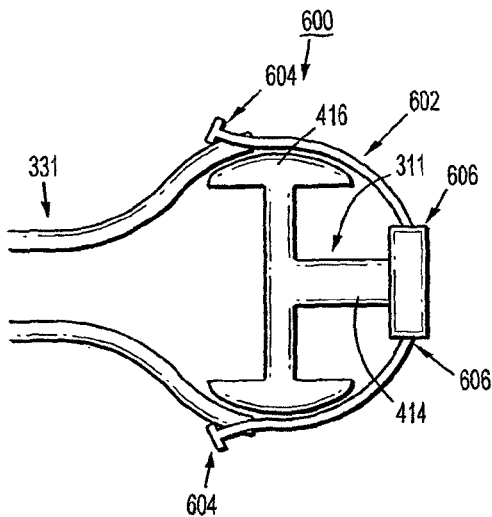
FIG. 58 is side, cut-away view of an embodiment of a straightening mechanism with elastic bands for incorporation in any of the embodiments of the surgical devices discussed above.

With reference to FIG. 58, any of the embodiments of surgical device 100 may include a straightening mechanism 600 for returning articulating section 230 (FIG. 2) into longitudinal alignment with elongate outer tube 210 (FIG. 2) after articulation. Straightening mechanism 600 includes a plurality of elastic bands 602 configured to bias ball 331 to a neutral position (see FIG. 2). Each elastic band 602 has a proximal end 606 and a distal end 604. Proximal ends 606 of each elastic band 602 are attached to elongate portion 414 of articulation cable plate 311. Distal ends 604 of each elastic band are attached to a distal portion of ball 331. During operation, when ball 331 is moved relative to cup 332 (FIG. 21), at least one elastic bands 602 stretches and biases ball 331 toward its neutral position (see FIG. 2). It some embodiments, straightening mechanism 600 includes three elastic bands 602, but it is envisioned that straightening mechanism 600 may include more or fewer elastic bands 602.

Figure 59:
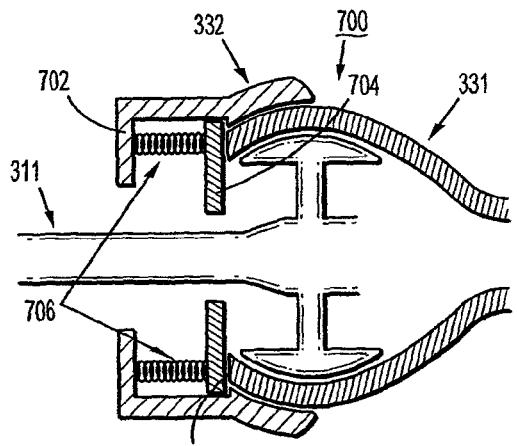
FIG. 59 is a side cross-sectional view of an embodiment of straightening mechanism with proximally-located springs for incorporation in any of the embodiments of the surgical device discussed above.

With reference to FIG. 59, any of the embodiments of surgical device 100 may include a straightening mechanism 700 for returning articulating section 230 (FIG. 2) into longitudinal alignment with elongate outer tube 210 (FIG. 2) after articulation. Straightening mechanism 700 includes an annular wall 702 extending radially and inwardly from an inner surface of cup 332 and a ring 704 positioned adjacent a proximal portion 708 of ball 331. Moreover, straightening mechanism 700 includes a plurality of springs 706 located between annular wall 702 and ring 704. Springs 706 are configured to bias ball 331 to its neutral position (see FIG. 2) upon movement of ball 331 with respect to cup 332. In operation, when ball 331 is moved relative to cup 332, some springs 706 compress, while other springs 706 stretch. The combined elongation and compression of springs 706 urges ball 331 back to its neutral position (see FIG. 2).

Figure 60:
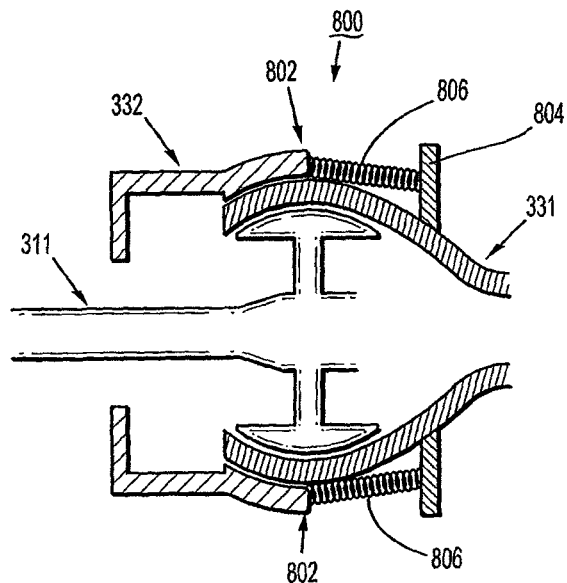
FIG. 60 is a side cross-sectional view of an embodiment of straightening mechanism with distally-located springs for incorporation in any of the embodiments of the surgical device discussed above.

With reference to FIG. 60, any of the embodiments of surgical device 100 may include a straightening mechanism 800 for returning articulating section 230 (FIG. 2) into longitudinal alignment with elongate outer tube 210 (FIG. 2) after articulation. Straightening mechanism 800 includes a ring 804 positioned distally of cup 332 and around a portion of ball 331. Moreover, straightening mechanism 800 includes a plurality of springs 806 located between ring 804 and a distal end 802 of cup 332. Springs 806 are configured to bias ball 331 to its neutral position (see FIG. 2) upon movement of ball 331 with respect to cup 332. In operation, when ball 331 is moved relative to cup 332, some springs 806 compress, while other springs 806 stretch. The combined elongation and compression of springs 806 urges ball 331 back to its neutral position (see FIG. 2).

Figure 61:
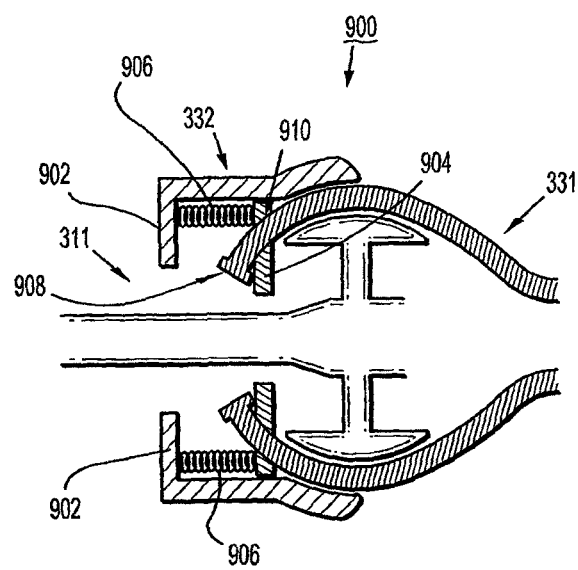
FIG. 61 is a side cross-sectional view of an embodiment of a straightening mechanism with a ring and springs for incorporation in any of the embodiments of the surgical device discussed above.

With reference to FIG. 61, any of the embodiments of surgical device 100 may include a straightening mechanism 900 for returning articulating section 230 (FIG. 2) into longitudinal alignment with elongate outer tube 210 (FIG. 2) after articulation. Straightening mechanism 900 includes an annular wall 902 extending radially and inwardly from an inner surface of cup 332 and a ring 904 positioned adjacent a proximal portion 908 of ball 331. Ring 904 defines an annular slot 910 configured to slidably receive proximal portion 908 of ball 331. Moreover, straightening mechanism 900 includes a plurality of springs 906 located between annular wall 902 and ring 904. Springs 906 are configured to bias ball 331 to its neutral position (see FIG. 2) upon movement of ball 331 with respect to cup 332. In operation, when ball 331 is moved relative to cup 332, springs 906 elongate, causing tension in springs 906. As a result of the tension, springs 906 urges ball 331 back to its neutral position (see FIG. 2).

As can be appreciated, some, or all of articulation cables 240$_{A-D}$ are tensioned depending on the position of handle assembly 300 with respect to elongate outer tube 210. Prolonged tensioning of articulation cables 240$_{A-D}$ may cause undesired stretching of articulation cables 240$_{A-D}$, which may ultimately result in imprecise or inconsistent articulation of articulating section 230, and which may reduce the overall lifetime of the surgical device 100. Additionally, maintaining surgical device 100 in one position for a prolonged period of time, e.g., the time between packaging after manufacture and use, may cause articulation cables 240$_{A-D}$, if under a prolonged tension force, to stretch. This may also affect the articulation of surgical instrument 100.

Accordingly, as shown in FIGS. 65A-68B and as will be described hereinbelow, various embodiments are provided in which articulation lock trigger 304 is configured to initially be disposed in a "shipping" position wherein cables 240$_{A-D}$ are substantially un-tensioned. Upon the initial actuation of articulation lock trigger 304, articulation mechanism 330 is permanently transitioned to a "use" position wherein cables 240$_{A-D}$ are placed into tension in order to articulate articulation section 230, as described above. As can be appreciated, the "shipping" position allows surgical instrument 100 to be maintained, or stored for extended periods of time without the risk of prolonged tensioning of articulation cables 240$_{A-D}$.

With reference now to the embodiment of FIGS. 65A-65B, an articulation lock trigger 1304 of an articulation mechanism 1330 is shown. As seen in FIG. 65A, articulation lock trigger 1304 of articulation mechanism 1330 is shown disposed in the shipping position and correspondingly, articulation cable plate 1311 is disposed in a distal-most position due to the coupling of articulation lock trigger 1304 and articulation cable plate 1311 via a linkage 1310. With articulation cable plate 1311 in this distal-most position, articulation cables 240$_{A-D}$ (FIG. 15) are substantially un-tensioned. It is contemplated that articulation cable plate 1311 may be biased toward this distal-most position wherein, absent any opposing forces, i.e., where articulation lock trigger 1304 is not being depressed, the articulation mechanism 1330 is retained in the shipping position. It is envisioned that surgical device 100 be initially disposed in this shipping position.

With continued reference to FIG. 65A, articulation cable plate 1311 supports a spring member in the form of a flat spring 1350. Flat spring 1350 includes a pair of flexible legs 1352, 1354 interconnected by a backspan, or base 1356. Base 1356 is fixedly connected to articulation cable plate 1311 at a proximal end 1313 of articulation plate 1313 to retain flat spring 1350 thereon. Legs 1352, 1354 extend proximally from base 1356 and each leg 1352, 1354 includes a laterally protruding flange 1353, 1355, respectively, disposed at a proximal end thereof and defining camming surfaces.

Housing 1340 includes a bumper 1342 positioned proximally of and substantially aligned with articulation plate 1311. Bumper 1342 defines a shelf 1344 having a pair of notched members 1346 positioned thereon, although only one notched member 1346 is shown in the cut-away view of FIG. 65A. Notched members 1346 each include a ramped distal portion 1347 and a recessed proximal portion 1349 configured to retain flanges 1353, 1355 of respective legs 1352, 1354 of spring 1350, as will be described below.

To move articulation mechanism 1330 from the shipping position (FIG. 65A) to the use position (FIG. 65B), articulation lock trigger 1304 is depressed, or pulled proximally. As articulation lock trigger 1304 is pulled proximally, articulation lock trigger 1304 pivots about pivot 1335, translating linkage 1310 proximally and thereby translating articulation cable plate 1311 proximally. As articulation cable plate 1311 is translated proximally, articulation cables 240$_{A-D}$ (FIG. 15) are increasingly tensioned. At the same time, the proximal translation of articulation cable plate 1311 translates flat spring 1350 proximally. More specifically, flanges 1353, 1355 of respective legs 1352, 1354 of flat spring 1350 are translated proximally toward notched members 1346 disposed on bumper 1342.

Upon further proximal translation of articulation lock trigger 1304, and, thus, articulation cable plate 1311, flanges 1353, 1355 of respective legs 1352, 1354 of flat spring 1350 ramp up and over distal portions 1347 of notched members 1346 until flanges 1353, 1355 of legs 1352, 1354 drop into engagement with recessed proximal portions 1349 of notched members 1346 (FIG. 65B). Once flanges 1353, 1355 drop into engagement with recessed proximal portions 1349 of notched members 1346, articulation lock trigger 1304 may be released, allowing articulation lock trigger 1304 and articulation cable plate 1311 to begin to return distally under the bias of articulating cables 240 (FIG. 15), due to the tension of articulation cables 240. However, the engagement of flanges 1353, 1355 within recessed proximal portions 1349 of notched members 1346 inhibits distal translation of articulation cable plate 1311 back to the un-tensioned, or shipping position. Instead, articulation cables 240$_{A-D}$ (FIG. 15) remain in a tensioned state. With articulation cables 240$_{A-D}$ (FIG. 15) in this tensioned state due to the engagement of flanges 1353, 1355 within recessed proximal portions 1349, surgical device 100 is in the use position (FIG. 65B). It is envisioned that flat spring 1350 and notched members 1346 be configured such that articulation mechanism 1330 is permanently transitioned from the shipping position to the use position upon the initial depression of articulation lock trigger 1304. In other words, it is envisioned that, once moved to the use position, articulation mechanism 1330 is prevented from returning to the shipping position.

With continued reference to FIGS. 65A-65B, recessed proximal portions 1349 of notched members 1346 have a greater length than flanges 1353, 1355 of flat spring 1350 such that flanges 1353, 1355 may still translate longitudinally, e.g., proximally and distally, when in the use position, e.g., when flanges 1353, 1355 are engaged within recessed proximal portions 1349 of notched members 1346. As can be appreciated, the dimensions of recessed proximal portions 1349 of notched members 1346 may be configured according to the desired range of motion of articulation lock trigger 1304. Accordingly, a greater lengthed recessed portion 1349 would allow for greater translation of flanges 1353, 1355 therein, thus allowing a larger range of motion of articulation lock trigger 1304 and articulation cable plate 1311. It is envisioned that recessed proximal portions 1349 be sufficiently dimensioned to permit the locking and unlocking of articulation cables 240$_{A-D}$ (FIG. 15) in position, as will be described in greater detail hereinbelow. On the other hand, it is envisioned that recessed proximal portions 1349 be sufficiently dimensioned to prevent articulation cables 240$_{A-D}$ (FIG. 15) from becoming un-tensioned and/or over-tensioned.

Referring now to FIGS. 66A-66B, another embodiment of an articulation mechanism 2330 is shown. Similar to articulation mechanism 1330, articulation lock trigger 2304 and articulation cable plate 2311 of articulation mechanism 2330 are initially disposed in the shipping, or distal-most position. Articulation lock trigger 2304 and articulation cable plate 2311 are biased toward this distal-most position by articulation cables 240$_{A-D}$ (FIG. 15), with articulation cables 240 (FIG. 15) being biased toward a substantially un-tensioned position. As mentioned above, this un-tensioned shipping position allows surgical device 100 to be stored or maintained for a prolonged period of time prior to use, without the risk of prolonged strain on articulation cables 240$_{A-D}$ (FIG. 15).

With continued reference to FIGS. 66A-66B, articulation cable plate 2311 includes a recessed portion 2313 defined in a surface thereof toward a proximal end thereof. A spring member 2350 is fixedly engaged at one end thereof to housing 2340 via retainer 2342. Initially, when articulation cable plate 2311 is disposed in the shipping position, a free end 2352 of spring member 2350 is positioned proximal of articulation cable plate 2311.

To move articulation mechanism 2330 from the shipping position to the use position, articulation lock trigger 2304 is pulled proximally to pivot about pivot 2335. As articulation lock trigger 2304 is pulled proximally, linkage 2310 is pivoted such that articulation cable plate 2311 is translated proximally against the bias of articulation cables 240$_{A-D}$ (FIG. 15), thereby increasing tension on articulation cables 240$_{A-D}$ (FIG. 15). Translation of articulation cable plate 2311 proximally moves articulation cable plate 2311 toward free end 2352 of spring member 2350. Upon further pulling of articulation lock trigger 2304, free end 2352 of spring member 2350 cams along a surface of articulation cable plate 2311 as articulation cable plate 2311 is translated further proximally. Eventually, free end 2352 of spring 2350 cams along the surface of articulation cable plate 2311 until free end 2352 of spring 2350 drops into engagement with recessed portion 2313 of articulation cable plate 2311 due to the bias of spring 2350, as shown in FIGS. 66A-B. The engagement of spring 2350 within recessed portion 2313 of articulation cable plate 2311 corresponds to the use position of articulation mechanism 2330. Once spring 2350 is engaged within recessed portion 2313, spring 2350 is maintained therein due to the bias of spring 2350, such that articulation mechanism 2330 is retained in the use position.

Similar to articulation mechanism 1330 described above, the dimensions of recessed portion 2313 define the range of motion of articulation lock trigger 2304 and thus define the range of tension imparted to articulation cables 240$_{A-D}$ (FIG. 15). Thus, as articulation lock trigger 2304 is pulled and released, spring 2350 is translated relative to recessed portion 2313 of articulation cable plate 2311 along a length thereof to move the articulation mechanism 2330 between a locked position and an unlocked position. Additionally, recessed portion 2313 is preferably dimensioned to prevent articulation cables 240$_{A-D}$ (FIG. 15) from becoming un-tensioned and/or over-tensioned.

Referring now to FIGS. 67A-67B, still another embodiment of an articulation mechanism is shown as 3330. Articulation mechanism 3330 is capable of transitioning from an initial shipping position to a use position is shown. Articulation cable plate 3311 includes an elongated flat spring 3350 disposed thereon and mechanically engaged therewith at a proximal end 3352 of elongated flat spring 3350. Elongated flat spring 3350 extends distally along articulation cable plate 3311 and includes a notch 3356 disposed at a distal end 3354 thereof. Notch 3356 includes a ramped proximal end and a substantially vertical distal end to define triangular-shaped notch 3356.

Initially, when in the shipping position, as shown in FIG. 67A, distal end 3354 of elongated flat spring 3350, including notch 3356, are disposed distal of cup 3332. Correspondingly, articulation lock trigger 3304 and articulation cable plate 3311 are disposed in the shipping, or distal-most position wherein cables 240 are substantially un-tensioned.

To move articulation mechanism 3330 from the shipping position (FIG. 67A) to the use position, articulation lock trigger 3304 is pulled proximally and pivoted about pivot 3335, thereby pivoting linkage 3310 and translating articulation cable plate 3311 and elongated flat spring 3350 proximally. As articulation cable plate 3311 and elongated flat spring 3350 are translated proximally, notch 3356 approaches cup 3332. Upon further proximal translation, notch 3356 contacts cup 3332 causing elongated flat spring 3350 to compress. With a sufficient pulling force on articulation lock trigger 3304, flat spring 3350 compresses to allow notch 3356 to pass under cup 3332, as cup 3332 is ramped over ramped distal end 3354 of notch 3356, as shown in FIG. 67B. In other words, notch 3356 is flexed to pass through the opening 3359 defined between cup 3332 and articulation cable plate 3311 to a position proximal of cup 3332.

Once notch 3356 has been translated to a position proximal of cup 3332, articulation mechanism 3330 is in the use position wherein articulation cables 240$_{A-D}$ are tensioned. Articulation mechanism 3330 is prevented from returning to the shipping position due to the vertical distal end of notch 3356, which inhibits the passage of notch 3356 back through the opening 3359 defined between cup 3332 and articulation cable plate 3311. In the use position, as will be described in greater detail below, articulation lock trigger 3304 may be depressed to fix the position of articulating section 230 (FIG. 27).

Figure 68A:
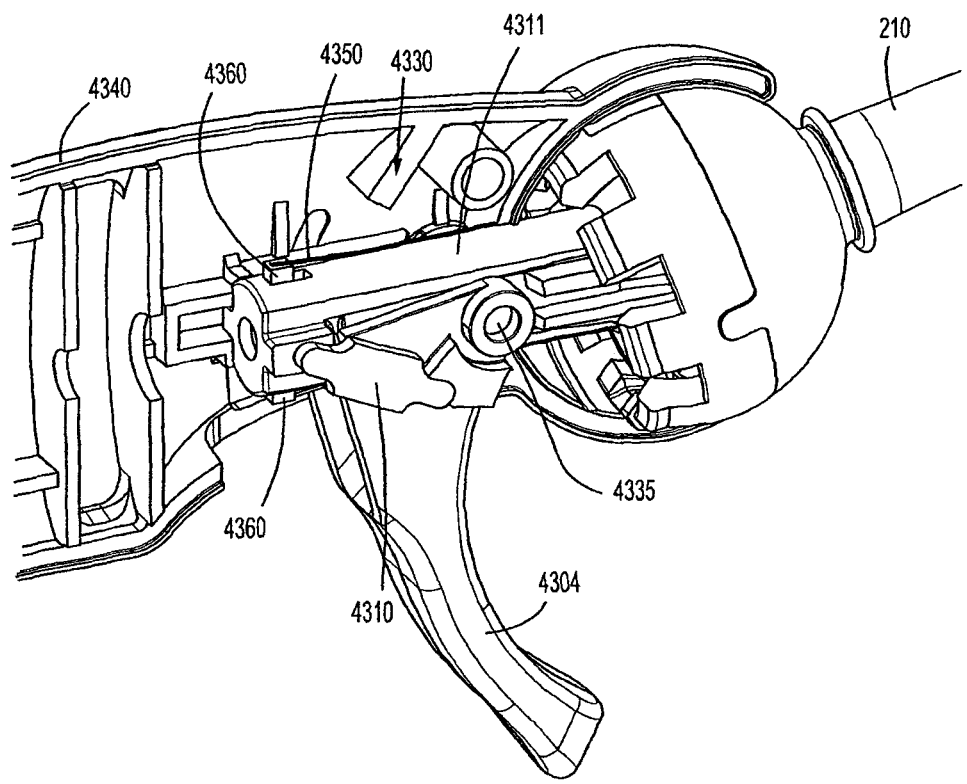
FIG. 68A is a perspective cut-away view of still another embodiment of an articulation mechanism shown in the shipping position.
Figure 68B:
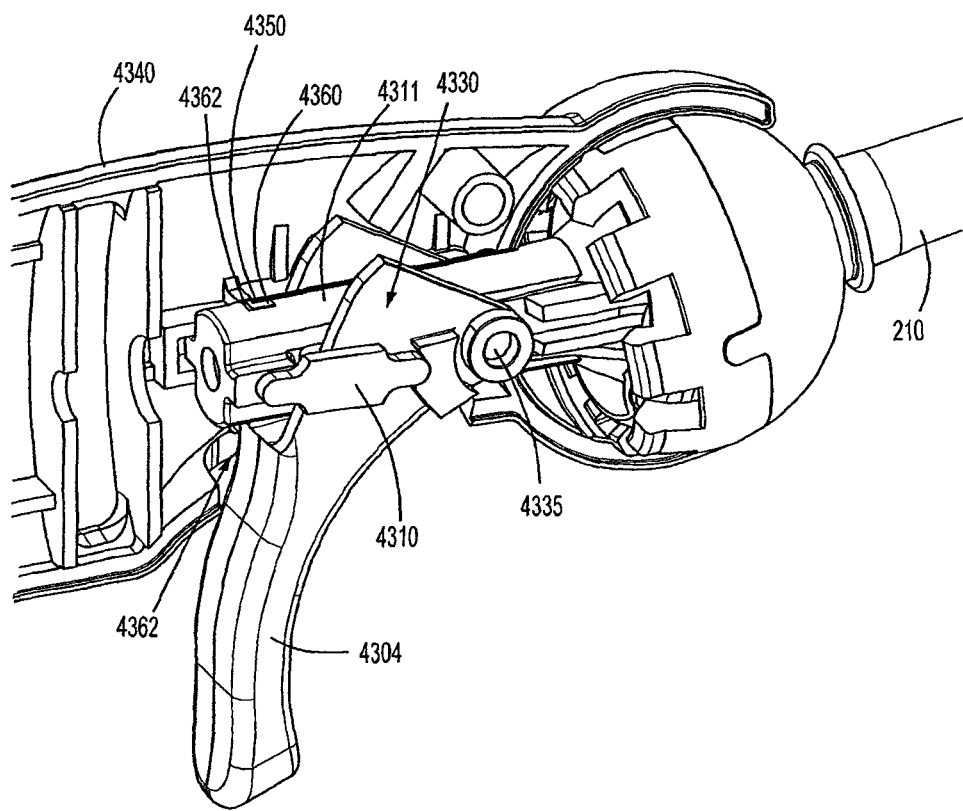
FIG. 68B is a perspective cut-away view of the articulation mechanism of FIG. 68A shown in the use position.

With reference now to FIGS. 68A-68B, another embodiment of an articulation mechanism is shown as 4330. Articulation mechanism 4330 is capable of transitioning from an initial shipping position to a use position is shown. The shipping position in shown in FIG. 68A, wherein articulation lock trigger 4304 and articulation cable plate 4311 are disposed in a distal-most position, such that articulation cables 240$_{A-D}$ (FIG. 15) are substantially un-tensioned. A pair of wire springs 4350 extending along upper and lower surfaces of articulation cable plate 4311 are connected at a distal end to housing 4340 and at a proximal end to stop members 4360. In the shipping position, stop members 4360 displace wire springs 4350 outwardly from the upper and lower surfaces of articulation cable plate 4311 at a proximal end thereof, as best shown in FIG. 68A. As can be appreciated, the outward displacement of wire springs 4350 tensions wire springs 4350, thereby biasing articulation cable plate 4311 distally. This tensioned configuration of wire springs 4350, in the shipping configuration, maintains articulation cable plate 4311 in a distal-most position, such that articulation cables 240$_{A-D}$ (FIG. 15) are substantially un-tensioned.

To move articulation mechanism 4330 from the shipping position (FIG. 68A) to the use position (FIG. 68B), articulation lock trigger 4304 is pulled proximally. As articulation lock trigger 4304 is pulled proximally from the initial, shipping position, articulation lock trigger 4304 is pivoted about pivot 4335 and linkage 4310 is pivoted to translate articulation cable plate 4311 proximally. Upon proximal translation of articulation cable plate 4311, stop members 4360 fall into recesses 4362 defined within the upper and lower surfaces of articulation cable plate 4311 under the bias of wire springs 4350. With stop members 4360 disposed in recesses 4360 of articulation cable plate 4311 (FIG. 68B), wire springs 4350 are no longer displaced outwardly from the surface of articulation cable plate 4311 and, thus, the tension on wire springs 4350 is eliminated. This position corresponds to the use position, wherein articulation cables 240 (FIG. 15) are tensioned. Articulation mechanism 4330 is prevented from returning to the shipping configuration due to the positioning of wire springs 4350, which resist compression. Further, articulation cables 240 (FIG. 15) remain in a tensioned state because the force exerted by wire springs 4350 against compression prevents articulation cables 240 (FIG. 15) from returning to the un-tensioned position (the shipping position).

Figure 69:
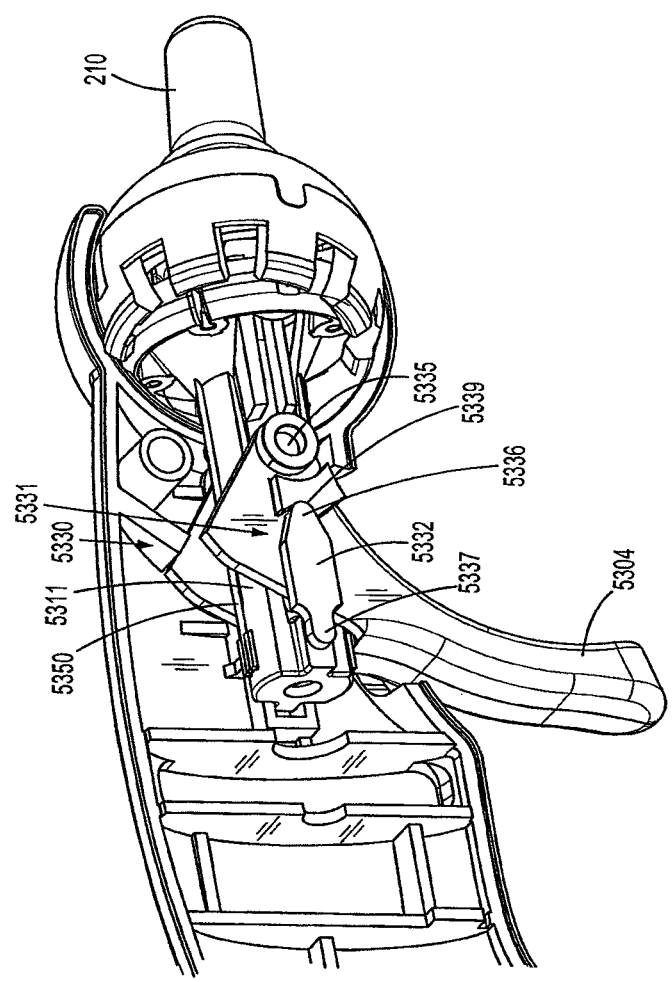
FIG. 69 is a perspective cut-away view of a two-bar linkage coupling an articulation lock trigger and an articulation cable plate in accordance with the present disclosure.

In another embodiment, as shown in FIG. 69, articulation lock trigger 5304 is pivotably engaged with articulation cable plate 5311 via a two-bar linkage 5332. More specifically, articulation lock trigger 5304 is coupled to articulation cable plate 5311 on one side by a first linkage bar 5332 and on the other side by a second linkage bar (not shown). First linkage bar 5332 is pivotably engaged at one end to articulation lock trigger 5304 via pivot 5336 and pivotably engaged at the other end to articulation cable plate 5311 via pivot 5337. The second linkage bar (not shown) similarly engages articulation lock trigger 5304 and articulation cable plate 5311 on the opposite sides thereof. Pivot 5336 is disposed within a notch 5339 defined within articulation lock trigger 5304 such that, as articulation lock trigger 5304 is depressed, notch 5339 urges linkage bars 5332 to pivot about pivot 5336.

Figure 70A:
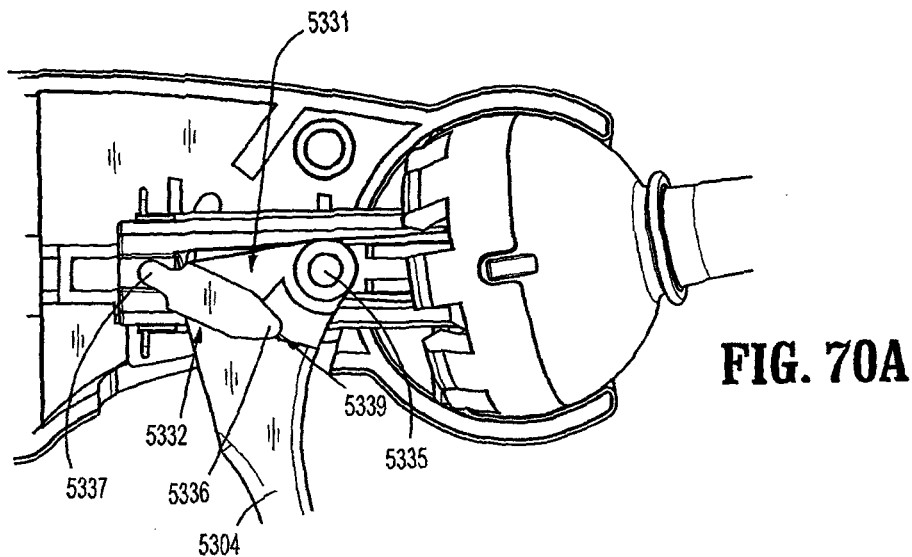
FIG. 70A is a perspective cut-away view of the articulation lock trigger of FIG. 69 shown in the shipping position.

Articulation lock trigger 5304 may initially be disposed in a shipping position, as shown in FIG. 70A. Accordingly, any one of the embodiments discussed above, or any other suitable mechanism, may be employed to initially maintain articulation mechanism 5330 in a shipping position, wherein articulation cables $240_{A-D}$ (FIG. 15) are substantially un-tensioned, and to allow the permanent transition of articulation mechanism 5330 to the use position upon the initial depression of articulation lock trigger 5304.

Figure 70B:
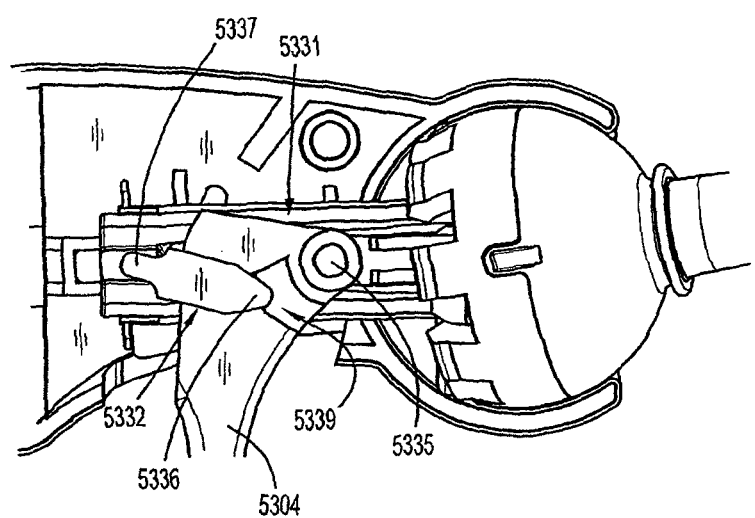
FIG. 70B is a perspective cut-away view of the articulation lock trigger of FIG. 69 shown in the unlocked position.
Figure 70C:
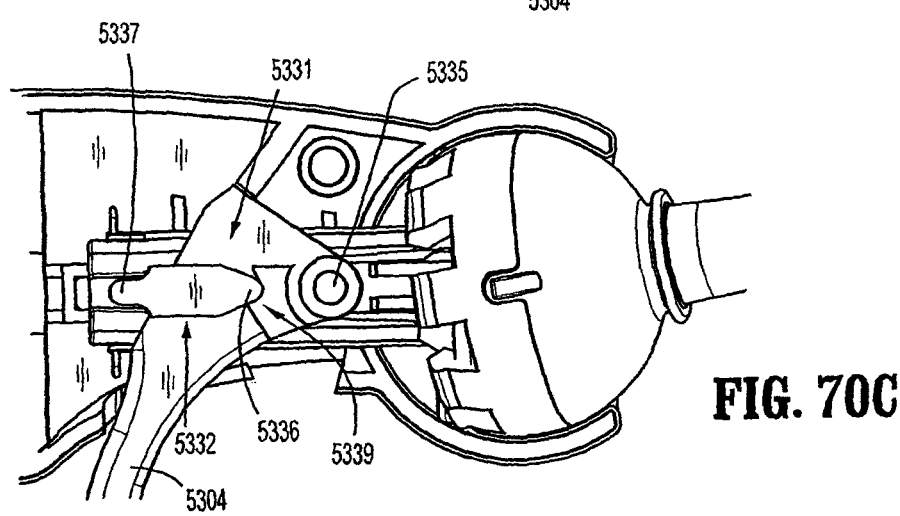
FIG. 70C is a perspective cut-away view of the articulation lock trigger of FIG. 69 shown in the locked position.

With articulation lock trigger 5304 in the use position, an over-center clamp mechanism 5331 is configured for movement between an unlocked position (FIG. 70B), wherein pivot 5336 is offset below pivots 5335 and 5337, through a center position, wherein pivots 5335, 5336, and 5337 are substantially aligned with one another, to an over-center, or locked position (FIG. 70C), wherein pivot 5336 is offset above pivots 5335 and 5337. As shown in FIG. 70C, in the over-center, or locked position, pivot 5336 may be offset from pivots 5335 and 5337 by about two degrees (2°) to about three degrees (3°).

Once articulation lock trigger 5304 is permanently moved to the use position, e.g., by the initial depressing of articulation lock trigger 5304, the position of articulation section 230 (FIG. 27) may be fixed with respect to elongate outer tube 210. When in the use position, articulation lock trigger 5304 is biased toward the unlocked position (FIG. 70B) via spring 5350 (FIGS. 66A-66B). Thus, articulation lock trigger 5304 must be depressed with sufficient force to overcome the bias of spring 5350 to move pivot 5336 through the center position to the over-center position (FIG. 70C) in order to lock the position of articulating section 230 (FIG. 27).

In operation, to fix the position of articulating section 230 (FIG. 27), articulation lock trigger 5304 is depressed proximally against the bias of spring 5350. As articulation lock trigger 5304 is depressed from the unlocked position shown in FIG. 70B, articulation lock trigger 5304 is pivoted about pivot 5335, and pivot 5336 is urged toward the center position due to the engagement of pivot 5336 within notch 5339. As pivot 5336 is urged toward the center position, linkage bar 5332 is urged proximally, thereby urging articulation cable plate 5311 proximally due to the pivotable coupling of linkage bar 5332 and articulation cable plate 5311. Consequently, articulation cables 240 (FIG. 15) are tightened, thereby compressing articulation links 232, 234 together (FIG. 27) and fixing the position of articulating section 230 (FIG. 27) relative to elongate outer tube 210. Upon further proximal pulling of articulation lock trigger 5304, pivot 5336 is moved to the over-center position, offset above pivots 5335 and 5337. In this position, as shown in FIG. 70C, over-center clamp mechanism 5331 is "locked" in position and, thus, the fixed position of the articulating section 230 (FIG. 27) is maintained. Accordingly, the articulation lock trigger 5304 may be released, while the articulating section 230 (FIG. 27) remains fixed in position due to the over-center configuration of over-center clamp mechanism 5331, as shown in FIG. 70C. To unlock the over-center clamp mechanism 5331, the articulation lock trigger 5304 is once again depressed proximally, allowing pivot 5336 to move back past the center position towards the unlocked position (FIG. 70B).

Figure 73:
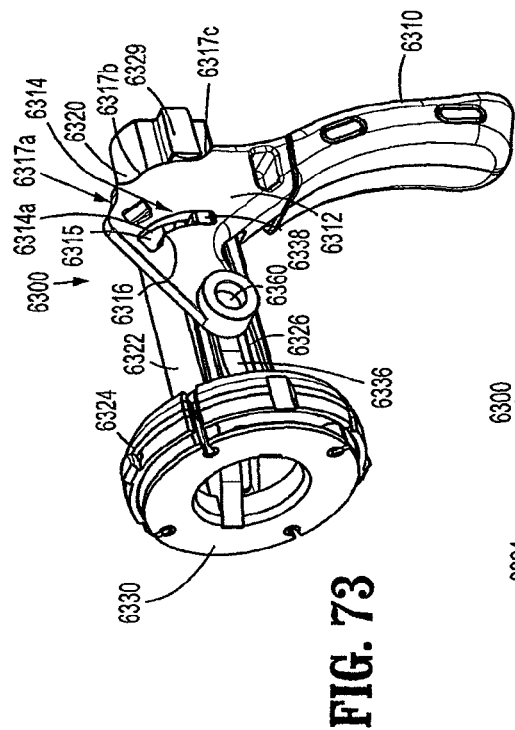
FIG. 73 is an isolated, front, perspective view of the articulation mechanism of FIG. 71A shown in the locked, use position.
Figure 72:
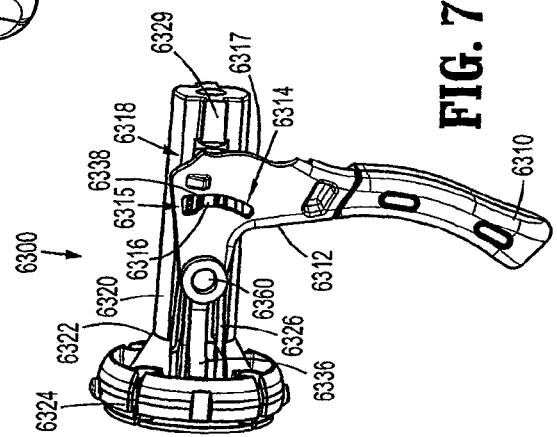
FIG. 72 is an isolated, rear, perspective view of the articulation mechanism of FIG. 71A shown in the unlocked, use position.

With reference now to FIGS. 71A-75, another embodiment of an articulation mechanism is shown as 6300. Articulation mechanism 6300 is configured to transition between a shipping position (FIGS. 71A-71B) and a use position. When in the use position, articulation mechanism 6300 is further configured for transitioning between an unlocked position (FIG. 72), and a locked position (FIG. 73). Articulation mechanism 6300 includes an articulation lock trigger 6310, a shaft 6320 having a lock plate 6324 disposed at a distal end 6332 thereof, a cable plate 6330 configured to secure proximal ends of articulation cables $240_{A-D}$ (FIG. 15) therein, and an articulation sphere (see FIGS. 70A-70C) operably positioned within spherical-shaped cavity 6352 of housing 6350.

Figure 74:
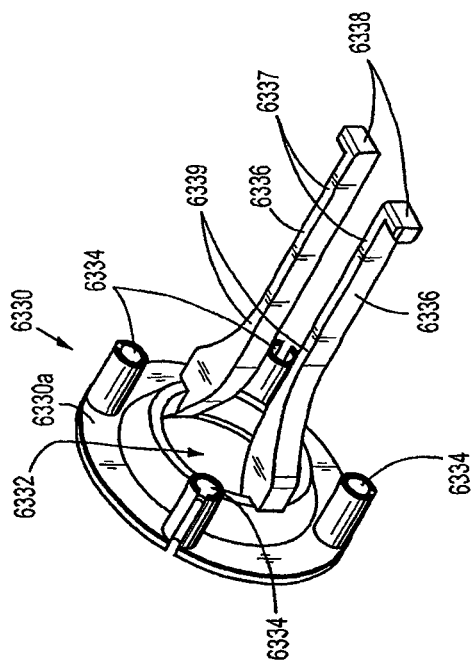
FIG. 74 is an isolated, rear, perspective view of a cable plate of the articulation mechanism of FIG. 71A.

Referring now to FIG. 74, cable plate 6330 defines a circular wall front cross-section 6330a and includes an aperture 6332 centrally defined therethrough. Four (4) ferrules 6334 are positioned annularly about cable plate 6330 toward an outer circumference thereof and extend proximally from cable plate 6330. Each ferrule 6334 is configured to securely retain a proximal end of one of articulation cables $240_{A-D}$ (FIG. 15) therein. As can be appreciated, with the proximal ends of articulation cables 240 (FIG. 15) engaged within ferrules 6334 of cable plate 6330, translating cable plate 6330 proximally tensions articulation cables 240 (FIG. 15) and translating cable plate 6330 distally slackens, or un-tensions articulation cables 240 (FIG. 15).

Cable plate 6330 further includes a pair of arms 6336 extending proximally therefrom. Each arm 6336 includes a tab 6338 disposed at a proximal, or free end 6337 thereof and may define a generally tapered configuration, decreasing in width from a distal, or fixed end 6339 thereof to free end 6337 thereof. When articulation mechanism 6330 is assembled, as shown in FIG. 71A, arms 6336 of cable plate 6330 are inserted proximally through a central aperture (not explicitly shown) defined within lock plate 6324 such that cable plate 6330 is positioned distally of, and substantially mating with respect to lock plate 6324, while arms 6336 extend proximally through longitudinal channels 6327 defined along opposite longitudinal sides 6326 of shaft 6320.

With reference again to FIGS. 71A-75, articulation mechanism 6300 includes an articulation lock trigger 6310 pivotably coupled to shaft 6320. More specifically, articulation lock trigger 6310 includes a pair of upwardly-extending flanges 6312 that are pivotably coupled to shaft 6320 on opposite sides thereof via pivot 6360. Articulation lock trigger 6310 is selectively depressible from a shipping position, wherein shaft 6320 and cable plate 6330 are in a distal-most position, to a use position, wherein arms 6336 of cable plate 6330 are translated proximally to tension articulation cables 240$_{A\text{-}D}$ (FIG. 15). Once in the use position, articulation lock trigger 6310 is selectively depressible between an unlocked position (FIG. 72), wherein articulating section 230 is permitted to articulate relative to longitudinal axis "X" (see FIGS. 3 and 5), and a locked position (FIG. 73), wherein articulation mechanism 6330 fixes the position of articulating section 230 relative to longitudinal axis "X" (see FIGS. 3 and 5).

Articulation lock trigger 6310 further includes a slot 6314 defined within each of flanges 6312. Each slot 6314 is configured to retain one of tabs 6338 of arms 6336 of cable plate 6330 therein. As will be described in greater detail below, slots 6314 are specifically configured and dimensioned such that tabs 6338 of arms 6336 are translated along slots 6314 during depression and/or release of articulation lock trigger 6310. Further, each slot 6314 defines a groove 6315 toward a top end 6314a thereof. As tabs 6338 are moved from grooves 6315 into slots 6314, e.g., as articulation lock trigger 6310 is depressed from the shipping position to the use position, proximal longitudinal movement of arms 6336 and, thus, cable plate 6330 is effected to tension cables 240 (FIG. 15).

Flanges 6312 of articulation lock trigger 6310 also define a specifically configured proximal surface profile. More particularly, proximally-facing surfaces 6317 of flanges 6312 of articulation lock trigger 6310 define a cam surface 6317 having three distinct segments, a shipping position segment 6317a and two use position segments: an unlocked position segment 6317b, and a locked position segment 6317c. As will be described in greater detail below, proximal earning surfaces 6317 of flanges 6312 slide, or cam with respect to side protrusions 6329 disposed on opposite sides 6326 of shaft 6320 during pivoting of articulation lock trigger 6310 with respect to shaft 6320 about pivot 6360. Due to the configuration of proximally-facing surfaces 6317 of flanges 6312, as articulation lock trigger 6310 is depressed or released when in the use position, the earning of proximal surfaces 6317 of flanges 6312 with respect to side protrusions 6329 of shaft 6320 effects longitudinal movement of shaft 6320 to move shaft 6320 between the unlocked position (FIG. 72), wherein articulation section 230 (FIGS. 3 and 5) is permitted to articulate with respect to longitudinal axis "X" (see FIGS. 3 and 5), and the locked position (FIG. 73), wherein shaft 6320 is in the proximal-most position, fixing the position of articulating section 230 (FIG. 15) with respect to longitudinal axis "X" (see FIG. 2).

Figure 71B:
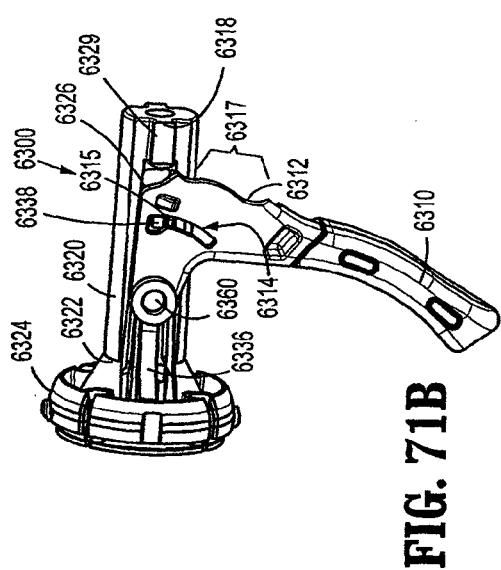
FIG. 71B is an isolated, rear, perspective view of the articulation mechanism of FIG. 71A shown in the shipping position.
Figure 71A:
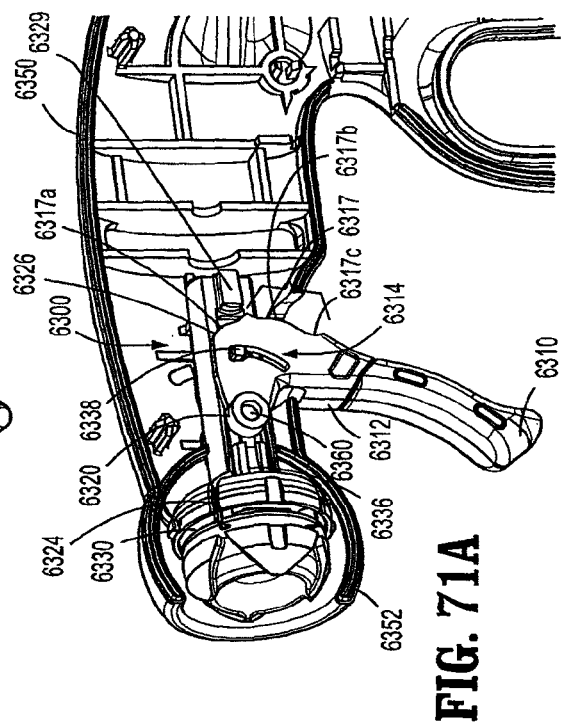
FIG. 71A is a perspective cut-away view of another embodiment of an articulation mechanism, according to the present disclosure, shown in the shipping position.
Figure 75:
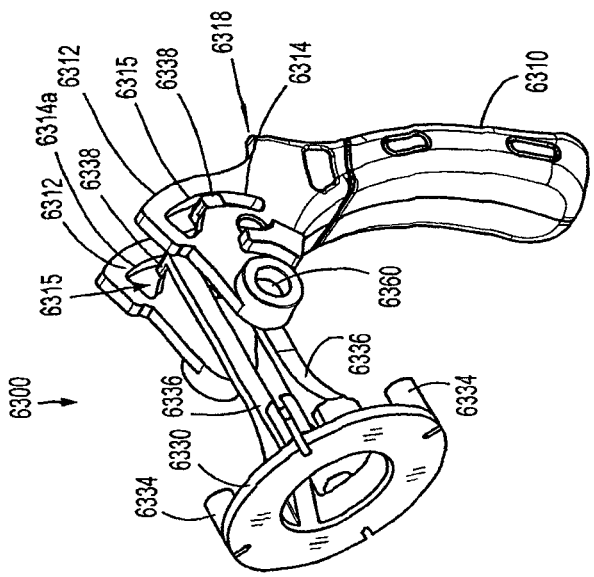
FIG. 75 is an isolated, front, perspective view of the cable plate of the articulation mechanism of FIG. 71A shown coupled to the articulation lock trigger of FIG. 71A.

Articulation mechanism 6300 may initially be disposed in the shipping position, as shown in FIGS. 71A-71B, wherein articulation lock trigger 6310, shaft 6320, and cable plate 6330 are in distal-most positions and wherein articulation cables 240$_{A\text{-}D}$ (FIG. 15) are substantially un-tensioned. More particularly, in the shipping position, tabs 6338 of arms 6336 of cable plate 6330 are each disposed within grooves 6315 of slots 6314 of flanges 6312 of articulation lock trigger 6310. Grooves 6315 protrude distally from slots 6314 such that, when tabs 6338 are disposed within grooves 6315, i.e., when articulation lock trigger 6310 is in the shipping position, tabs 6338 are in the distal-most position and, accordingly, cable plate 6330 and articulation cables 240 (FIG. 15) are in the distal-most, substantially un-tensioned position. Further, a stopper 6316 is positioned within slots 6314 of flanges 6312, as best shown in FIG. 73, to inhibit tabs 6338 of aims 6336 of cable plate 6330 from "slipping" out of grooves 6315 and into slots 6314, i.e., to retain cable plate 6330 and articulation cables 240 (FIG. 15) in the un-tensioned, shipping position.

With continued reference to FIGS. 71A-71B, when articulation mechanism 6300 is in the shipping position, as mentioned above, shaft 6320 is disposed in a distal-most position. More specifically, when articulation lock trigger 6310 is disposed in the shipping position, side protrusions 6329 are disposed within shipping position segments 6317a of proximally-facing surfaces 6317 of flanges 6312 of articulation lock trigger 6310. Shipping position segments 6317a of proximally-facing surfaces 6317 of flanges 6312 define a cut-out area, such that side protrusions 6329 are substantially undisturbed, i.e., such that side protrusions 6329 are not urged proximally, when side protrusions 6329 are disposed within shipping position segments 6317a of proximally-facing surfaces 6317 of flanges 6312. Thus, with side protrusions 6329 of shaft 6312 disposed within shipping position segments 6317a of articulation lock trigger 6310, shaft 6320 is permitted to be biased toward the distal-most, or un-locked position.

As mentioned above, with articulation mechanism 6300 in the shipping position, surgical instrument 100 may be maintained, or stored for extended periods of time without the risk of prolonged tensioning of articulation cables 240$_{A\text{-}D}$, arms 6336 of cable plate 6330, and/or shaft 6320.

To move articulation mechanism 6300 from the shipping position to the use position, articulation lock trigger 6310 is pulled proximally to pivot with respect to shaft 6320 about pivot 6360. As articulation lock trigger 6310 is pulled proximally, or depressed, grooves 6315 and slots 6314 defined within flanges 6312 of articulation lock trigger 6310 are moved with respect to tabs 6338 of arms 6336 of cable plate 6330 such that tabs 6338 are translated proximally over stoppers 6316, disengaging from grooves 6315 and moving into the more proximally-disposed slots 6314 of flanges 6312 of articulation lock trigger 6310. Moving tabs 6338 proximally translates arms 6336, cable plate 6330, and, thus, articulation cables 240 (FIG. 15) proximally, thereby transitioning articulation cables 240 (FIG. 15) from the un-tensioned, shipping position to the tensioned, use position. Once tabs 6338 are moved into slots 6314, stoppers 6316 prevent tabs 6338 from moving back into engagement with grooves 6315, i.e., stoppers 6316 prevent cable plate 6330 and, thus, articulation cables 240 (FIG. 15) from moving distally back to the un-tensioned, shipping position.

As shown in FIGS. 71A-73, slots 6314 are arcuately-shaped according to the pivotal radius of motion of articulation lock trigger 6310 about pivot 6360 such that, once tabs 6338 are moved out of grooves 6315 and into slots 6314, i.e., once articulation lock trigger 6310 is moved from the shipping position to the use position and cables 240 (FIG. 15) are tensioned, cable plate 6330 is maintained in a fixed longitudinal position. In other words, articulation lock trigger 6310 is moved from the shipping position to the use position to move tabs 6338 from grooves 6315 to slots 6314 of flanges 6312 of articulation lock trigger 6310 to tension cables 240 (FIG. 15). However, once articulation lock trigger 6310 is moved to the use position and cables 240 (FIG. 15) are tensioned, the tension on cables 240 (FIG. 15) remains relatively constant, even as articulation lock trigger 6310 is further moved in the use position between the un-locked and locked positions.

Simultaneously, or near-simultaneously with the tensioning of cables 240 (FIG. 15), shaft 6320 is moved from the distal-most, shipping position to the use position when articulation lock trigger 6310 is pulled from the shipping position to the use position. More particularly, upon pivoting of articulation lock trigger 6310 with respect to shaft 6320, side protrusions 6329 disposed on shaft 6320 cam downwardly with respect to proximally-facing surfaces 6317 of flanges 6312 of articulation lock trigger 6310 from shipping position segment 6317a, over shelf 6318 and into the use position sections, e.g., into unlocked position segment 6317b. When side protrusions 6329 are cammed into unlocked position segments 6317b, shaft 6320 is translated proximally to the unlocked, use position. The unlocked, use position of shaft 6320 corresponds to a position wherein shaft 6320 is more-proximally positioned than in the shipping position, but more distally-positioned than in the locked position. With articulation mechanism in the un-locked, use position, handle assembly 6350, as mentioned above, may be moved relative to elongate outer tube 210 (FIG. 67A) in any direction to cause the articulation of articulating section 230 (see FIGS. 3 and 5) in that same direction.

When it is desired to fix the position of articulating section 230 (see FIGS. 3 and 5), articulation lock trigger 230 may further be pulled proximally, or depressed, from the unlocked position (FIG. 72) to the locked position (FIG. 73). As shown in FIG. 73, when articulation lock trigger 6310 is moved to the locked position, the pivoting of articulation lock trigger 6310 with respect to shaft 6320 causes side protrusions 6329 to cam along proximally-facing surfaces 6317 of flanges 6312 from unlocked position segment 6317b to locked position segment 6317c. Locked position segment 6317c is configured such that, as side protrusions 6329 cam therealong, i.e., as articulation lock trigger 6310 is depressed from the unlocked position to the locked position, locked position segments 6317c of proximally-facing surfaces 6317 of flanges 6312 urge side protrusions 6329 and, thus, shaft 6320 proximally. As side protrusions 6329 and shaft 6320 are translated proximally, articulation lock plate 6324, disposed at distal end 6322 of shaft 6320, pinches, or frictionally-engages, the sphere (see FIGS. 70A-70C) to the proximal surface of spherical-shaped cavity 6350, preventing articulation of handle assembly 6350 with respect to elongate outer tube 210 (FIG. 67A) and, thus, fixing the position of articulation section 230 with respect to longitudinal axis "X" (see FIGS. 3 and 5).

Any of the locking mechanisms described above in connection with any of the embodiments discussed herein may be provided for locking, or fixing articulation lock trigger 6310 in the locked position. Accordingly, with the use of a locking mechanism, a surgeon need not continually retain, e.g., squeeze, articulation lock trigger 6310 toward the locked position. However, when it is desired to release articulation lock trigger 6310 from the locked position, e.g., when it is desired to re-position articulating section 230 (see FIGS. 3 and 5), articulation lock trigger 6310 may be moved distally to release the locking mechanism, allowing articulation lock trigger 6310, shaft 6320, and lock plate 6324 to move distally back to the unlocked position.

With reference now to FIGS. 76-79, another embodiment of an articulation mechanism is shown as 7300. Articulation mechanism 7300 is similar to articulation mechanism 6300 and, thus, only the differences will be described hereinbelow to avoid repetition. More particularly, as opposed to articulation mechanism 6300, which, as discussed above with reference to FIGS. 71A-75, includes specifically-configured proximal surfaces 6317 of flanges 6312 of articulation lock trigger 6310 that cam with respect to protrusions 6329 of shaft 6320 to move articulation mechanism 6300 between the shipping and use positions, articulation mechanism 7300 includes a pair of linkages 7380 pivotably engaged to both articulation lock trigger 7310 and shaft 7320 and a spring-loaded latch 7370 for longitudinally translating shaft 7320 with respect to handle assembly 7350 from the shipping position to the use position(s), e.g., the unlocked use position and the locked use position, upon pulling of articulation lock trigger 7310 with respect to shaft 7320 about pivot 7360 from the shipping position to the use position.

Referring momentarily to FIG. 78, articulation mechanism 7300, similar to articulation mechanism 6300, includes a slot 7314 defined within each of flanges 7312 of articulation lock trigger 7310. Each slot 7314 is configured to retain a tab 7338 of an arm 7336 of cable plate 7330 therein (see FIG. 79). Slots 7314, including grooves 7315 defined therein, are specifically configured and dimensioned such that tabs 7338 of arms 7336 are translated along slots 7314 as articulation lock trigger 7310 is depressed from the shipping position to the use position to translate cable plate 7330 proximally, thereby tensioning cables 240 (FIG. 15). In other words, a similar configuration as discussed above in relation to articulation mechanism 6300 is used in articulation mechanism 7300 to tension cables 240 (FIG. 15) upon movement of articulation lock trigger 7310 from the shipping position to the use position.

Referring now to FIGS. 76-77, and as mentioned above, articulation mechanism 7300 includes a pair of linkages 7380 pivotably engaged to both articulation lock trigger 7310 and shaft 7320 and a spring-loaded latch, or latch spring 7370 for transitioning articulation mechanism 7300 with respect to handle assembly 7350 between the shipping position, the unlocked use position and the locked use position.

More specifically, linkages 7380 are pivotably engaged to flanges 7312 via apertures 7316 defined within articulation lock trigger 7310 at first ends 7382 of linkages 7380 and are pivotably engaged to side protrusions 7329 disposed on opposite longitudinal sides 7323 of shaft 7320 at second ends 7384 of linkages 7384. As best shown in FIG. 78, apertures 7316 defined within flanges 7312 of articulation lock trigger 7310 each include a transverse rib 7318 on an inner surface thereof to facilitate securing of linkages 7380 to articulation lock trigger 7310 during assembly.

As can be appreciated, upon proximal pulling, or pivoting of articulation lock trigger 7310 with respect to shaft 7320 about pivot 7360, linkages 7380 are pivoted with respect to flanges 7312 at first ends 7382 thereof and are translated proximally and pivoted with respect to shaft 7320 at second ends 7384 thereof, urging shaft 7320 proximally. Similarly, upon release, or distal pushing of articulation lock trigger 7310, linkages 7380 are translated distally, urging shaft 7320 distally.

Initially, articulation mechanism 7300 is in a shipping position wherein articulation lock trigger 7310, shaft 7320 and lock plate 7324 are in respective distal-most positions. Latch spring 7370, which is coupled to handle assembly 7350 and is positioned toward a proximal end 7321 of shaft 7320, is spaced-apart, or disengaged from shaft 7320 when articulation mechanism 7300 is in the shipping position. Further, in the shipping position, tabs 7338 of arms 7336 of cable plate 7330 are disposed within grooves 7315 of flanges 7312 of articulation lock trigger 7310 such that articulation cables 240 (FIG. 15) are substantially un-tensioned.

In order to transition articulation mechanism 7300 from the shipping position to the use position, as shown in FIG. 76, articulation lock trigger 7310 is pulled, or depressed proximally. Upon pivoting of articulation lock trigger 7310 with respect to shaft 7320 about pivot 7360, tabs 7338 of arms 7336 of cable plate 7330 are moved proximally from grooves 7315 to slots 7314 defined within flanges 7312 of articulation lock trigger 7310 to tension cables 240 (FIG. 15). At the same time, linkages 7380 pivot and urge shaft 7320 proximally to the use position. As articulation lock trigger 7310 is depressed further, shaft 7320 is translated further proximally such that latch spring 7370 cams over the bottom surface of proximal end 7321 of shaft 7320. As shown in FIG. 77, latch spring 7370 eventually engages a notch (not explicitly shown) disposed on the bottom surface of shaft 7320 to retain articulation mechanism 7300 in the use position. Thus, once latch spring 7370 is engaged within the notch of shaft 7320, the release of articulation lock trigger 7310, from the locked use position, only returns articulation mechanism to the unlocked use position (and not the shipping position).

As in the previous embodiments, once articulation mechanism 7300 has been transitioned from the shipping position to the use position, articulation mechanism 7300 may further be transitioned between an unlocked position and a locked position to permit and inhibit, respectively, articulation of articulating section 230 (see FIGS. 3 and 5). More specifically, the notch in the bottom surface of shaft 7320 has a sufficient length to permit longitudinal translation of shaft 7320 with respect to latch spring 7370, i.e., to permit longitudinal translation of latch spring 7370 relative to shaft 7320 from a first end of the notch to a second end of the notch, between the more-distal unlocked position and the more-proximal locked position. Thus, although the engagement of latch spring 7370 within the notch of shaft 7320 permits articulation mechanism 7300 to transition between the unlocked use position and the locked use position, the engagement of latch spring 7370 within the notch prevents articulation mechanism 7300 from returning to the shipping position. Further, any of the locking mechanisms described above in connection with any of the embodiments discussed herein may be provided for locking (or unlocking) articulation mechanism 7300 in the locked (or unlocked) position.

As best shown in FIG. 76, articulation mechanism 7300 is configured to permit articulation mechanism 7300 to be reset, allowing articulation mechanism 7300 to return to the shipping position after the initial transition from the shipping position to the use position. Such a feature allows, for example, a manufacturer to test the instrument in all three positions (the shipping, unlocked use and locked use positions) without permanently locking-out the shipping position and/or permits a surgeon to restore the articulation mechanism 7300 back to the shipping position where there may be an extended length of time between uses.

With continued reference to FIG. 76, in order to reset articulation mechanism 7300 back to the shipping position, a manufacturer or surgeon may insert any suitable elongated rod-like member (not shown), upwardly into handle assembly 7350 through trigger slot 7390. Trigger slot 7390 is an opening defined within handle assembly 7350 to permit articulation lock trigger 7310 to move between the shipping, unlocked use, and locked use positions. By inserting any suitable member (not shown) through the trigger slot 7390, the manufacturer or surgeon may manually disengage latch spring 7370 from the notch defined within shaft 7320, thereby permitting shaft 7320, and articulation lock trigger 7310 to return to the distal-most, or shipping position. Releasing latch spring 7370 also allows tabs 7338 of arms 7336 of cable plate 7330 to return back to grooves 7315 defined within flanges 7312 of articulation lock trigger 7310 to un-tension cables 240 (FIG. 15).

Turning now to FIGS. 80-88, another embodiment of an articulation mechanism is shown as 8300. Articulation mechanism 8300, as in previous embodiments, is transitionable between a shipping position and a use position, the use position including an unlocked position and a locked position. Articulation mechanism 8300 is disposed within handle assembly 8350 and includes an articulation lock trigger 8310 pivotably coupled to a shaft 8320 about a pivot 8360. Shaft 8320 includes a lock plate 8324 disposed at a distal end 8321 thereof. A cable plate 8330 is positioned distal of and adjacent lock plate 8324 and includes a pair of arms 8336 extending proximally therefrom. A pair of linkages 8370 disposed on either side of articulation mechanism 8300 are pivotably coupled at first ends 8372 thereof to articulation lock trigger 8310 and at second ends 8374 thereof to shaft 8320 such that pivotal movement of articulation lock trigger 8310 with respect to shaft 8320 effects longitudinal movement of shaft 8320. A slider 8380, configured for tensioning cables 240 (FIG. 15) upon the depression of articulation lock trigger 8310 from the shipping to the use position, is disposed about shaft 8320 toward a proximal end 8322 thereof. A pair of spring-loaded latches 8390, 8395 rotatable about a pivot 8399 are also provided for transitioning and maintaining articulation mechanism 8300 in each of the shipping, unlocked use, and locked use positions.

With reference to FIGS. 80-83, cable plate 8330 has four (4) ferrules 8334 positioned annularly therearound for securely retaining the proximal ends of articulation cables $240_{A-D}$ (FIG. 15) therein. Each arm 8336 of cable plate 8330 further includes a post 8338 disposed at a proximal end 8337 (see FIG. 83) thereof that extends outwardly therefrom. Arms 8336 of cable plate 8330 extend proximally through an aperture (not explicitly shown) defined within lock plate 8324 to extend along longitudinal sides 8326 of shaft 8320, while cable plate 8330 is positioned distally of lock plate 8324 when articulation mechanism 8300 is fully assembled. Slider 8380 straddles shaft 8320 and includes a pair of legs 8382 extending downwardly along opposite longitudinal sides 8326 of shaft 8320 toward proximal end 8322 thereof. Each leg 8382 includes an aperture 8384 defined therein that is dimensioned and configured to secure a post 8338 of one of arms 8336 of cable plate 8330. As can be appreciated, with posts 8338 of arms 8336 of cable plate 8330 secured within apertures 8384 of legs 8382 of slider 8380, cable plate 8330 is translated longitudinally upon longitudinal translation of slider 8380. Thus, as slider 8380 is translated proximally, cable plate 8330 is similarly translated proximally to tension cables 240 (FIG. 15).

As mentioned above, with continued reference to FIGS. 80-83, articulation lock trigger 8310 is pivotable about pivot 8360 between a shipping position and a use position (and articulation lock trigger 8310 is further moveable between an unlocked position and a locked position once disposed in the use position). More specifically, articulation lock trigger 8310 includes a pair of flanges 8312 that extend upwardly on opposite longitudinal sides 8326 of shaft 8320, ultimately coupling to pivot 8360 for pivotably-engaging articulation lock trigger 8310 to shaft 8320. Flanges 8312 of articulation lock trigger 8310 each define a specifically-configured proximally-facing surface. Similar to articulation lock trigger 6310 of articulation mechanism 6300, proximal-facing surfaces 8316 of articulation lock trigger 8310 define three distinctly configured segments: a shipping segment 8316a, an unlocked use segment 8316b, and a locked use segment 8316c.

Figure 80:
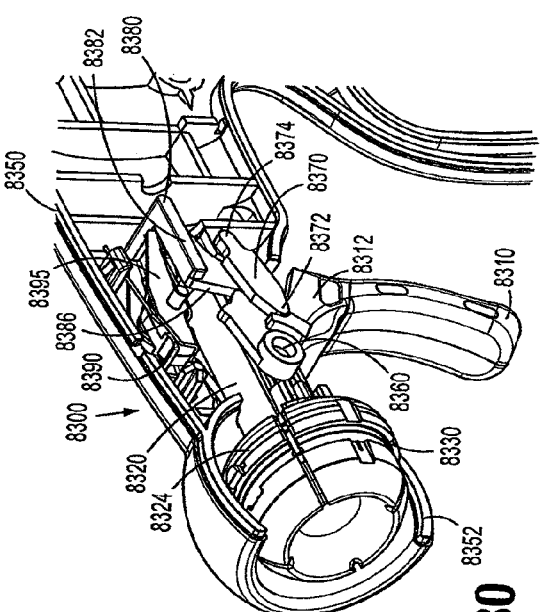
FIG. 80 is a front, perspective, cut-away view of another articulation mechanism in accordance with the present disclosure.
Figures 84, 85:
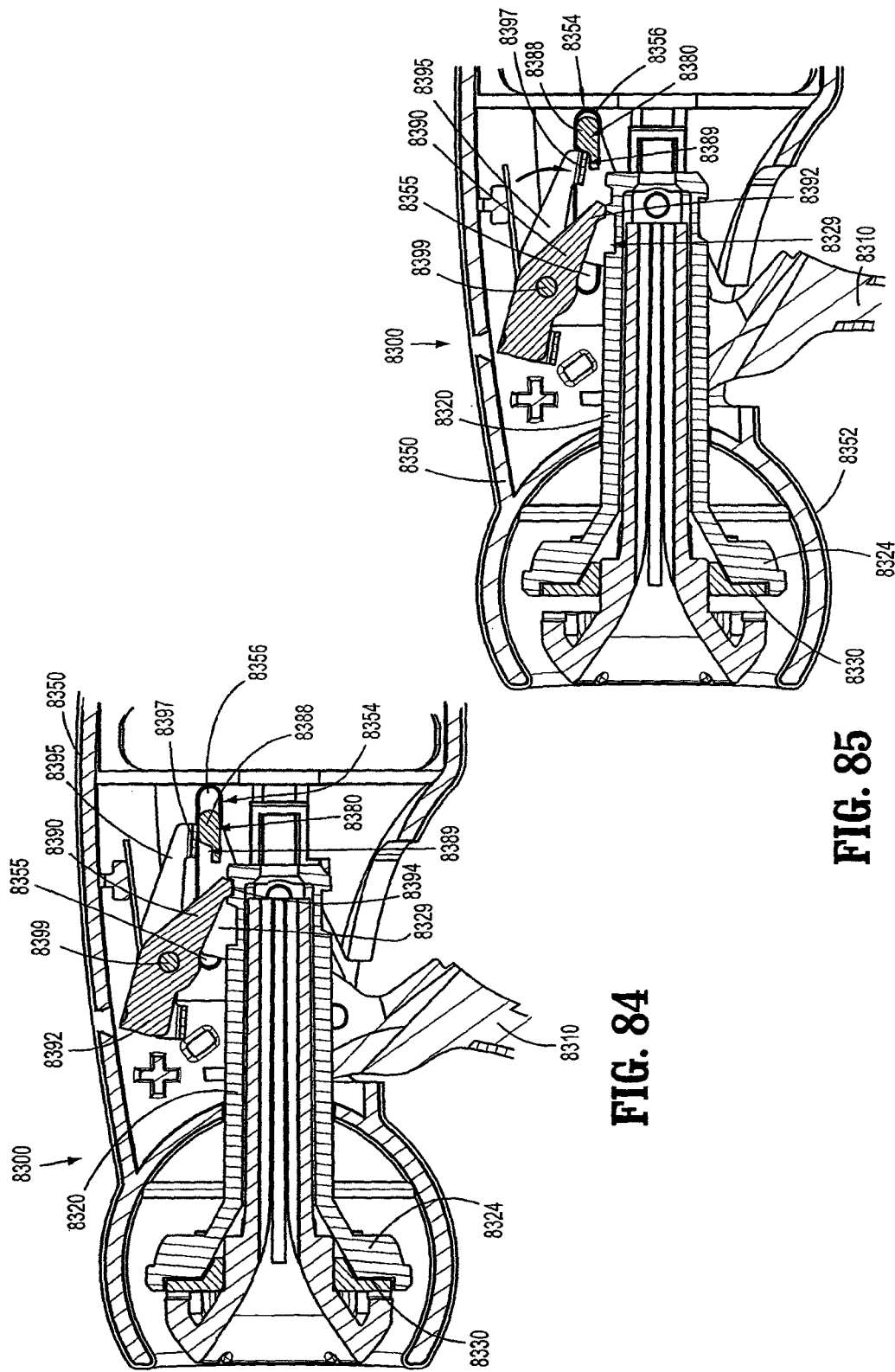
FIG. 84 is a side, cross-sectional view of the articulation mechanism of FIG. 80 shown in a shipping position.
FIG. 85 is a side, cross-sectional view of the articulation mechanism of FIG. 80 shown transitioning from the shipping position to a use position.
Figure 86:
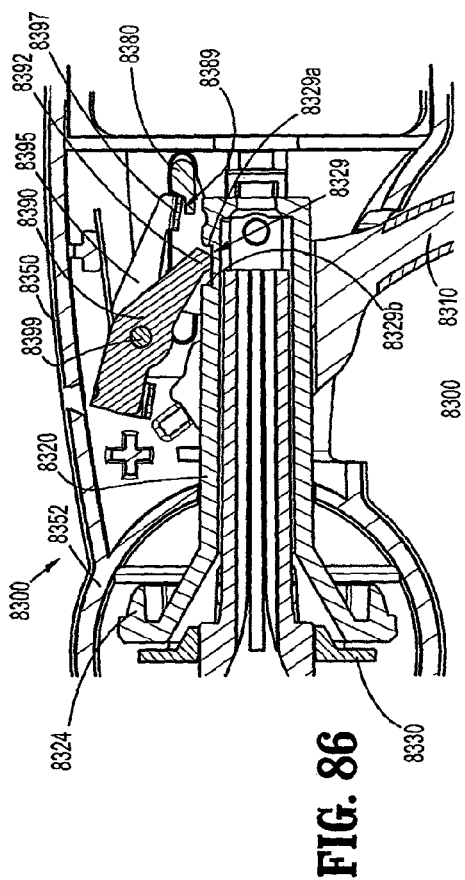
FIG. 86 is a side, cross-sectional view of the articulation mechanism of FIG. 80 shown moving to a locked position.
Figure 87:
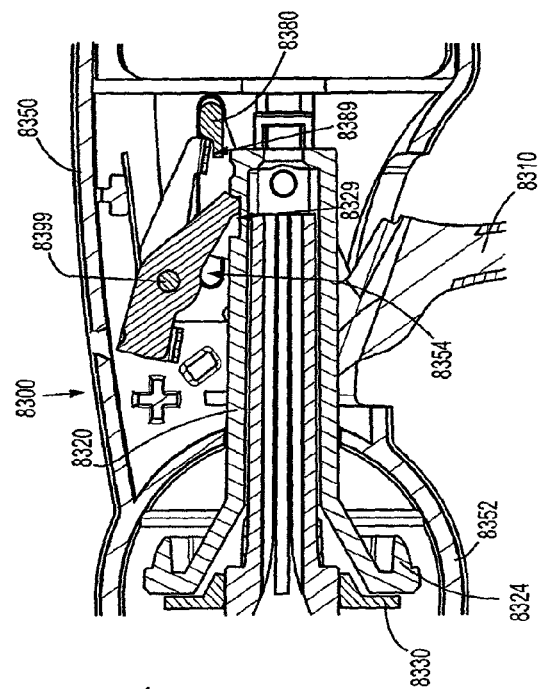
FIG. 87 is a side, cross-sectional view of the articulation mechanism of FIG. 80 shown in an unlocked position.

When in the shipping position, as shown in FIGS. 80 and 84, articulation lock trigger 8310 is in a distal-most position and distally-facing surfaces 8386 of legs 8382 of slider 8380 are engaged within shipping segments 8316a of flanges 8312 of articulation lock trigger 8310. The configuration of shipping segments 8316a is such that slider 8380 is in a distal-most position when engaged within shipping segments 8316a of articulation lock trigger 8310 and, accordingly, such that arms 8336, cable plate 8330, and cables 240 (FIG. 15) are in a distal-most, or un-tensioned position.

Figure 81:
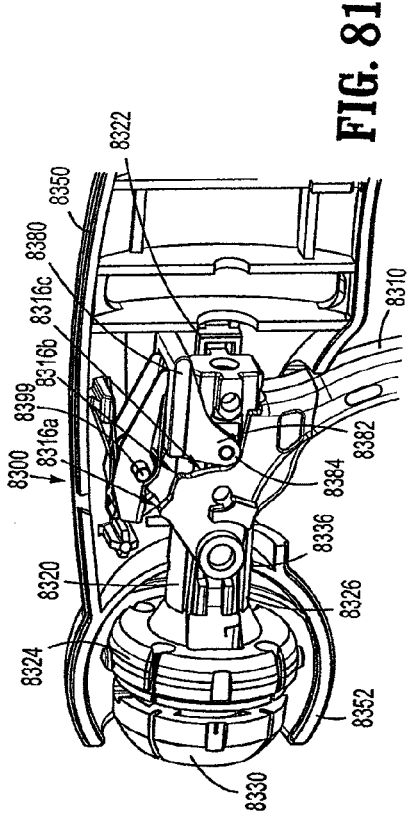
FIG. 81 is a rear, perspective, cut-away view of the articulation mechanism of FIG. 80.

When articulation lock trigger 8310 is pulled proximally, as shown in FIGS. 81 and 85, proximal surfaces 8316 of flanges 8312 of articulation lock trigger 8310 cam with respect to distal surfaces 8386 of legs 8382 of slider 8380. Flanges 8312 cam with respect to legs 8382 such that legs 8382 are moved relative to flanges 8312 over humps 8318 defined between shipping segments 8316*a* and unlocked use segments 8316*b* of flanges 8312. As articulation lock trigger 8310 is further pulled proximally, legs 8382 clear humps 8318 and are engaged within unlocked use segments 8316*b*. As legs 8382 are moved into engagement with unlocked use segments 8316*b*, the configuration of humps 8318 and unlocked use segments 8316*b* urge legs 8382, and, thus slider 8380 proximally. In other words, unlocked use segments 8316*b* protrude further proximally with respect to slider 8380 than shipping segments 8316*a*. As a result, when articulation lock trigger 8310 is pulled to the use position, slider 8380 is translated proximally thereby, as mentioned above, translating cable plate 8330 proximally and tensioning cables 240 (FIG. 15).

Figure 83:
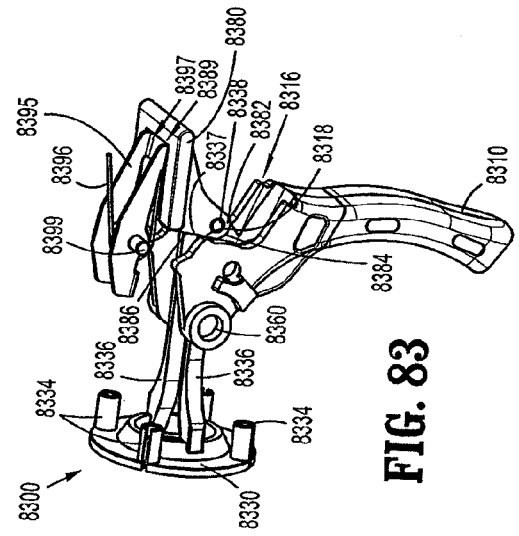
FIG. 83 is an isolated, perspective view of the articulation mechanism of FIG. 80 showing a slider engaged to a cable plate.

With reference now to FIGS. 84-85 in conjunction with FIGS. 80, 81 and 83, slider 8380 includes a pair of side rails 8388 slidably engaged within grooves 8354 defined within opposing inner surfaces of handle assembly 8350. The engagement of side rails 8388 within grooves 8354 limits the range of motion of slider 8380. More specifically, when side rails 8388 of slider 8380 are disposed at a distal end 8355 of grooves 8354, slider 8380, and thus cable plate 8330, are in a distal-most, or shipping position wherein cables 240 (FIG. 15) are substantially un-tensioned and articulation lock trigger 8310 is in the shipping position such that legs 8382 of slider 8380 are engaged within shipping segments 8316*a* of flanges 8312 of articulation lock trigger 8310. When slider 8380 is translated proximally, e.g., when articulation lock trigger 8310 is pulled proximally from the shipping position to the use position, as discussed above, slider 8380 and, thus side rails 8388 are moved to proximal ends 8356 of grooves 8354 and cable plate 8330 is translated proximally to tension cables 240 (FIG. 15).

As mentioned above, and as shown in FIGS. 80-82, linkage 8370 couples articulation lock trigger 8310 to shaft 8320 such that proximal pulling of articulation lock trigger 8310 effects proximal longitudinal translation of shaft 8320, and such that releasing or returning articulation lock trigger 8310 distally effects distal longitudinal translation of shaft 8320.

Accordingly, pulling, or depressing articulation lock trigger 8310 initially from the shipping position to the use position(s) moves slider 8380 proximally to tension cables 240 (FIG. 15) and similarly moves shaft 8320 proximally to the use positions. Once slider 8380 has been moved to proximal ends 8356 of grooves 8354, and once shaft 8320 has been moved to the use position(s), spring-loaded latches 8390, 8395 engage shaft 8320 and slider 8380, respectively, to retain articulation mechanism 8300 in the use position. Accordingly, once retained in the use position, articulation mechanism 8300 may be transitioned between the unlocked position and the locked position for fixing and/or unlocking the relative position of articulation section 230 with respect to longitudinal axis "X" (see FIGS. 3 and 5).

Figure 82:
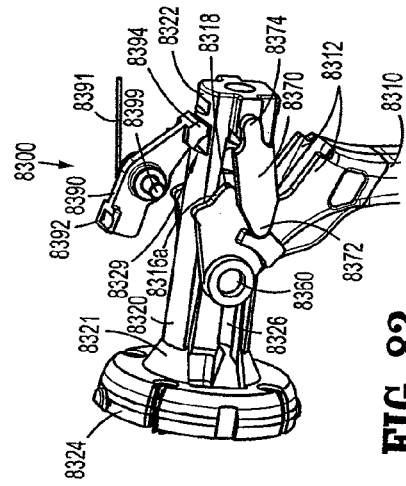
FIG. 82 is an isolated, perspective view of the articulation mechanism of FIG. 80 showing a shaft coupled to an articulation lock trigger.

Referring now to FIGS. 84-85, in conjunction with FIGS. 82-83, when articulation mechanism 8300 is disposed in the shipping position, spring-loaded latches 8390, 8395 are disengaged from shaft 8320 and slider 8380, respectively. More particularly, proximal crossbar 8397 of latch 8395 is displaced from recess 8389 defined within slider 8380 when articulation mechanism 8300 is disposed in the shipping position and proximal finger 8392 of latch 8390 is disengaged from recess 8329 defined within shaft 8320 when articulation mechanism 8300 is disposed in the shipping position.

Latch 8395 is pivotable about pivot 8399 and includes a proximal crossbar 8397 and a distal crossbar 8398 disposed at opposite longitudinal ends of latch 8395. A spring 8396 biases latch 8395 about pivot 8399 in a clockwise direction (as illustrated in FIG. 83). In other words, spring 8396 biases proximal cross-bar 8397 of latch 8396 downwardly toward slider 8380. Latch 8390 includes proximal and distal fingers 8392, 8394, respectively, and is similarly pivotable about pivot 8399. Latch 8390 is also spring-biased, by spring 8391, in a clockwise direction (as illustrated in FIG. 82) such that proximal finger 8392 is biased downwardly toward shaft 8320.

Upon proximal pulling of articulation lock trigger 8310 from the shipping position to the use position, spring-loaded latches 8390, 8395 are engaged within respective recess 8329, 8389 defined within shaft 8320 and slider 8380, respectively, to maintain articulation mechanism 8300 in the use position wherein articulation lock trigger 8310 may further be moved between the unlocked and locked positions. More particularly, as pulling of articulation lock trigger 8310 translates slider 8380 proximally from distal ends 8355 of grooves 8354 to proximal ends 8356 of grooves 8354, slider 8380 cams proximally along spring-biased latch 8395 until proximal crossbar 8397 of latch 8395 is biased into engagement within recess 8389 defined within slider 8380. Once engaged within recess 8389, crossbar 8397 of latch 8395, due to the spring bias of latch 8395, in maintained within recess 8389, thereby preventing slider 8380 form returning to the shipping position, and, thus, maintaining articulation cables 240 (FIG. 15) in the tensioned state.

Further, with slider 8380 fixed in position at proximal ends 8356 of grooves 8354 by spring biased latch 8395, articulation cables 240 (FIG. 15) are maintained in a constant, tensioned state. In other words, fixing slider 8380 fixes the relative position of cable plate 8330, thus fixing the tension imparted to articulation cables 240 (FIG. 15), regardless of the position of shaft 8320 and/or articulation lock trigger 8310 (i.e., regardless of whether articulation mechanism 8300 is in the unlocked or the locked position).

With continued reference to FIGS. 82-85, as shaft 8320 is translated proximally, i.e., as articulation lock trigger 8310 is depressed from the shipping position to the use position, shaft 8320 cams proximally along proximal finger 8392 of latch 8390 such that proximal finger 8392 is eventually biased into engagement with recess 8329 defined within shaft 8320. Similar to latch 8395, latch 8390 is maintained in engagement within recess 8329 of shaft 8320 due to the biasing-effect of spring 8391. Accordingly, latch 8390, when engaged to shaft 8320, maintains shaft 8320 in more-proximal, use position.

When proximal finger 8392 is engaged within recess 8329 of shaft 8320, shaft 8320 is prevented from returning to the distal-most, or shipping position. However, recess 8329 defines a sufficient length such that shaft 8320 may still translated longitudinally with respect to latch 8390 when latch 8390 is engaged thereto.

More specifically, with proximal finger 8392 of latch 8390 disposed within recess 8329 of shaft 8320, shaft 8320 may be longitudinally translated with respect to latch 8390 such that proximal finger 8392 is translated from proximal end 8329*a* of recess 8329 to distal end 8329*b* of recess 8329 of shaft 8320. When proximal finger 8392 is disposed at proximal end 8329*a* of recess 8329, shaft 8320 is disposed in a more-distal position such that lock plate 8324 is in an unlocked position, allowing handle assembly 8350 to be articulated with respect to longitudinal axis "X" to similarly articulate articulation section 230 (see FIGS. 3 and 5) with respect to longitudinal axis "X." This configuration corresponds to the unlocked, use position of articulation mechanism 8300.

When articulation lock trigger 8310 is pivoted proximally, i.e., depressed, from the unlocked position toward the locked position, shaft 8320 is translated proximally with respect to latch 8390 such that latch 8390 is moved to distal end 8329b of recess 8329 of shaft 8320. As shaft 8320 is moved proximally, lock plate 8324 is similarly moved proximally to pinch, or frictionally-engage the sphere (see FIGS. 70A-70C) to the proximal surface of spherical-shaped cavity 8352, preventing articulation of handle assembly 8350 with respect to elongate outer tube 210 (FIG. 67A) and, thus, fixing the position of articulation section 230 with respect to longitudinal axis "X" (see FIGS. 3 and 5). Any of the locking mechanisms described herein may be provided for fixing the position of articulation section 230 (see FIGS. 3 and 5) relative to longitudinal axis "X." Accordingly, articulation lock trigger 8310 may be selectively depressible to lock and unlock the relative position of articulation section 230 (see FIGS. 3 and 5) with respect to longitudinal axis "X."

If it is desired to "reset" articulation mechanism 8300, i.e., to return articulation mechanism 8300 to the shipping position, latches 8390 and 8395 may be manually pivoted (as shown in the present embodiment in a counter-clockwise direction) about pivot 8399 to disengage latches 8390 and 8395 from shaft 8329 and slider 8380, respectively, such that cables 240 (FIG. 15) are returned to the un-tensioned state and such that articulation lock trigger 8310 and shaft 8320 are returned to their respective shipping positions.

Figure 88:
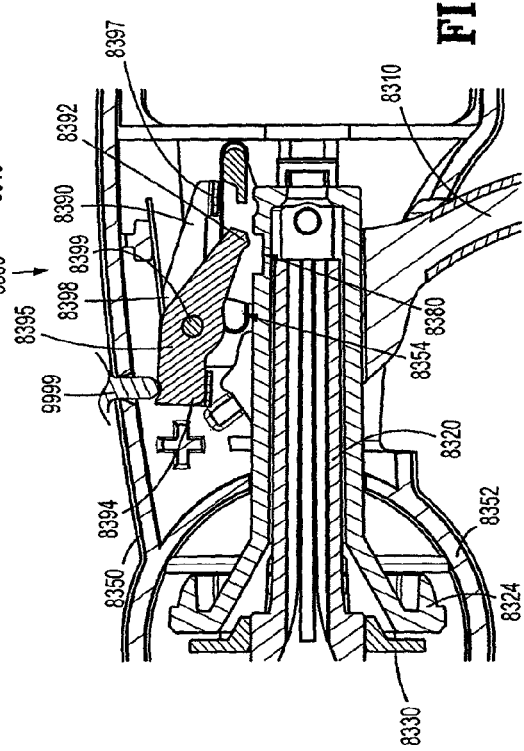
FIG. 88 is a side, cross-sectional view of the articulation mechanism of FIG. 80 shown being reset back to the shipping position.

With reference now to FIG. 88, in order to "reset" articulation mechanism 8300, the user may insert an elongated instrument 9999 (or any other suitable elongated member) through an aperture 8357 defined within the upper portion of handle assembly 8350. As instrument 9999 is translated through aperture 8357, instrument 9999 eventually contacts distal ends 8394, 8398 of latches 8390, 8395, respectively, urging distal ends 8394, 8398 of respective latches 8390, 8395 to pivot about pivot 8399 in a counter-clockwise direction (as illustrated in FIG. 88). As can be appreciated, urging latches 8390, 8395 in a counter-clockwise direction urges distal ends 8394, 8398, respectively downward and, thus, urges proximal ends 8392, 8397 upward, disengaging proximal ends 8392, 8397 of respective latches 8390, 8395 from recesses 8329, 8389 of shaft 8320 and slider 8380, respectively. As such, the disengagements of latches 8390 and 8395 from shaft 8320 and slider 8380, respectively, permits slider 8380 and shaft 8320 to be moved back to their respective shipping positions. Accordingly, as slider 8320 is moved distally, cable plate 8330 is similarly moved distally and cables 240 (FIG. 15) are un-tensioned. Shaft 8320 is similarly moved distally to the shipping position such that articulation mechanism 8300 is returned to the shipping position shown in FIGS. 83 and 84.

Referring now FIGS. 89-97, yet another embodiment of an articulation mechanism is shown by 9300. Articulation mechanism 9300 is similar to articulation mechanism 8300 and is transitionable between a shipping position, an unlocked use position, and a locked use position. As with articulation mechanism 8300, articulation mechanism 9300 is disposed within handle assembly 9350 and includes an articulation lock trigger 9310 pivotably coupled to a shaft 9320 via a pivot 9360 and a pair of linkages 9390 such that proximal pulling, or rotation of articulation lock trigger 9310 effects proximal longitudinal movement of shaft 9320. Shaft 9320 includes a lock plate 9324 disposed at a distal end 9322 thereof. A cable plate 9330 including four (4) ferrules 9332 is configured to secure the proximal ends of cables 240 (FIG. 15) therein. Cable plate 9330 is positioned adjacent and distal of lock plate 9324 and includes a pair of arms 9336 extending therefrom. Arms 9336 of cable plate 9330 extend proximally through an aperture defined within lock plate 9324 and along shaft 9320. A slider 9370 configured for tensioning cables 240 (FIG. 15) upon the initial depression of articulation lock trigger 9310 from the shipping position to the use position(s) is disposed on shaft 9320 toward a proximal end 9323 thereof and is slidable with respect to shaft 9320 within a pair of grooves 9352 defined within handle assembly 9350. A rocker 9380 is rotatable about a pivot 9382 for retaining slider 9370 in the proximal, use position once articulation lock trigger 9310 is moved from the shipping position to the use position. As will be described below, rocker 9380 is manually resettable, allowing a user to return articulation mechanism 9300 from the use position(s) to the shipping position.

With continued reference now to FIGS. 89-97, articulation lock trigger 9310 includes a pair of flanges 9312 that extend upwardly on either side of shaft 9320 and are pivotally engaged to shaft 9320 via pivot 9360. Flanges 9312 include specifically-configured proximal surface segments 9314 that are shaped to rotate rocker 9380 upon depression of articulation lock trigger 9310 from the shipping position to the use position to thereby urge slider 9370 proximally and retain slider 9370 in the proximal-most, or use position.

Figure 89:
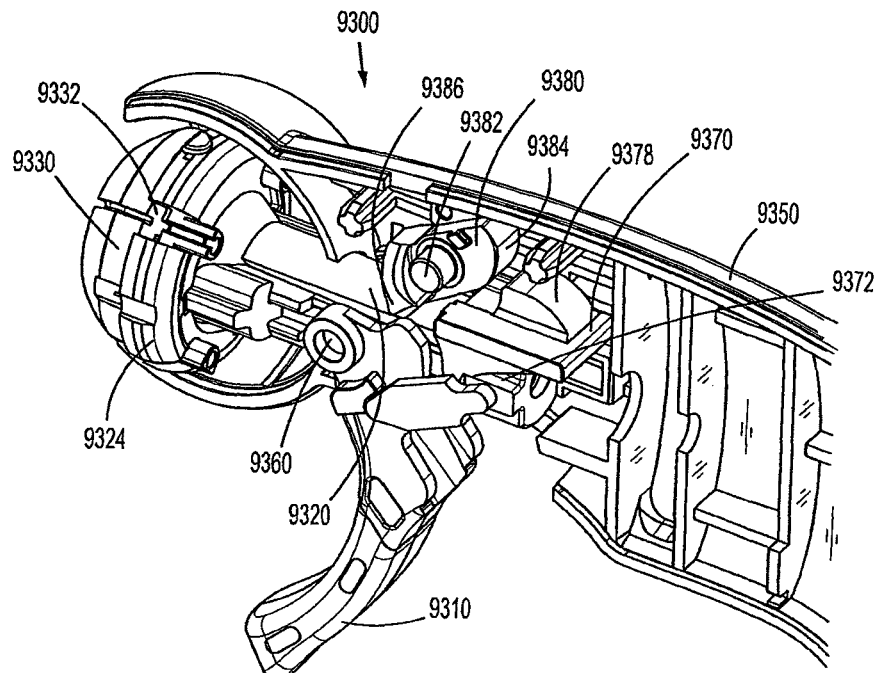
FIG. 89 is a rear, perspective cut-away view of yet another articulation mechanism in accordance with the present disclosure.
Figure 90:
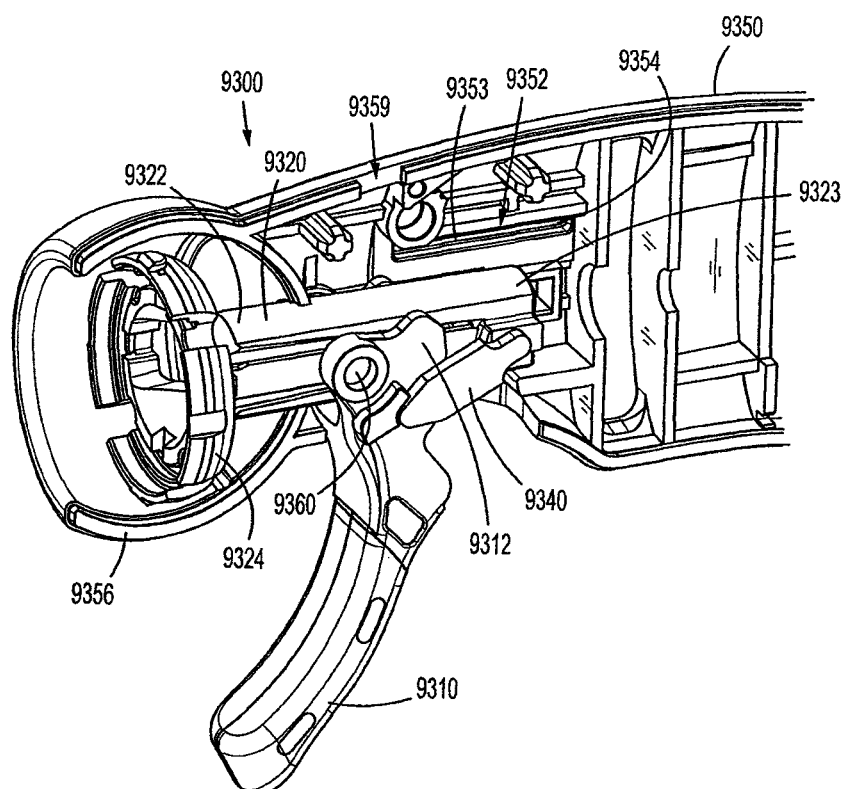
FIG. 90 is a front, perspective cut-away view of the articulation mechanism of FIG. 89 shown in a shipping position.
Figure 91:
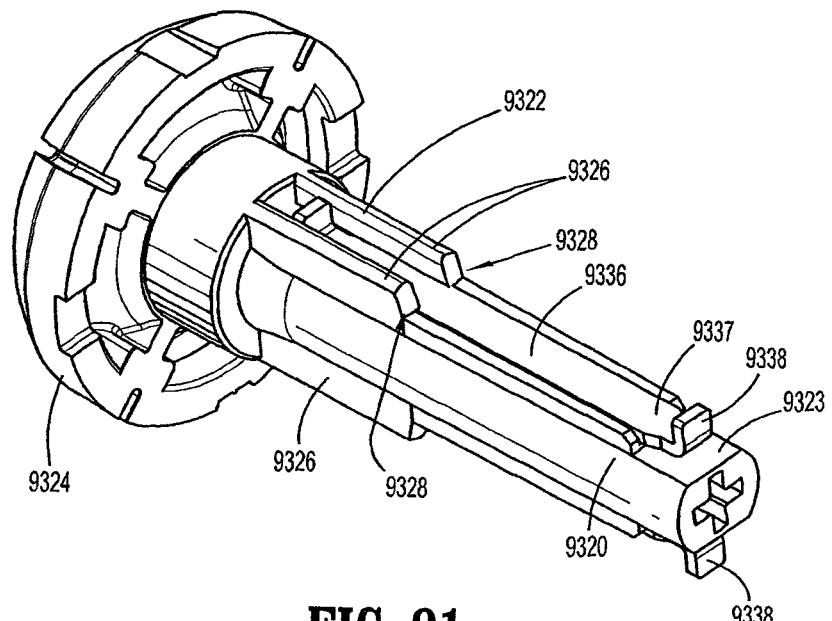
FIG. 91 is an isolated, perspective view of a shaft and cable plate of the articulation mechanism of FIG. 89.
Figure 92:
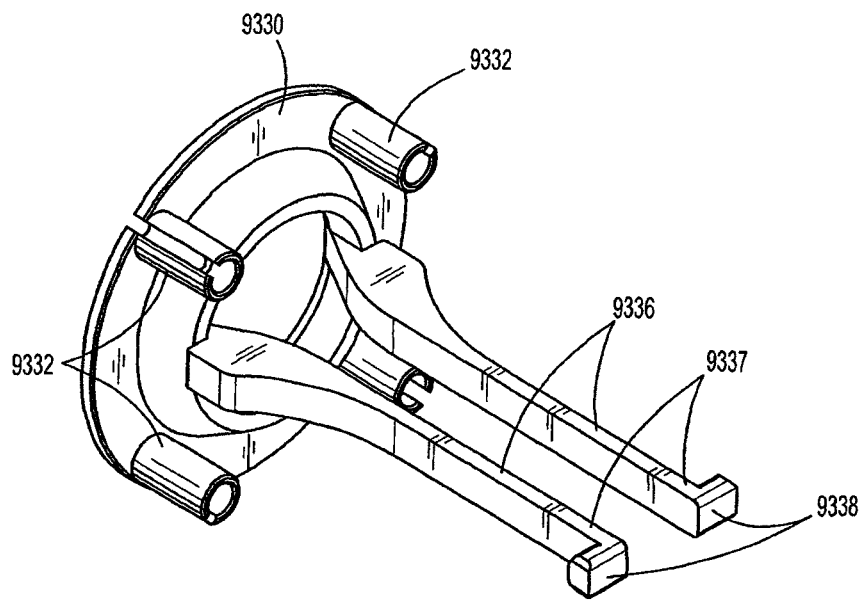
FIG. 92 is an isolated, perspective view of the cable plate of the articulation mechanism of FIG. 89.
Figure 93:
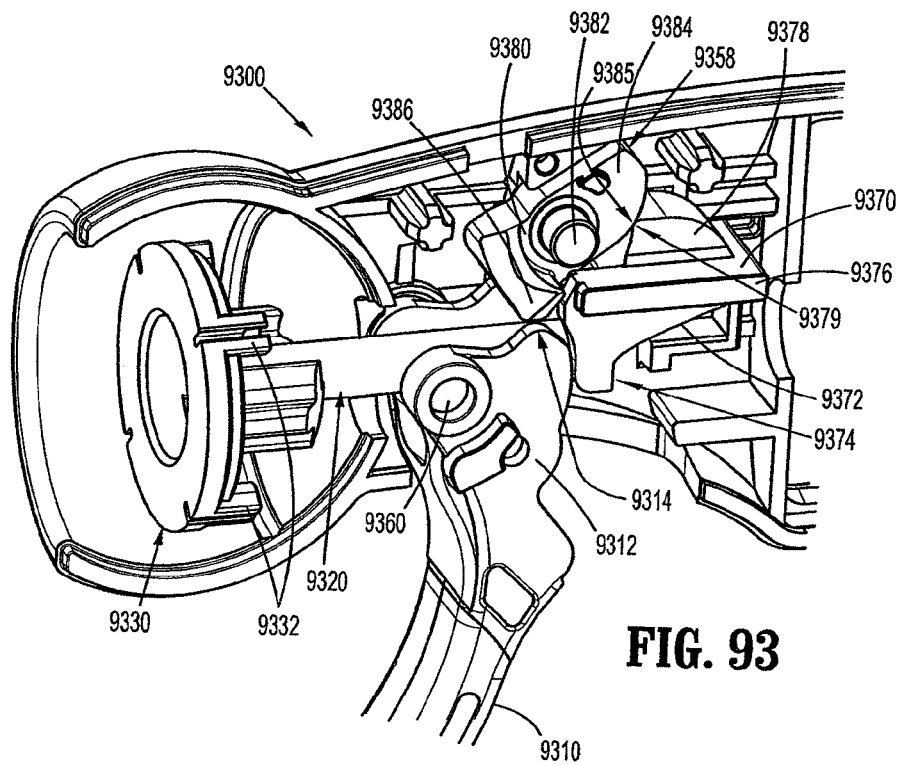
FIG. 93 is a front, perspective cut-away view of the articulation mechanism of FIG. 89 transitioning to a use position.

With reference to FIGS. 89-90, in conjunction with FIGS. 91-92, arms 9336 of cable plate 9330 extend proximally along shaft 9320. More specifically, arms 9336 are positioned between guide rails 9326 defined along shaft 9320. Guide rails 9326 permit longitudinal translation of aims 9336 with respect to shaft 9320 but otherwise maintain arms 9336 in fixed relation with respect to shaft 9320. Shaft 9320 may include specific features, e.g., a dovetail configuration 9328, to help retain arms 9336 therein. As best shown in FIG. 92, each arm 9336 includes a tab 9338 disposed at a proximal end 9337 thereof. Tabs 9338 protrude outwardly (away from shaft 9320) and are engaged within notches 9374 defined within legs 9372 of slider 9370, as best shown in FIG. 93. As can be appreciated, due to the engagement of tabs 9338 of arms 9336 of cable plate 9330 within notches 9374 of legs 9372 of slider 9370, when slider 9370 is translated proximally, e.g., via proximal depression of articulation lock trigger 9310, arms 9336 and, thus, cable plate 9330, are similarly translated proximally to thereby tension cables 240 (FIG. 15).

Referring now to FIG. 93-97, as mentioned above and similarly to articulation mechanism 8300, slider 9370 of articulation mechanism 9300 is disposed within grooves 9352 of handle assembly 9350, which limits the range of motion of slider 9370. More specifically, side rails 9376 of slider 9370 are moveable from distal ends 9353 of grooves 9352, wherein slider 9370 is in a distal-most position and, thus, wherein cables 240 (FIG. 15) are substantially un-tensioned (the shipping position) to proximal ends 9354 of grooves 9352, wherein slider 9370 is in a proximal-most position and, thus, wherein cables 240 (FIG. 15) are tensioned (the use position(s)).

Figure 94:
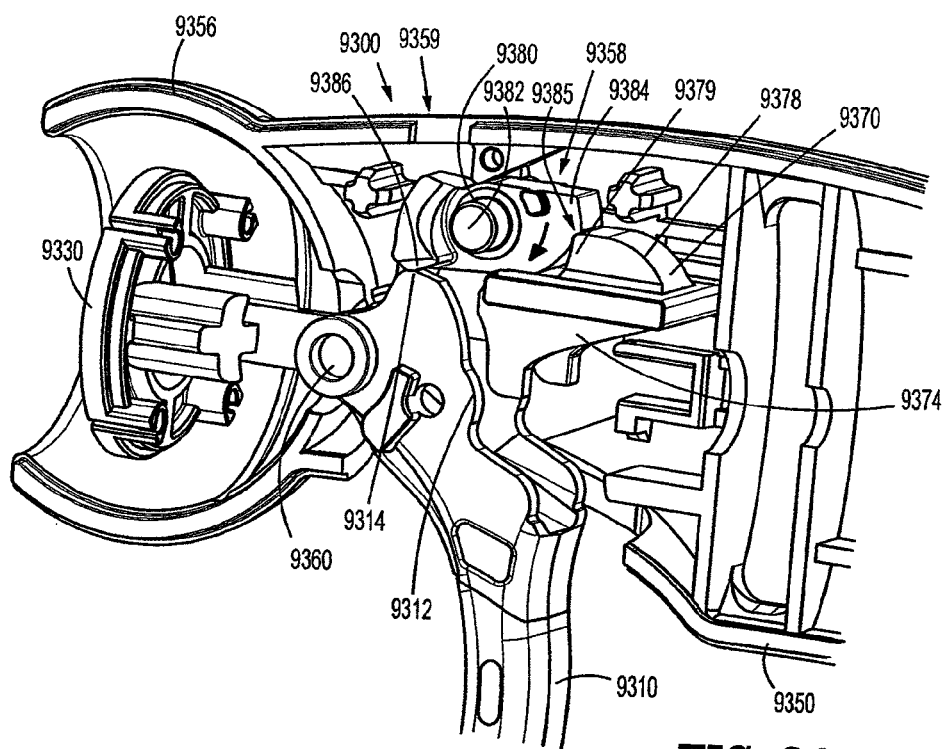
FIG. 94 is a rear, perspective cut-away view of the articulation mechanism of FIG. 89 shown in the use position.
Figure 95:
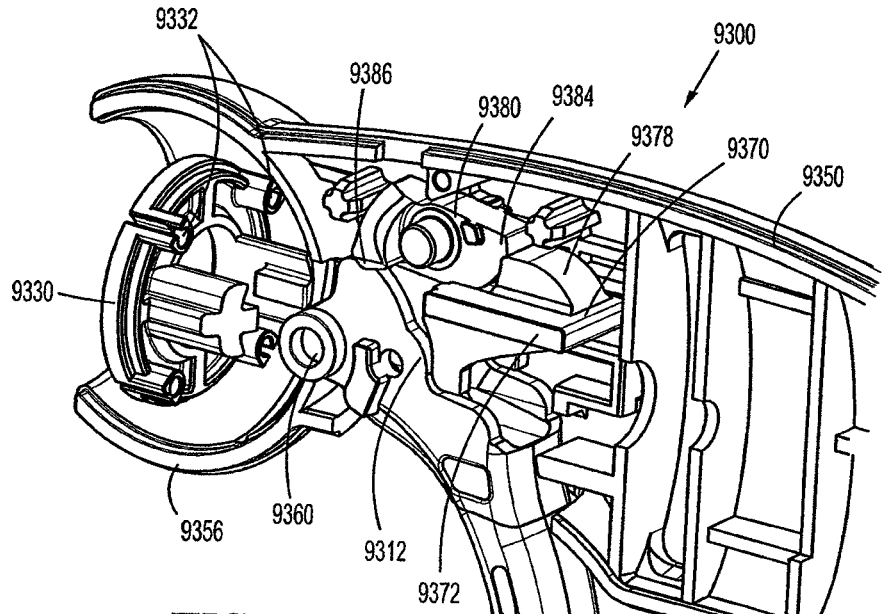
FIG. 95 is a rear, perspective cut-away view of the articulation mechanism of FIG. 89 wherein the shaft has been removed.
Figure 96:
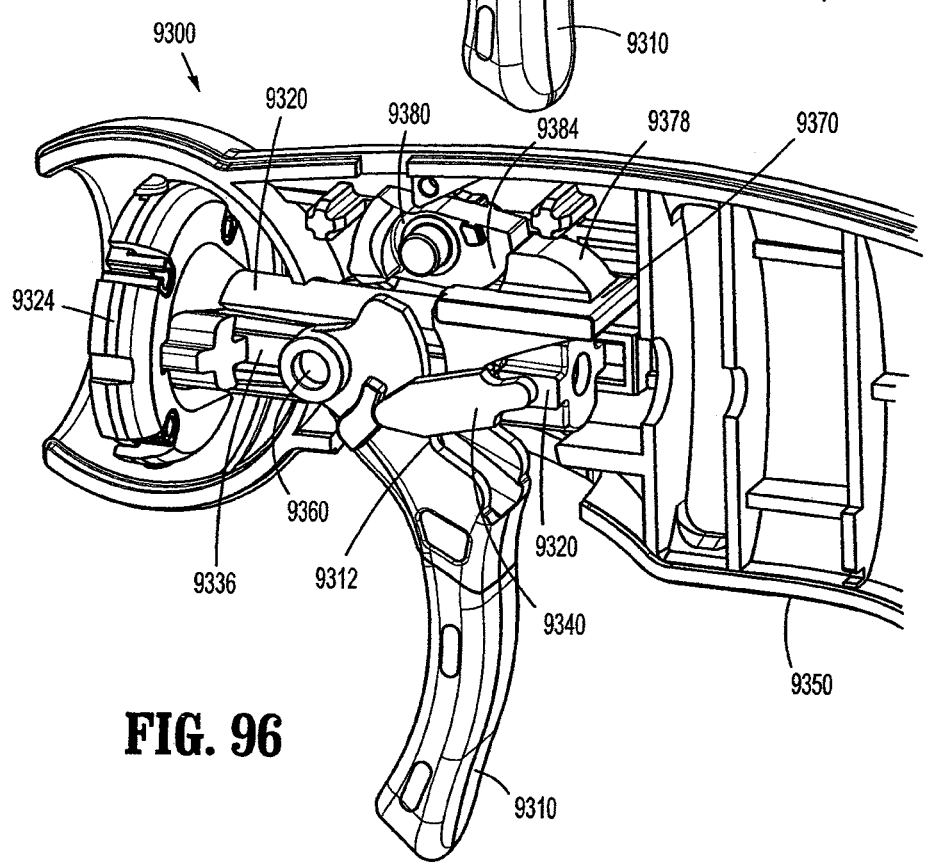
FIG. 96 is a rear, perspective cut-away view of the articulation mechanism of FIG. 95 with the shaft in place.

Rocker 9380 is pivotably engaged to handle assembly 9350 via pivot 9382. Rocker 9380 includes proximal and distal ends 9284, 9386, respectively. Distal end 9386 of rocker 9380 is configured to engage proximal segments 9314 of flanges 9312 of articulation lock trigger 9310 upon depression of articulation lock trigger 9310 from the shipping position to the use position such that rocker 9380 is rotated in a clockwise direction (as illustrated in FIG. 94). As rocker 9380 is rotated in a clockwise direction (as illustrated in FIG. 94), proximal end 9386 of rocker 9380 is disengaged from its initial position within notches 9358 defined within handle assembly 9350 and is rotated toward protrusion 9378 of slider 9370. Proximal end 9384 of rocker 9380 engages protrusion 9378 of slider 9370 and urges slider 9370 proximally to proximal ends 9354 of grooves 9352 (the use position), ultimately maintaining slider 9370 in the proximal position, thereby maintaining cables 240 (FIG. 15) in the tensioned state. When rocker 9380 is reset, e.g., when rocker 9380 is rotated in a counter-clockwise direction (as illustrated in FIG. 93), proximal end 9384 of rocker 9380 disengages from protrusion 9378 of slider 9370, allowing slider 9370 to return to distal end 9356 of grooves 9352 such that cables 240 (FIG. 15) are substantially un-tensioned.

The operation of articulation mechanism 9300 and, in particular, the transitioning of articulation mechanism 9300 from the shipping to the use positions (the unlocked and locked positions) will be described with reference to FIGS. 89-97. Initially, as shown in FIG. 89, articulation mechanism 9300 is disposed in a shipping position wherein articulation lock trigger 9310, shaft 9320, cable plate 9330 and slider 9370 are all disposed in distal-most positions and wherein cables 240 (FIG. 15) are substantially un-tensioned.

To move articulation mechanism 9300 from the shipping position to the use position, articulation lock trigger 9310 is depressed, or pulled proximally, as shown in FIG. 93. Upon pulling of articulation lock trigger 9310, as mentioned above, shaft 9320 is translated proximally (due to the coupling of articulation lock trigger 9310 and shaft 9320 via linkages 9340). Upon further pulling of articulation lock trigger 9310, proximal segment 9314 of flanges 9312 of articulation lock trigger 9310 engage distal end 9386 of rocker 9380 and rotate rocker 9380 in a clockwise direction (as illustrated in FIG. 94). Rotation of rocker 9380 causes proximal end 9384 of rocker 9380 to disengage notches 9358 of handle assembly 9350 and rotate toward slider 9370. Further rotation of rocker 9380 eventually engages proximal end 9384 of rocker 9380 with protrusion 9378 of slider 9370, thereby urging slider 9370 proximally with respect to shaft 9320 from distal end 9353 of grooves 9352 of handle assembly 9350 to proximal end 9354 of grooves 9352 of handle assembly 9350 to tension cables 240 (FIG. 15), as mentioned above. As can be appreciated, proximal end 9384 of rocker 9380 and protrusion 9378 of slider 9370 may include complementary-shaped surface features 9385, 9379 respectively, to help maintain the engagement between rocker 9380 and slider 9370 when rocker 9380 is rotated into engagement with slider 9370.

As best shown in FIG. 94, the engagement of proximal end 9384 of rocker 9380 with protrusion 9378 of slider 9370 fixedly retains slider 9370 at proximal end 9353 of grooves 9352 and, thus, maintains cables 240 (FIG. 15) in a tensioned state. It should be noted that the tensioning mechanism, e.g., slider 9370 and rocker 9380, which transition articulation mechanism 9300 from the un-tensioned to the tensioned state, is independent of the locking mechanism, which locks, i.e., fixed, and unlocks the relative position of articulation section 230 (see FIGS. 3 and 5) with respect to longitudinal axis "X." Thus, when articulation lock trigger 9310 is moved initially from the shipping position to the use position, cables 240 (FIG. 15) are tensioned via the proximal translation of slider 9370 which, in turn, translates arms 9336 of cable plate 9330 proximally. However, once moved to the tensioned state, the tension on cables 240 (FIG. 15) remains substantially constant, regardless of the longitudinal movement of shaft 9320.

Figure 97:
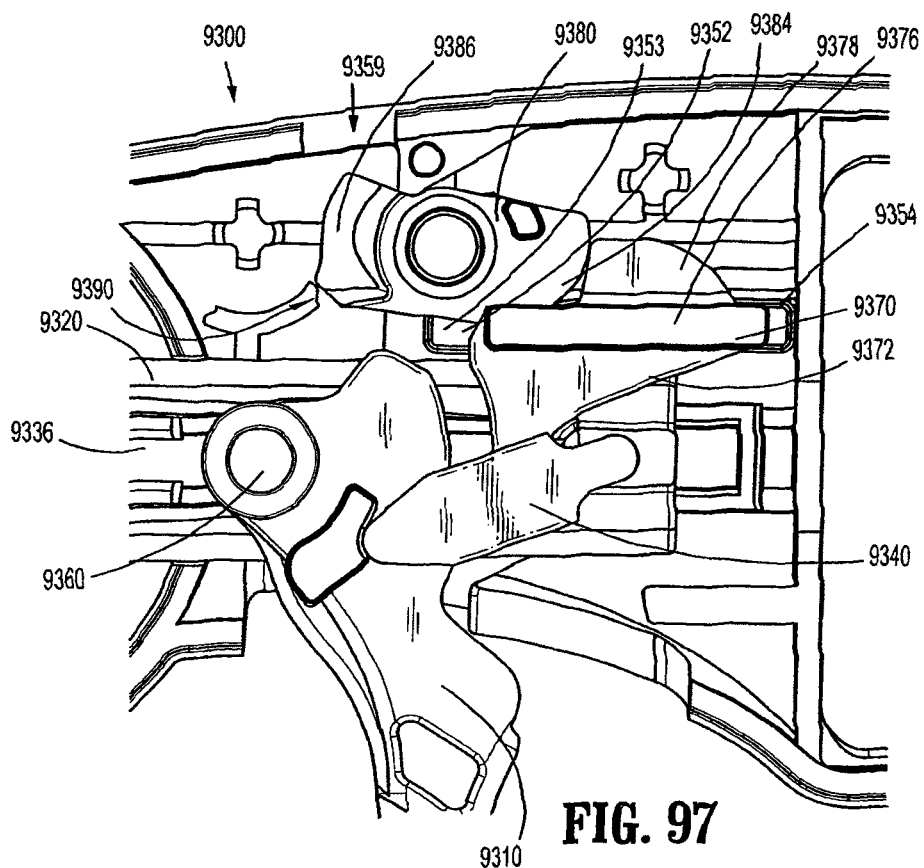
FIG. 97 is a side, cross-sectional view of the articulation mechanism of FIG. 89 shown in the use position.

Referring momentarily to FIG. 97, handle assembly 9350 may include an interference member 9390 disposed thereon and configured to engage distal end 9386 of rocker 9380 upon rotation of rocker 9380 in the clockwise direction (as illustrated in FIG. 94). Interference member 9390 is configured to help maintain rocker 9380 in a fixed position when engaged with protrusion 9378 of slider 9370 such that slider 9370 is maintained in the tensioned position. In other words, interference member 9390, along with the complementary-shaped surface features 9385, 9379 of proximal end 9384 of rocker 9380 and protrusion 9378 of slider 9370, respectively, fix the position of rocker 9380, thereby fixing the position of slider 9370 at proximal ends 9354 of grooves 9352.

With reference again to FIGS. 89-97, in order to lock (or unlock) articulation mechanism 9300 once in the use position, articulation lock trigger 9310 is pulled proximally which, as mentioned above, translates shaft 9320 proximally. As shaft 9320 is translated proximally, lock plate 9324 is similarly moved proximally to pinch the sphere (see FIGS. 70A-70C) to the proximal surface of spherical-shaped cavity 9356, preventing articulation of handle assembly 9350 with respect to elongate outer tube 210 (FIG. 67A) and, thus, fixing the position of articulation section 230 with respect to longitudinal axis "X" (see FIGS. 3 and 5). Any of the locking mechanisms described herein may be provided for fixing the position of articulation section 230 (see FIGS. 3 and 5) relative to longitudinal axis "X." Accordingly, articulation lock trigger 9310 may be selectively depressible to lock and unlock the relative position of articulation section 230 (see FIGS. 3 and 5) with respect to longitudinal axis "X."

The "reset" feature of articulation mechanism 9300 is substantially similar to that of articulation mechanism 8300. More specifically, as mentioned above in relation to articulation mechanism 8300, the user may insert an elongated instrument (or any other suitable elongated member) through aperture 9359 defined within handle assembly 9350. As the instrument is translated through aperture 9359, the instrument eventually contacts distal end 9386 of rocker 9380 and urges rocker 9380 to rotate, for example, in a counter-clockwise direction (as illustrated in FIG. 93). As can be appreciated, urging rocker 9380 to rotate in a counter-clockwise direction (as illustrated in FIG. 93) disengages proximal end 9384 of rocker 9380 from protrusion 9378 of slider 9370 (and/or from interference member 9390 of handle assembly 9350). The disengagement of rocker 9380 and slider 9370 permits slider 9370 to move back to the distal-most position, wherein cables 240 (FIG. 15) are substantially un-tensioned. Shaft 9320 is similarly moved distally such that articulation mechanism 9300 is returned to the shipping position, as shown in FIG. 89.

Figure 98:
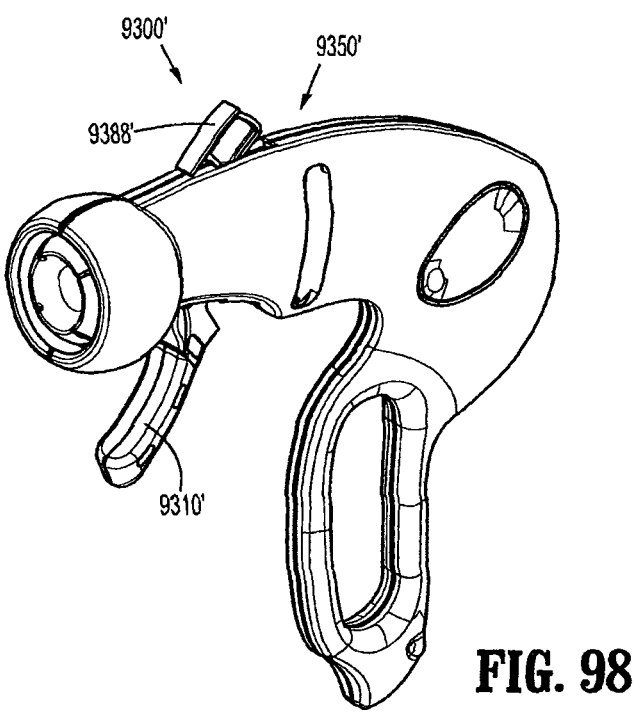
FIG. 98 is a front, perspective view of a handle assembly for housing an articulation mechanism in accordance with yet another embodiment of the present disclosure.
Figure 99:
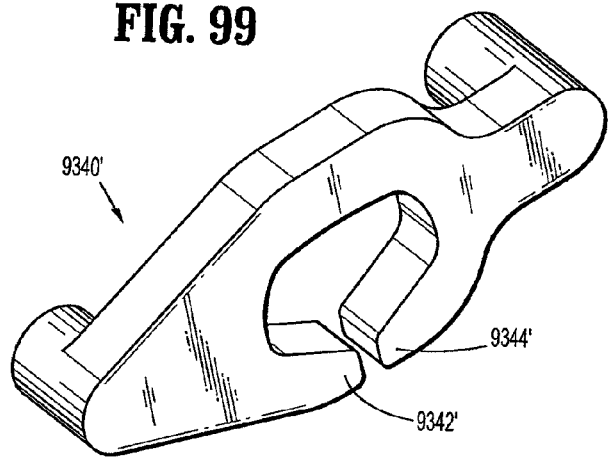
FIG. 99 is an enlarged, perspective view of a linkage for use with the articulation mechanism of any of the embodiments above.
Figure 100:
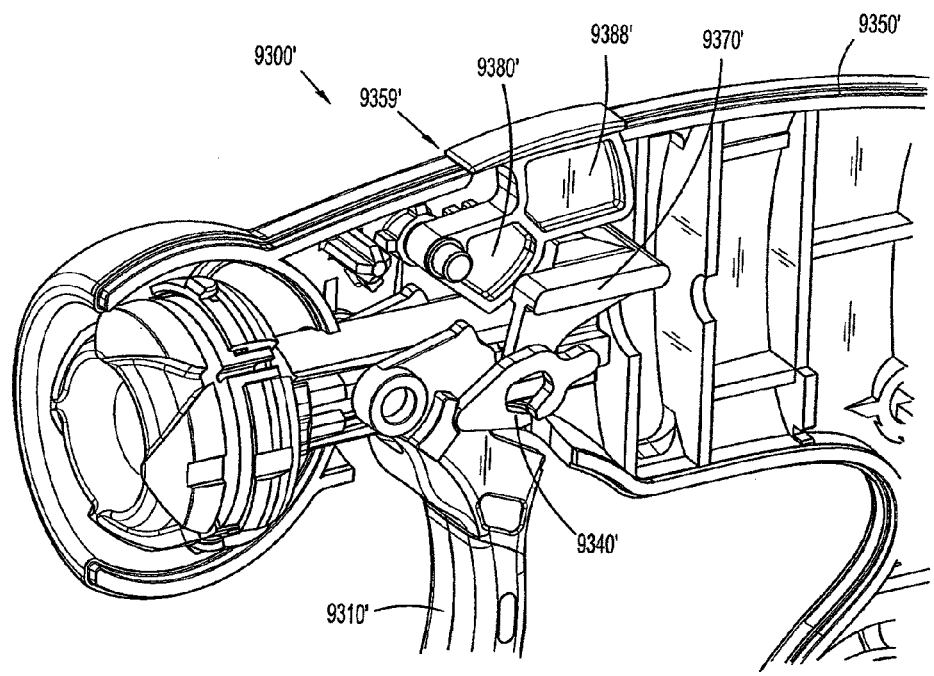
FIG. 100 is a front, perspective cut-away view of an articulation mechanism for use with the handle assembly of FIG. 98.

Turning now to FIGS. 98-100, in another embodiment of the articulation mechanism, shown as articulation mechanism 9300', rocker 9380' includes a lever 9388' extending upwardly therefrom. Lever 9388' extends through a slot 9359' defined within handle assembly 9350'. Rocker 9380' of articulation mechanism 9300' differs from rocker 9380 of articulation mechanism 9300 in that rocker 9380' of articulation mechanism 9300' may be manually rotated by depressing lever 9388' (rather than by pulling articulation lock trigger 9310'). Additionally, rocker 9380' obviates the need to insert an elongated instrument into handle assembly 9350' to reset articulation mechanism 9300'.

As shown in FIGS. 98 and 99, when articulation mechanism 9300' is in the shipping position, lever 9388' extends from handle assembly 9350' (when rocker 9380' is disengaged from slider 9370' (FIG. 100). Thus, in order to tension cables 240 (FIG. 15), e.g., to move articulation mechanism 9300' to the use position, the user depressed lever 9388', which rotates rocker 9380' clockwise (as illustrated in FIG. 94) into engagement with slider 9370' such that, fixing slider 9370' at the proximal ends of the grooves (not explicitly shown) and, thus, maintaining cables 240 (FIG. 15) in a tensioned state. To move articulation mechanism 9300' back to the shipping position, lever 9388' is pulled upwardly to rotate rocker 9380' in a counter-clockwise direction (as illustrated in FIG. 93), thereby disengaging rocker 9380' from slider 9370', allowing slider 9370' to translate distally and un-tension cables 240 (FIG. 15).

Turning now to FIGS. 99-100, articulation mechanism 9300' may also include flexible linkages 9340'. Flexible linkages 9340' of articulation mechanism 9300' each define a generally "C"-shaped configuration that provides additional flexibility to linkages 9340'. The flexible configuration of linkages 9340' facilitate a uniform clamping force as articulation lock trigger 9310' is moved between the unlocked and locked positions despite unavoidable tolerance variations, thereby allowing for smooth, efficient transition of articulation mechanism 9300' between the unlocked and locked positions. Additionally, the opposed fingers 9342' and 9344' of linkages 9340' may be configured to contact one another when linkages 9340' are flexed under a heavy load, thereby preventing further flexion of linkage 9340'. In other words, while linkages 9340' permit some flexion to promote a uniform clamping force upon depression of articulation lock trigger 9310', fingers 9342', 9344' provide support to linkage 9340' by inhibiting over-flexion of linkages 9340'.

Referring now to FIGS. 101-103, a cable tensioning mechanism is shown by 10100. Cable tensioning mechanism 10100 is configured for transitioning between a shipping position, wherein cables 240 (FIG. 15) are substantially un-tensioned, and a use position, wherein cables 240 (FIG. 15) are tensioned. Cable tensioning mechanism 10100 includes a cam member 10110 that is rotatable 90 degrees with respect to outer shaft 10120 between a shipping position and a use position. Cam member 10110 is coupled to a pusher 10130 that translates longitudinally upon rotation of cam member 10110 between the shipping and use positions to tension (or un-tension) cables 240 (FIG. 15). A ferrule 10140 is engaged to cable shaft 10150 and provides reinforcement to cable shaft 10150 at the interface between cable shaft 10150 and handle assembly 10160.

As best shown in FIG. 103, cable plate 10170 includes four (4) apertures 10172 defined therethrough for fixedly retaining the four (4) articulation cables 240 (FIG. 15) therein. Cable plate 10170 is fixedly retained in longitudinal position within spherical cavity 10162 of handle assembly 10160 such that the proximal ends of articulation cables 240 (FIG. 15) are similarly fixedly retained in longitudinal position within spherical cavity 10162 of handle assembly 10160. Thus, instead of cable plate 10170 translating longitudinally with respect to handle assembly 10160 to tension (or un-tension) articulation cables 240 (FIG. 15) as in some of the previous embodiments, the entire cable shaft 10150 is translated with respect to handle assembly 10160 and, thus, with respect to cable plate 10170, for tensioning (and un-tensioning) articulation cables 240 (FIG. 15).

Referring now to FIGS. 101-102C, pusher 10130 is disposed annularly about outer shaft 10120 and includes a tubular body 10132 and a proximal mouth 10134 including a pair of slots 10136 defined therein. Pusher 10130 is also coupled to ferrule 10140. More particularly, tabs 10138, which extend inwardly from pusher 10130 at distal end 10133 thereof, engage lips 10144, which extend outwardly from distal end 10143 of ferrule 10140. As mentioned above, ferrule 10140 is engaged to cable shaft 10150 and reinforces cable shaft 10150 at the proximal end thereof. Cam member 10110 includes a body portion 10112 disposable about tubular body 10132 of pusher 10130 and a pair of proximally-extending arms 10114.

Each arm 10114 includes a peg 10116 extending inwardly therefrom and defining a cam surface 10118. Pegs 10116 are configured to be rotatably disposed within slots 10136 of pusher 10130. As mentioned above, cam member 10110 is rotatable 90 degrees with respect to outer shaft 10120 about pusher 10130. More specifically, cam member 10110 is rotatable from a shipping position, wherein body portion 10112 of cam member 10110 is positioned adjacent tubular body 10132 of pusher 10130 to a use position, wherein cam member 10110 is rotated about pegs 10116 (which are disposed within slots 10136 of pusher 10130) such that body portion 10112 of cam member is displaced from tubular body 10132 of pusher 10130. Upon rotation of cam member 10110 with respect to pusher 10130, cam surfaces 10118 of pegs 10116 cam along slots 10136 of mouth 10134 of pusher 10130, urging pusher 10130 distally which, in turn, urges ferrule 10140 and cable shaft 10150 distally relative to handle assembly 10160. Thus, as can be appreciated, translating ferrule 10140 and cable shaft 10150 distally with respect to handle assembly 10160 translates the entire proximal portion of the instrument distally, including the proximal ends of articulation cables 240 (FIG. 15) such that articulation cables 240 (FIG. 15) are tensioned.

The operation of cable tensioning mechanism 10100 will now be described with reference to FIGS. 101 and 103. Initially, when tensioning mechanism 10100 is in the shipping, or un-tensioned position, as shown in FIG. 101, body portion 10112 of cam member 10110 is positioned adjacent tubular body 10132 of pusher 10130 and cable shaft 10150 is in a proximal-most position with respect to handle assembly 10160 such that articulation cables 240 (FIG. 15) are substantially un-tensioned.

In order to tension articulation cables 240 (FIG. 15), i.e., in order to transition tensioning mechanism 10100 to the use position, cam member 10110 is rotated 90 degrees about pegs 10116 from the shipping position to the use position. As mentioned above, rotating cam member 10110 about pegs 10116 causes cam surfaces 10118 of pegs 10116 to cam along slots 10136 of mouth 10134 of pusher 10130, urging pusher 10130, ferrule 10140, and cable shaft 10150 distally. As a result, the proximal end of the instrument is urged distally with respect to handle assembly 10160 to tension articulation cables 240 (FIG. 15). To reset, or return tensioning mechanism 10100 to the shipping position, cam member 10110 is simply rotated back to the position adjacent outer shaft 10120, allowing pusher 10130, ferrule 10140 and cable shaft 10150 to return proximally to the shipping position to un-tension articulation cables 240 (FIG. 15).

As can be appreciated, tensioning mechanism 10100 may be used in conjunction with any of the above-described articulation mechanisms to provide independent mechanisms for transitioning the instrument from a shipping position to a use position, i.e., for tensioning articulation cables 240 (FIG. 15), and for locking (or un-locking) the relative position of articulation section 230 (see FIGS. 3 and 5) relative to longitudinal axis "X."

Figure 104:
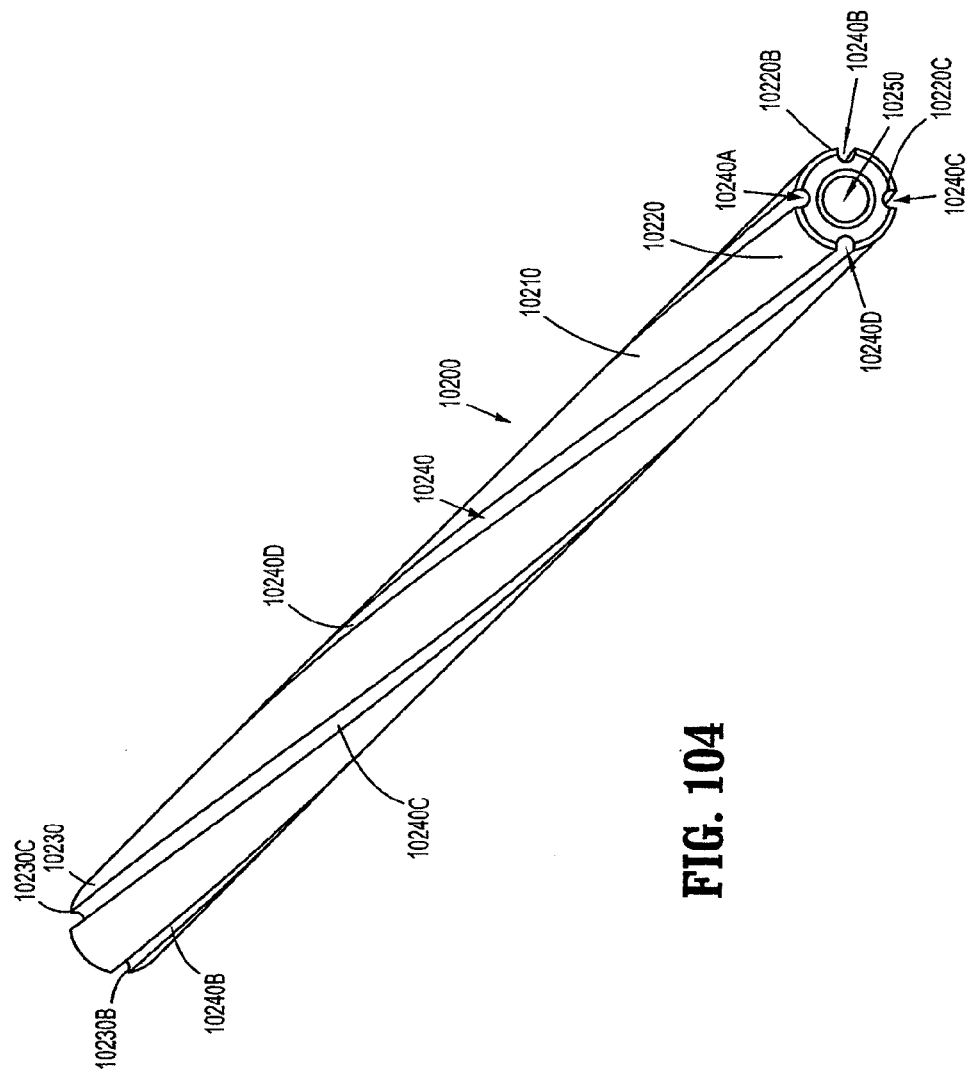

Turning now to FIG. 104, a cable guiding rod is shown generally as 10200. Cable guiding rod 10200 is configured for positioning within elongate shaft 210 (see FIG. 5) for guiding articulation cables 240 (FIG. 15) from articulation section 230 (see FIGS. 3 and 5), through elongate shaft 210 (see FIG. 5), to cable plate 311 (FIG. 11A) wherein the proximal ends of articulation cables 240 (FIG. 15) are secured. As discussed above, articulation cables 240 (FIG. 15) are selectively tensionable to transition between a shipping position and a use position. Further, each of articulation cables $240_{A-D}$ (FIG. 15) is selectively tensionable upon articulation of the handle assembly 300 (FIG. 1) with respect to longitudinal axis "X" (depending on the direction of articulation) to articulate articulation section 230 (see FIGS. 3 and 5) with respect to longitudinal axis "X" in a similar direction.

In order for the articulation of articulation section 230 (see FIGS. 3 and 5) to correspond to the same direction of articulation as handle assembly 300 (see FIG. 1), the distal ends of articulation cables $240_{A-D}$ (FIG. 15), which are engaged to cable plate 311 (see FIG. 11A), are rotated 180 degrees with respect to the proximal ends of articulation cables $240_{A-D}$ (FIG. 15), which are engaged within distal outer tube 220 (FIG. 20). Thus, cable guiding rod 10200 includes four (4) channels 10240 defined on external surface 10210 thereof, each channel $10240_{A-D}$ configured to retain one of articulation cables $240_{A-D}$ (FIG. 15) therein. Each channel $10240_{A-D}$ winds helically about cable guide rod 10200 such that, for example, proximal end $10230_C$ of channel $10240_C$ is disposed on a top side of cable guiding rod 10200 and winds therearound from proximal end 10230 of cable guiding rod 10200 to distal end 10220 of cable guiding rod 10200 such that distal end $10220_C$ of channel $10240_C$ is disposed on a bottom side of cable guiding rod 10200. Similarly, for example, proximal end $10230_B$ of channel $10240_B$ is disposed on a right side of cable guiding rod 10200 and winds therearound from proximal end 10230 of cable guiding rod 10200 to distal end 10220 of cable guiding rod 10200 such that distal end $10220_C$ of channel $10240_C$ is disposed on a left side of cable guiding rod 10200. This configuration of cable guiding rod 10200 reduces the friction on articulation cables 240 (FIG. 15) and improves the stability of consistency of articulation of articulation section 230 (see FIGS. 3 and 5).

With continued reference to FIG. 104, cable guiding rod 10200 further includes a central lumen 10250 extending therethrough. Central lumen 10250 is configured for insertion of torque shaft 499 (see FIGS. 11B and 11C) therethrough. Torque shaft 499 (see FIGS. 11B and 11C) receives increased support by being disposed within cable guiding rod 10200.

Figure 105:
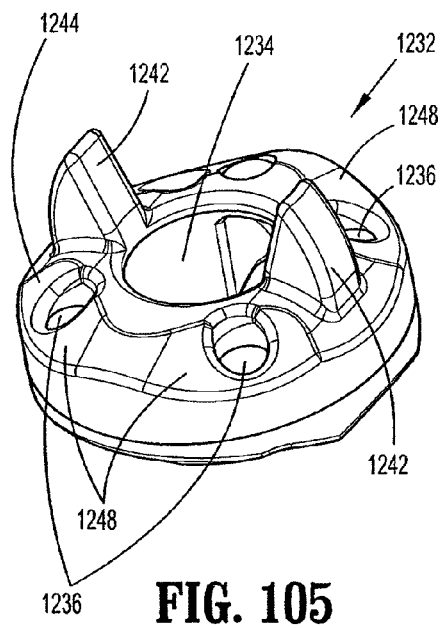
Figure 106:
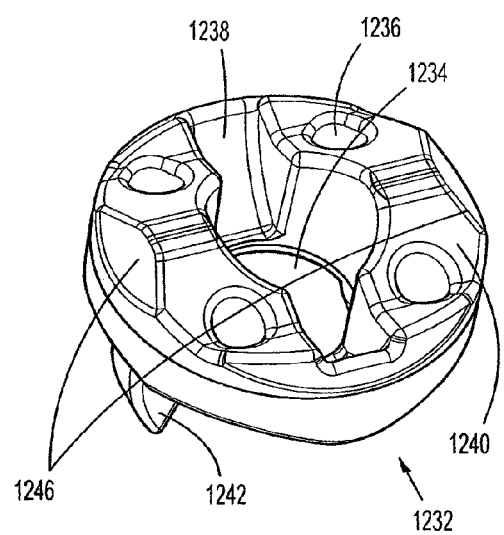

Referring now to FIGS. 105-106, another embodiment of the articulation links is shown. Articulation links 1232 are substantially similar to articulation links 232, 234, discussed above (see FIGS. 13-15), and thus will only be discussed in detail herein to the extent necessary to describe differences in construction and use thereof. As seen in FIGS. 105 and 106, each articulation link 1232 includes a central opening 1234 and a plurality of bores 1236, e.g., four (4) bores 1236, positioned about central opening 1234. Central openings 1234 of articulation links 1232 are adapted to receive distal torque tube 492 (FIG. 20) therethrough, while each bore 1236 is configured to receive an articulation cable 240 (FIG. 25) therethrough.

Each articulation link 1232 further includes a pair of recesses 1238 defined within proximal surfaces 1240 thereof and a pair of extension members 1242 extending distally from distal surfaces 1244 thereof. Further, proximal and distal surfaces 1240, 1244, respectively, of adjacent articulation links 1232 are contoured to mate with one another, while still allowing a certain degree of motion relative to one another. Likewise, the corresponding extension members and recesses 1238, 1242, respectively, of adjacent articulation links 1232 are configured to engage one another, while allowing for a certain degree of motion relative to one another.

With continued reference to FIGS. 105-106, each articulation link 1232 further includes one or more indents, or chamfers 1246, 1248, defined within proximal and distal surfaces 1240, 1244, respectively, thereof. More specifically, as shown in FIG. 105, a pair of chamfers 1248 are defined within distal surface 1244 of each articulation link 1232 between adjacent bores 1236 thereof and on the outer periphery of distal surface 1244. Similarly, as shown in FIG. 106, a pair of chamfers 1246 are defined within proximal surface 1240 of each articulation link 1232 between adjacent bores 1236 thereof and on the outer periphery of proximal surface 1240. However, it is contemplated that more or fewer chamfers 1246, 1248 may be provided and/or that chamfers 1248, 1246 of proximal and distal surfaces 1240, 1244, respectively, of articulation links 1232 may be positioned in various other configurations on proximal and distal surfaces 1240, 1244, respectively, of articulation links 1232.

Figure 107:
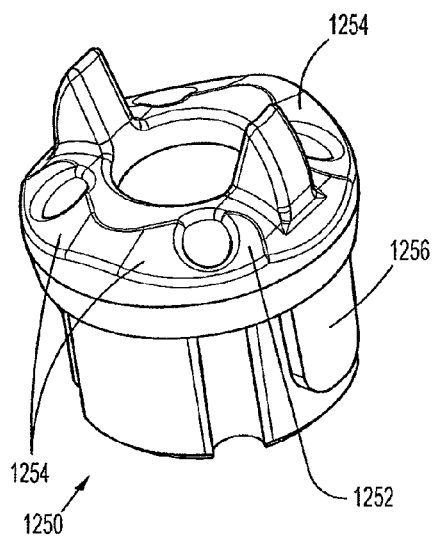
Figure 108:
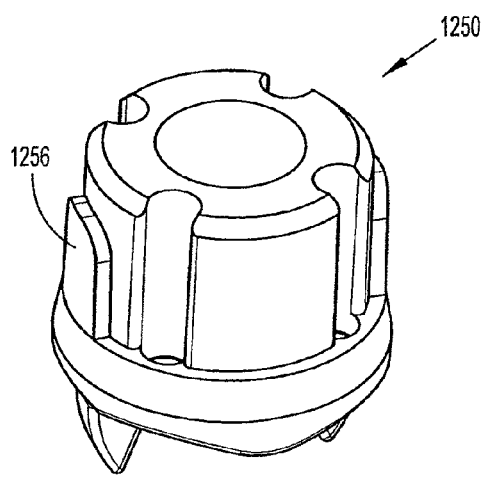

Referring now to FIGS. 107-108, proximal-most articulation link 1250 is substantially similar to proximal-most link 496, discussed above (see FIG. 11A), and thus will only be discussed in detail herein to the extent necessary to describe differences in construction and use thereof. Specifically, proximal-most articulation link 1250 includes a distal surface 1252 that is substantially similar to distal surfaces 1244 of articulation links 1232 discussed above (see FIGS. 105-106). In other words, proximal-most articulation link 1250 includes one or more chamfers 1254 defined within distal surface 1252 of proximal-most articulation link 1250 toward the outer periphery thereof. However, unlike articulation links 1232, proximal-most articulation link 1250 further includes an extension 1256 protruding proximally therefrom that is configured to be securely received within the distal end of endoscopy assembly 200 (see FIG. 32).

With reference now to FIGS. 109 and 110, there is illustrated an articulation section 2230 including a plurality of articulation links 1232 and a proximal-most articulation link 1250. Articulation section 2230 may be supported on distal end 214 of elongate outer tube 210 (FIG. 3). Articulation section 2230 is configured to articulate with respect to elongate outer tube 210 upon actuation of handle assembly 300 (FIG. 3). As described hereinabove, elongate outer tube 210 and articulating section 2230 are longitudinally aligned with each other when handle assembly 300 is positioned in a neutral position. The movement of articulation section 2230 relative to elongate outer tube 210 minors the motion of handle assembly 300 with respect to elongate outer tube 210. Furthermore, a tool assembly or any suitable end effector such as end effector 260 (FIG. 7), may be operatively coupled to a distal end 2238 of articulation section 2230.

The number of articulation links 1232 may be tailored to a particular application to achieve the desired flexibility or degree of articulation. Regardless of the number of the articulation links 1232, articulation section 2230 may move from a first position that is longitudinally aligned with elongate outer tube 210 to numerous offset positions with respect to elongate outer tube 210.

With continued reference to FIGS. 109 and 110, each articulation link 1232 is oriented or offset 90 degrees relative to an adjacent articulation link 1232 about a longitudinal axis "L-L" defined by articulation section 2230. In this manner, when extension members 1242 of articulation links 1232 are slidably disposed in the corresponding recesses 1238 of an adjacent articulation link 1232, chamfers 1248 defined in distal surface 1244 of articulation link 1232 at least partially overlap with chamfers 1246 defined in proximal surface 1240 of the adjacent articulation link 1232 to define a gap 2275 therebetween. Similarly, chamfers 1254 defined in distal surface 1252 of proximal-most articulation link 1250 at least partially overlap with chamfers 1246 defined in proximal surface 1240 of an adjacent articulation link 1232 to define a gap 2375 therebetween.

Gaps 2275, 2375 defined by or near the outer peripheries of adjacent links 1232, 1250 are particularly advantageous in embodiments where articulation section 2230 is encased within a shrink-wrap material, such as sheath 270 (FIGS. 7, 11A and 20) or other form-fitting encasement material, as shown in FIGS. 111 and 112. More specifically, by providing this clearance, chamfers 1246, 1248 and 1254 reduce the likelihood of catching, pinching and/or tearing of the shrink wrap material or sheath 270 between adjacent articulation links 1232 and/or proximal-most articulation link 1250 during articulation of articulation section 2230, which creates a portion of the plurality of articulation links 1232 and proximal-most articulation link 1250 in compression, as shown in FIG. 112. Further, during the shrink-wrapping, e.g., heat-shrinking, process, chamfers 1246, 1248 and 1254 help ensure that the shrink-wrap material or sheath 270 is uniformly distributed over articulation section 2230. A uniform distribution of the shrink-wrap material or sheath 270 promotes more evenly-distributed stress concentrations along the shrink-wrap material or sheath 270 during articulation of articulation section 2230, thereby reducing the likelihood of tearing of the shrink-wrap material or sheath 270.

It will be understood that various modifications may be made to the embodiments of the presently disclosed surgical device. Therefore, the above description should not be construed as limiting, but merely as exemplifications of embodiments. Those skilled in the art will envision other modifications within the scope and spirit of the present disclosure.

What is claimed is:

1. An articulation mechanism configured for use with a surgical instrument defining a longitudinal axis, the articulation mechanism comprising:
    an articulation assembly;
    a plurality of cables coupled to the articulation assembly at a proximal end thereof and extending distally therefrom, the plurality of cables configured to engage an end effector assembly of the surgical instrument at a distal end thereof; and
    a trigger coupled to the articulation assembly, the trigger irreversibly moveable from a first position, wherein the cables are substantially un-tensioned, to a second position, wherein each of the cables is disposed in an initial tensioned position, the trigger, when in the second position, configured to move between:
        an unlocked position, wherein each of the cables is selectively tensionable from the initial tensioned position to a further tensioned position to articulate the end effector assembly relative to the longitudinal axis of the surgical instrument, and
        a locked position, wherein the tensions on the cables are maintained to lock the end effector assembly in an articulated position.

2. The articulation mechanism according to claim 1, wherein the articulation assembly includes a ball and a socket, the socket configured to retain the proximal ends of the cables therein and configured to rotate about the ball to selectively tension the cables, thereby articulating the end effector assembly relative to the longitudinal axis.

3. The articulation mechanism according to claim 2, further comprising a shaft extending proximally from the socket, the shaft having the trigger coupled thereto, the shaft longitudinally translatable between a distal position, when the trigger is disposed in the first position, an intermediate position, when the trigger is moved to the unlocked position, and a proximal position, when the trigger is moved to the locked position.

4. The articulation mechanism according to claim 3, further comprising a pivoting linkage pivotably coupled to the shaft at a first end thereof and pivotably coupled to the trigger at a second end thereof, the pivoting linkage movable between a first linkage position corresponding to the unlocked position of the trigger, wherein the second end of the pivoting linkage is disposed below a plane defined by a line extending between the first end of the pivoting linkage and a pivot point coupling the trigger and the shaft, and a second linkage position, wherein the second end of the pivoting linkage is disposed above the plane defined by the line extending between the first end of the pivoting linkage and the pivot point coupling the trigger and the shaft.

5. The articulation mechanism according to claim 1, further comprising a biasing member coupled to the articulation assembly, wherein the biasing member is movable between a disengaged position when the trigger is in the first position, and an engaged position when the trigger is in the second position, and wherein when the biasing member is in the engaged position, the biasing member biases the trigger toward the unlocked position.

6. The articulation mechanism according to claim 5, wherein the biasing member is one of a leaf spring or a flat spring.

7. The articulation mechanism according to claim 1, wherein the trigger includes a contoured outer surface configured to engage a protrusion extending from the articulation assembly and to move relative thereto such that, upon movement of the trigger from the first position to the second position, the cables are moved from the substantially un-tensioned position to the initial tensioned position and are inhibited from returning to the substantially un-tensioned position, and wherein, upon movement of the trigger from the unlocked position to the locked position, the tensions on the cables are maintained to lock the end effector assembly in position.

8. The articulation mechanism according to claim 1, further comprising an elongated tubular member including a plurality of slots defined therein and extending longitudinally therealong, the slots helically disposed about the elongated tubular member such that a position of each slot at a first end of the elongated tubular member is rotated at least one half of a turn relative to a position of the slot at a second end of the elongated tubular member, each slot configured to retain at least a portion of one of the cables therein.

9. The articulation mechanism according to claim 1, further comprising a plurality of articulation linkages longitudinally aligned with one another and configured to receive the cables therethrough, the articulation linkages configured for articulation relative to one another upon selective tensioning of the cables to permit articulation of the end effector assembly relative to the longitudinal axis.

10. The articulation mechanism according to claim 9, wherein at least one of the articulation linkages includes a chamfered portion defined within at least one of the proximal and distal surfaces thereof toward an outer circumference thereof.

11. A surgical device for performing surgery, comprising:
    an elongate member defining a longitudinal axis;
    an articulation section extending from the elongate member, the articulation section transitionable between a straight position in which the articulation section is aligned with the longitudinal axis and a plurality of articulated positions in which the articulation section is offset from the longitudinal axis, the articulation section including a plurality of articulation links arranged in a linear fashion, each articulation link including chamfered portions, the chamfered portions of adjacent articulation links in juxtaposed relation to one another;

a handle assembly operatively coupled to the articulation section, the handle assembly including:
  a support member; and
  a trigger operatively coupled to a biasing member, the trigger irreversibly transitionable from a first position in which the biasing member is disengaged from the support member to a second position in which the biasing member is engaged with the support member;
an articulation cable interconnecting the articulation section with the handle assembly, the articulation cable operably coupled to the biasing member; and
an end effector operatively coupled to the articulation section.

12. The surgical device for performing surgery according to claim 11, wherein each of the plurality of articulation links includes proximal and distal surfaces, each surface including a pair of chamfered portions.

13. The surgical device for performing surgery according to claim 12, wherein the pair of chamfered portions diametrically oppose each other.

14. The surgical device for performing surgery according to claim 12, wherein each surface defines the pair of chamfered portions near an outer periphery of the surface.

15. The surgical device for performing surgery according to claim 12, wherein each articulation link includes at least a pair of bores on a peripheral portion of the articulation link, the bores adapted and dimensioned to receive an articulation cable therein.

16. The surgical device for performing surgery according to claim 15, wherein movement of the handle assembly to angle the handle assembly with respect to the longitudinal axis of the elongate member results in corresponding articulation of the articulation section to an angled position with respect to the longitudinal axis of the elongate member.

17. The surgical device for performing surgery according to claim 12, wherein each articulation link defines a channel configured and dimensioned to receive an actuation cable therethrough for actuation of the end effector.

18. The surgical device for performing surgery according to claim 11, wherein each articulation link includes a proximal surface and a distal surface, one of the proximal or distal surfaces defining a pair of recesses, the other one of the proximal or distal surfaces including a pair of extension members extending axially therefrom.

19. The surgical device for performing surgery according to claim 18, wherein the pair of extension members are configured and dimensioned to at least partially slidably engage the pair of recesses of an adjacent articulation link.

20. The surgical device for performing surgery according to claim 19, wherein the distal surface includes a contoured profile that is configured to mate with a contoured profile of the proximal surface of the adjacent articulation link.

21. The surgical device for performing surgery according to claim 11, further comprising a conformable sheath substantially encasing the articulation section.

22. The surgical device for performing surgery according to claim 11, wherein the biasing member is a flat spring.

* * * * *